US011149192B1

(12) United States Patent
Barnes et al.

(10) Patent No.: US 11,149,192 B1
(45) Date of Patent: Oct. 19, 2021

(54) ACTUATING MATERIALS AND METHOD OF MAKING AND USING THE SAME

(71) Applicants: Jonathan C. Barnes, St. Louis, MO (US); Angelique F. Greene, St. Louis, MO (US); Kevin Liles, St. Louis, MO (US); Abigail Delawder, St. Louis, MO (US)

(72) Inventors: Jonathan C. Barnes, St. Louis, MO (US); Angelique F. Greene, St. Louis, MO (US); Kevin Liles, St. Louis, MO (US); Abigail Delawder, St. Louis, MO (US)

(73) Assignee: Washington University, St. Louis, MO (US)

( * ) Notice: Subject to any disclaimer, the term of this patent is extended or adjusted under 35 U.S.C. 154(b) by 113 days.

(21) Appl. No.: 15/939,515

(22) Filed: Mar. 29, 2018

Related U.S. Application Data

(60) Provisional application No. 62/478,274, filed on Mar. 29, 2017, provisional application No. 62/599,215, filed on Dec. 15, 2017.

(51) Int. Cl.
*C09K 9/02* (2006.01)
*A61L 27/52* (2006.01)
*A61L 27/02* (2006.01)
*A61L 27/18* (2006.01)

(52) U.S. Cl.
CPC .............. *C09K 9/02* (2013.01); *A61L 27/025* (2013.01); *A61L 27/18* (2013.01); *A61L 27/52* (2013.01); *C09K 2211/1466* (2013.01)

(58) Field of Classification Search
CPC combination set(s) only.
See application file for complete search history.

(56) References Cited

U.S. PATENT DOCUMENTS

| 8,192,485 | B2 | 6/2012 | Ravi | |
|---|---|---|---|---|
| 8,877,227 | B2 | 11/2014 | Ravi | |
| 2005/0282925 | A1* | 12/2005 | Schlenoff | G02B 1/04 523/106 |

OTHER PUBLICATIONS

A Light-Stimulated molecular switch driven by radical-radical interactions in water, Li et al.. Angew. Chem. Int. Ed. 2011, 50, 6782-6788.*
Ahmed E.M. (2015)—Hydrogel: Preparation, characterization, and applications: A review, Journal of Advanced Research, pp. 105-121, vol. 6, No. 2.
Appel E.A. et al. (2010)—Supramolecular Cross-Linked Networks via Host-Guest Complexation with Cucurbit [8] uril, Journal of the American Chemical Society, pp. 14251-14260, vol. 132, No. 16.
Appel E.A. et al. (2012)—Supramolecular polymeric hydrogels, Chemical Society Reviews, pp. 6195-6214, vol. 41, No. 18.
Appel E.A. et al. (2012)—Ultra high-water-content supramolecular hydrogels exhibiting multistimuli responsiveness, Journal of the American Chemical Society, pp. 11767-11773, vol. 134, No. 28.
Balamurugan Aa et al. (2013)—π-Conjugated polymer-$Eu^{3+}$ complexes: Versatile luminescent molecular probes for temperature sensing, Journal of Materials Chemistry A, pp. 2256-2266, vol. 1, No. 6.
Bar-Cohen Y., Zhang Q. (2008)—Electroactive Polymer Actuators and Sensors, MRS Bulletin, pp. 173-181, vol. 33.
Barnes J.C. et al. (2012)—Mechanically induced intramolecular electron transfer in a mixed-valence molecular shuttle, Proceedings of the National Academy of Sciences, pp. 11546-11551, vol. 109, No. 29.
Barnes J.C. et al. (2013)—A radically configurable six-state compound, Science, pp. 429-433, vol. 339.
Baughman R.H. (1996)—Conducting polymer artificial muscles, Synthetic Metals, pp. 339-353, vol. 78, No. 3.
Beebe D.J. et al. (2000)—Microfluidic tectonics: a comprehensive construction platform for microfluidic systems, Proceedings of the National Academy of Sciences, pp. 13488-13493, vol. 97, No. 25.
Bird C.L., Kuhn A.T. (1981)—Electrochemistry of the viologens, Chemical Society Reviews, pp. 49-82, vol. 10, No. 1.
Bockman T.M. et al. (1990)—Isolation and Oxidation-Reduction of Methylviologen Cation Radicals. Novel Disproportionation in Charge-Transfer Salts by X-ray Crystallography, Journal of Organic Chemistry, pp. 4127-4135, vol. 55, No. 13.
Bogush G.H., Tracy M.A., Zukoski C.F.I. (1988)—Preparation of monodisperse silica particles: Control of size and mass fraction, Journal of Non-Crystalline Solids, pp. 95-106, vol. 104.
Bromberg L.E., Ron E.S. (1998)—Temperature-responsive gels and thermogelling polymer matrices for protein and peptide delivery, Advanced Drug Delivery Reviews, pp. 197-221, vol. 31, No. 3.
Brunsveld L. et al. (2001)—Supramolecular Polymers, Chemical Reviews, pp. 4071-4098, vol. 101, No. 12.
Burnworth M. et al. (2011)—Optically healable supramolecular polymers, Nature, pp. 334-337, vol. 472, No. 7343.
Caló E., Khutoryanskiy V. V. (2015)—Biomedical applications of hydrogels: A review of patents and commercial products, European Polymer Journal, pp. 252-267, vol. 65.
Capadona J.R. et al. (2008)—Stimuli-responsive polymer nanocomposites inspired by the sea cucumber dermis, Science, pp. 1370-1374, vol. 319.
Chen M. et al. (2017)—Living Additive Manufacturing: Transformation of Parent Gels into Diversely Functionalized Daughter Gels Made Possible by Visible Light Photoredox Catalysis, ACS Central Science, pp. 124-134, vol. 3, No. 2.
Chen M. et al. (2016)—Light-Controlled Radical Polymerization: Mechanisms, Methods, and Applications, Chemical Reviews, pp. 10167-10211, vol. 116, No. 17.
Cheng C. et al. (2015)—An artificial molecular pump, Nature Nanotechnology, pp. 547-553, vol. 10.
Corrigan N. et al. (2016)—Photocatalysis in organic and polymer synthesis, Chemical Society Reviews, pp. 6165-6212, vol. 45, No. 22.

(Continued)

*Primary Examiner* — Monique R Peets

(57) ABSTRACT

The present disclosure provides for a photoredox-responsive material, processes of making the photoredox-responsive material, and methods of use thereof.

22 Claims, 24 Drawing Sheets

(56) References Cited

OTHER PUBLICATIONS

Dai S., Ravi P., Tam K.C. (2008)—pH-Responsive polymers: Synthesis, properties and applications, Soft Matter, pp. 435-449, vol. 4, No. 3.
De Greef T.F.A. et al. (2009)—Supramolecular polymerization, Chemical Reviews, pp. 5687-5754, vol. 109, No. 11.
Dong L., Jiang H. (2007)—Autonomous microfluidics with stimuli-responsive hydrogels, Soft Matter, pp. 1223-1230, vol. 3, No. 10.
Eising S., Lelivelt F., Bonger K.M. (2016)—Vinylboronic Acids as Fast Reacting, Synthetically Accessible, and Stable Bioorthogonal Reactants in the Carboni-Lindsey Reaction, Angewandte Chemie—International Edition, pp. 12243-12247, vol. 55, No. 40.
Evans A.G., Evans J.C., Baker M.W. (1975)—Bipyridyl radical cations. Part I. Electron spin resonance study of the dimerisation equilibrium of morphamquat radical cation in methanol., Journal of the Chemical Society, Perkin Transactions 2, pp. 1310-1311, vol. 2.
Fahrenbach A.C. et al. (2012)—Solution-phase mechanistic study and solid-state structure of a tris(bipyridinium radical cation) inclusion complex, Journal of the American Chemical Society, pp. 3061-3072, vol. 134, No. 6.
Fernández G. (2013)—Liquid-crystal polymers: Exotic actuators, Nature Materials, pp. 12-14, vol. 12, No. 1.
Fox J.D., Rowan S.J. (2009)—Supramolecular polymerizations and main-chain supramolecular polymers, Macromolecules, pp. 6823-6835, vol. 42, No. 18.
Foy J.T. et al. (2017)—Dual-light control of nanomachines that integrate motor and modulator subunits, Nature Nanotechnology, pp. 540-545, vol. 12, No. 6.
Fukino T., Yamagishi H., Aida T. (2017)—Redox-Responsive Molecular Systems and Materials, Advanced Materials, vol. 29, No. 25.
Gaharwar A.K. et al. (2013)—Photocrosslinked nanocomposite hydrogels from PEG and silica nanospheres: Structural, mechanical and cell adhesion characteristics, Materials Science and Engineering C, pp. 1800-1807, vol. 33, No. 3.
Gaharwar A.K., Peppas N.A., Khademhosseini A. (2014)—Nanocomposite hydrogels for biomedical applications, Biotechnology and Bioengineering, pp. 441-453, vol. 111, No. 3.
Galaev I.Y., Mattiasson B. (1999)—'Smart' polymers and what they could do in biotechnology and medicine, Trends in Biotechnology, pp. 335-340, vol. 17.
Gong J.P. (2010)—Why are double network hydrogels so tough? Soft Matter, pp. 2583-2590, vol. 6, No. 12.
Greene A.F. et al. (2017)—Redox-Responsive Artificial Molecular Muscles: Reversible Radical-Based Self-Assembly for Actuating Hydrogels, Chemistry of Materials, pp. 9498-9508, vol. 29, No. 21.
Guo D.-S. et al. (2010)—Electrochemical stimulus-responsive supramolecular polymer based on sulfonatocalixarene and viologen dimers., Chemical communications, pp. 2620-2622, vol. 46, No. 15.
Hara S. et al. (2004)—Gel-like polypyrrole based artificial muscles with extremely large strain, Polymer Journal, pp. 933-936, vol. 36, No. 11.
Haraguchi K., Takehisa T. (2002)—Synthesis of Large-Area Silicon Nanowire Arrays via Self-Assembly Nanoelectrochemistry, Advanced Materials, pp. 1120-1124, vol. 14, No. 16.
Hu Z., Lu X., Gao J. (2001)—Hydrogel Opals, Advanced Materials, pp. 1708-1712, vol. 3, No. 22.
Hünig S. (1967)—Stable radical ions, Pure and Applied Chemistry, pp. 109-122, vol. 15, No. 1.
Iamsaard S. et al. (2014)—Conversion of light into macroscopic helical motion, Nature Chemistry, pp. 229-235, vol. 6, No. 3.
Ionov L. (2013)—Self microorigami: self-folding polymer films, Soft Matter, pp. 6786-6791, vol. 7.
Ionov L. (2015)—Polymeric actuators, Langmuir, pp. 5015-5024, vol. 31, No. 18.
Iwaso K., Takashima Y., Harada A. (2016)—Fast response dry-type artificial molecular muscles with [c2]daisy chains, Nature Chemistry, pp. 625-632, vol. 8, No. 6.
Jager E.W., Smela E., Inganäs O. (2000)—Microfabricating conjugated polymer actuators., Science, pp. 1540-1545, vol. 290, No. 5496.
Jain V. et al. (2009)—High-contrast solid-state electrochromic devices of viologen-bridged polysilsesquioxane nanoparticles fabricated by layer-by-layer assembly, ACS Applied Materials and Interfaces, pp. 83-89, vol. 1, No. 1.
Jain V. et al. (2008)—Solid-state electrochromic devices via Ionic Self-Assembled Multilayers (ISAM) of a polyviologen, Macromolecular Chemistry and Physics, pp. 150-157, vol. 209, No. 2.
Janoschka T. et al. (2015)—An aqueous, polymer-based redox-flow battery using non-corrosive, safe, and low-cost materials, Nature, pp. 78-81, vol. 527, No. 7576.
Juetten M.J., Buck A.T., Winter A.H. (2015)—A radical spin on viologen polymers: Organic spin crossover materials in water, Chemical Communications, pp. 5516-5519, vol. 51, No. 25.
Kassem S. et al. (2017)—Artificial molecular motors, Chemical Society Reviews, pp. 2592-2621, vol. 46, No. 9.
Kolb H.C., Finn M.G., Sharpless K.B. (2001)—Click Chemistry: Diverse Chemical Function from a Few Good Reactions, Angewandte Chemie—International Edition, pp. 2004-2021, vol. 40, No. 11.
Kosower E.M., Cotter J.L. (1964)—Stable Free Radicals. II. The Reduction of 1-Methyl-4-cyanopyridinium Ion to Methylviologen Cation Radical, Journal of the American Chemical Society, pp. 5524-5527, vol. 86, No. 24.
Kosower E.M., Hajdu J. (1971)—Pyridinyl Diradical π-Mer. Magnesium Iodide Complexes, Journal of the American Chemical Society, pp. 2534-2535, vol. 93, No. 10.
Kwon G.H. et al. (2008)—Biomimetic soft multifunctional miniature aquabots, Small, pp. 2148-2153, vol. 4, No. 12.
Lee J.Y. et al. (2006)—Effect of metal nanoparticles on thermal stabilization of polymer/metal nanocomposites prepared by a one-step dry process, Polymer, pp. 7970-7979, vol. 47, No. 23.
Lehn J.M. (2007)—From supramolecular chemistry towards constitutional dynamic chemistry and adaptive chemistry, Chemical Society Reviews, pp. 151-160, vol. 36.
Li H. et al. (2011)—A light-stimulated molecular switch driven by radical-radical interactions in water, Angewandte Chemie—International Edition, pp. 6782-6788, vol. 50, No. 30.
Li H. et al. (2010)—Mechanical bond formation by radical templation, Angewandte Chemie—International Edition, pp. 8260-8265, vol. 49, No. 44.
Li Q. et al. (2015)—Macroscopic contraction of a gel induced by the integrated motion of light-driven molecular motors, Nature Nanotechnology, pp. 161-165, vol. 10, No. 2.
Li Z. et al. (2012)—Mesoporous silica nanoparticles in biomedical applications, Chemical Society Reviews, pp. 2590-2605, vol. 41, No. 7.
Ma Y. et al. (2011)—Polyelectrolyte multilayer films for building energetic walking devices, Angewandte Chemie—International Edition, pp. 6254-6257, vol. 50, No. 28.
Meddahi-Pellé A. et al. (2014)—Organ repair, hemostasis, and in vivo bonding of medical devices by aqueous solutions of nanoparticles, Angewandte Chemie—International Edition, pp. 6369-6373, vol. 53, No. 25.
Michaelis L. (1933)—the Viologen Indicators, The Journal of General Physiology, pp. 859-873, vol. 16, No. 6.
Michaelis L. (1935)—Semiquinones, the intermediate steps of reversible organic oxidation-reduction, Chemical Reviews, pp. 243-286, vol. 16, No. 2.
Michaelis L., Hill E.S. (1933)—Potentiometric Studies on Semiquinones, Journal of the American Chemical Society, pp. 1481-1494, vol. 55, No. 4.
Moon H.J. et al. (2012)—Temperature-responsive compounds as in situ gelling biomedical materials, Chemical Society Reviews, pp. 4860-4883, vol. 41, No. 14.
Morales D. et al. (2014)—Electro-actuated hydrogel walkers with dual responsive legs, Soft Matter, pp. 1337-1348, vol. 10, No. 9.
Nagarjuna G. et al. (2014)—Impact of redox-active polymer molecular weight on the electrochemical properties and transport across porous separators in nonaqueous solvents, Journal of the American Chemical Society, pp. 16309-16316, vol. 136, No. 46.

(56) References Cited

OTHER PUBLICATIONS

Narayanam J.M.R., Stephenson C.R.J. (2011)—Visible light photoredox catalysis: Applications in organic synthesis, Chemical Society Reviews, pp. 102-113, vol. 40, No. 1.

Okahata Y., Seki T. (1986)—Redox-Sensitive Permeation from a Capsule Membrane Grafted with Viologen-Containing Polymers, Journal of the Chemical Society, Chemical Communications articles, pp. 73-75.

Philp D., Fraser Stoddart J. (1996)—Self-Assembly in natural and unnatural systems, Angewandte Chemie (International Edition in English), pp. 1154-1196, vol. 35, No. 11.

Plumeré N. et al. (2014)—A redox hydrogel protects hydrogenase from high-potential deactivation and oxygen damage, Nature Chemistry, pp. 822-827, vol. 6, No. 9.

Prier C.K., Rankic D.A., Macmillan D.W.C. (2013)—Visible Light Photoredox Catalysis with Transition Metal Complexes: Applications in Organic Synthesis, Chemical Reviews, pp. 5322-5363, vol. 113, No. 7.

Punning A. et al. (2014)—Ionic electroactive polymer artificial muscles in space applications, Scientific Reports, pp. 6913-6918, vol. 4.

Rose S. et al. (2014)—Nanoparticle solutions as adhesives for gels and biological tissues, Nature, pp. 382-385, vol. 505.

Rostovtsev V. V. et al. (2002)—A Stepwise Huisgen Cycloaddition Process: Copper(I)-Catalyzed Regioselective "Ligation" of Azides and Terminal Alkynes, Angew. Chem. Int. Ed., pp. 2596-2599, vol. 41, No. 14.

Rowan S.J. et al. (2002)—Dynamic Covalent Chemistry, Angewandte Chemie International Edition, pp. 898-952, vol. 41, No. 6.

Ruff A. et al. (2013)—Redox-active silica nanoparticles. Part 6. Synthesis and spectroscopic and electrochemical characterization of viologen-modified Stöber silica particles with diameters of approximately 125 nm, Journal of Solid State Electrochemistry, pp. 79-97, vol. 17, No. 1.

Sakai Y. et al. (1996)—Humidity sensors based on polymer thin films, Sensors and Actuators, B: Chemical, pp. 85-90, vol. 35.

Shahinpoor M. et al. (1998)—Ionic Polymer—Metal Composites (IPMCs) as Biomimetic Sensors and Actuators—Artificial Muscles—a Review, Smart Materials and Structures, pp. R15-R30, vol. 7.

Shi F.K. et al. (2015)—Highly stretchable and super tough nanocomposite physical hydrogels facilitated by the coupling of intermolecular hydrogen bonds and analogous chemical crosslinking of nanoparticles, Journal of Materials Chemistry B, pp. 1187-1192, vol. 3, No. 7.

Shipway A.N. et al. (2000)—Nanoparticle arrays on surfaces for electronic, optical, and sensor applications, ChemPhysChem, pp. 18-52, vol. 1, No. 1.

Smela E. (2003)—Conjugated Polymer Actuators for Biomedical Applications, Advanced Materials, pp. 481-494, vol. 15, No. 6.

Stober W., Fink A. (1968)—Controlled Growth of Monodisperse Silica Spheres in the Micron Size Range, Journal of Colloid and Interface Science, pp. 62-69, vol. 26.

Stoddart J.F. (2014)—Putting Mechanically Interlocked Molecules (MIMs) to Work in Tomorrow's World, Angewandte Chemie—International Edition, pp. 11102-11104, vol. 53, No. 42.

Stoddart J.F. (2009)—Thither supramolecular chemistry? Nature Chemistry, pp. 14-15, vol. 1, No. 1.

Stoyanov H. et al. (2013)—Soft conductive elastomer materials for stretchable electronics and voltage controlled artificial muscles, Advanced Materials, pp. 578-583, vol. 25, No. 4.

Stuart M.A.C. et al. (2010)—Emerging applications of stimuli-responsive polymer materials, Nature Materials, pp. 101-113, vol. 9, No. 2.

Sun J. et al. (2015)—Visible Light-Driven Artificial Molecular Switch Actuated by Radical-Radical and Donor-Acceptor Interactions, Journal of Physical Chemistry A, pp. 6317-6325, vol. 119, No. 24.

Takashima Y. et al. (2012)—Expansion-contraction of photoresponsive artificial muscle regulated by host-guest interactions, Nature Communications, pp. 1270-1278, vol. 3.

Tamesue S. et al. (2010)—Photoswitchable Supramolecular Hydrogels Formed by Cyclodedtrins and Azobenzene Polymers, Angewandte Chemie—International Edition, pp. 7461-7464, vol. 49.

Tatsuma T., Takada K., Miyazaki T. (2007)—UV-light-induced swelling and visible-light-induced shrinking of a $TiO_2$-containing redox gel, Advanced Materials, pp. 1249-1251, vol. 19, No. 9.

Teegardin K. et al. (2016)—Advances in Photocatalysis: A Microreview of Visible Light Mediated Ruthenium and Iridium Catalyzed Organic Transformations, Organic Process Research and Development, pp. 1156-1163, vol. 20, No. 7.

Terrill R.H., Hutchison J.E., Murray R.W. (1997)—Solid State Electron-Hopping Transport and Frozen Concentration Gradients in a Mixed Valent Viologen—Tetraethylene Oxide Copolymer, The Journal of Physical Chemistry B, pp. 1535-1542, vol. 101, No. 9.

Trabolsi A. et al. (2010)—Radically enhanced molecular recognition, Nature Chemistry, pp. 42-49, vol. 2, No. 1.

Wang M. et al. (2013)—Polymer nanocomposite hydrogels exhibiting both dynamic restructuring and unusual adhesive properties, Langmuir, pp. 7087-7095, vol. 29, No. 23.

Wang Q. et al. (2012)—Super-tough double-network hydrogels reinforced by covalently compositing with silica-nanoparticles, Soft Matter, pp. 6048-6056, vol. 8, No. 22.

Wojtecki R.J., Meador M.A., Rowan S.J. (2011)—Using the dynamic bond to access macroscopically responsive structurally dynamic polymers, Nature Materials, pp. 14-27, vol. 10, No. 1.

Xu H. et al. (2006)—Polymer actuator valves toward controlled drug delivery application, Biosensors and Bioelectronics, pp. 2094-2099, vol. 21, No. 11.

Yamaguchi H. et al. (2012)—Photoswitchable gel assembly based on molecular recognition, Nature Communications, pp. 603-605, vol. 3.

Yang J. et al. (2013)—Interaction of silica nanoparticle/polymer nanocomposite cluster network structure: revisiting the reinforcement mechanism, Journal of Physical Chemistry C, pp. 8223-8230, vol. 117, No. 16.

Yao F. et al. (2010)—Sliding-Graft Interpenetrating Polymer Networks from Simultaneous "Click Chemistry" and Atom Transfer Radical Polymerization, Macromolecules, pp. 9761-9770, vol. 43, No. 23.

Yu Q. et al. (2001)—Responsive biomimetic hydrogel valve for microfluidics, Applied Physics Letters, pp. 2589-2591, vol. 78, No. 17.

Yuan P. et al. (2017)—A programmable soft chemo-mechanical actuator exploiting a catalyzed photochemical water-oxidation reaction, Soft Matter, pp. 7312-7317, vol. 13, No. 40.

Zakharchenko S. et al. (2013)—Stimuli-responsive hierarchically self-assembled 3D porous polymer-based structures with aligned pores, Journal of Materials Chemistry B, pp. 1786-1793, vol. 1, No. 13.

Zhang S., Sha Q. (1993)—Electrical properties of the viologen-grafted poly(epichlorohydrin-coo-oxyethylene), Solid State Ionics, pp. 179-181, vol. 59.

Zhang S. et al. (2015)—A pH-responsive supramolecular polymer gel as an enteric elastomer for use in gastric devices, Nature Materials, pp. 1065-1071, vol. 14, No. 10.

Zhou C. et al. (2016)—Antibacterial poly(ethylene glycol) hydrogels from combined epoxy-amine and thiol-ene click reaction, Journal of Polymer Science, Part A: Polymer Chemistry, pp. 656-667, vol. 54, No. 5.

Zhu Z. et al. (2012)—Controlling switching in bistable [2]catenanes by combining donor-acceptor and radical-radical interactions, Journal of the American Chemical Society, pp. 11709-11720, vol. 134, No. 28.

\* cited by examiner

ACTUATING MATERIALS AND METHOD OF MAKING AND USING THE SAME

CROSS-REFERENCE TO RELATED APPLICATIONS

This application claims priority from U.S. Provisional Application Ser. No. 62/478,274 filed on 29 Mar. 2017 and U.S. Provisional Application Ser. No. 62/599,215 filed on 15 Dec. 2017, which are incorporated herein by reference in their entireties.

STATEMENT REGARDING FEDERALLY SPONSORED RESEARCH OR DEVELOPMENT

Not Applicable.

MATERIAL INCORPORATED-BY-REFERENCE

Not Applicable.

FIELD OF THE INVENTION

The present disclosure generally relates to compositions and methods for making and using actuating materials.

BACKGROUND OF THE INVENTION

One of the challenges in stimuli-responsive materials involves the design of macromolecular systems that can convert molecular motions initiated by external stimuli into useful macroscopic work. Although many different types of stimuli, such as temperature, changes in pH, redox switching, etc., have been investigated to induce movement in macroscopic objects, the use of light as an external source of energy is attractive since its versatility allows for spatial and temporal control over the actuation process. The most commonly used approach to program light responsiveness into materials involves the incorporation of azobenzene-containing polymers largely because the synthesis to prepare the photoresponsive switches is relatively straightforward and the trans-to-cis photoisomerization that occurs upon absorption of ultraviolet (UV) light is well known. Similarly, light-responsive olefin-based molecular motors undergo unidirectional motion when irradiated with UV light at room temperature. This property of unidirectional motion in a Feringa-type molecular motor was utilized elegantly by Giuseppone and co-workers to induce macroscopic contraction of a gel, and later contraction and expansion of a gel when combined with a visible-light absorbing modulator.

In the past decade, visible light photoredox catalysis has been shown to be a practical and useful strategy for carrying out small-molecule chemical transformations and controlled radical polymerizations.

SUMMARY OF THE INVENTION

Among the various aspects of the present disclosure is the provision of an actuating material. Specifically, the present disclosure provides for an actuating material comprising a photoredox-responsive material, a process of making the photoredox-responsive material, and methods of use thereof.

An aspect of the present disclosure provides for a composition comprising a photoredox-responsive material and a photocatalyst. In some embodiments, the photoredox-responsive material comprises a redox-active composition and the redox-active composition comprises a viologen.

In some embodiments, the composition comprises a polymer.

In some embodiments, the composition comprises a cross-linking component.

In some embodiments, the viologen is, reversibly, a reduced viologen ($V^{\cdot+}$), a neutral viologen ($V^0$), or an oxidized viologen ($V^{2+}$).

In some embodiments, the photocatalyst is a visible-light absorbing catalyst.

In some embodiments, the photocatalyst is selected from a ruthenium-based photocatalyst, ruthenium(II) trisbipyridine complex, or $Ru(bpy)_3Cl_2$.

In some embodiments, the polymer comprises: (i) a polyether, a polyurethane, a polyester, a polyamino acid, a polysaccharide, a bioerodible polymer, a vinyl polymer, natural polymer, an acrylate, or copolymers or combinations thereof; or (ii) a polyviologen, an acrylate, a vinyl, an alkyne-functionalized acrylate, a PEG, or a PAA, or copolymers or combination thereof.

In some embodiments, the cross-linking component is selected from a multi-armed cross-linker.

In some embodiments, the multi-armed cross-linker is selected from a $SiO_2$ nanoparticle (SNP), a viologen, or a tri- or tetra-alkyne cross-linker (TAXL).

In some embodiments, the photocatalyst is incorporated into the photoredox-responsive material as a free photocatalyst or covalently bound to the photoredox-responsive material as a functional group.

In some embodiments, upon exposure to light, the photoredox-responsive material comprises stacked viologen subunits and a contracted polymer network.

In some embodiments, the photoredox-responsive material is an actuating photoredox-responsive material.

Another aspect of the present disclosure provides for a method of producing a composition comprising a photoredox-responsive material. In some embodiments, the method comprises providing a redox-active composition comprising a viologen; providing a photocatalyst; introducing the redox-active composition comprising a viologen and the photocatalyst; or forming a solvated nanocomposite polymer network by cross-linking the redox-active composition.

In some embodiments, the composition is an actuating photoredox-responsive material.

In some embodiments, the photocatalyst is incorporated into the photoredox-responsive material as a free photocatalyst or covalently bound to the photoredox-responsive material as a functional group.

In some embodiments, the photoredox-responsive material comprises a polymer or a cross-linking component.

In some embodiments, the viologen is, reversibly, a reduced viologen ($V^{\cdot+}$), a neutral viologen ($V^0$), or an oxidized viologen ($V^{2+}$).

In some embodiments, the photocatalyst is a visible-light absorbing catalyst.

In some embodiments, the cross-linking component is selected from a multi-armed cross-linker.

In some embodiments, the photocatalyst is selected from a ruthenium-based photocatalyst, ruthenium(II) trisbipyridine complex, or $Ru(bpy)_3Cl_2$.

In some embodiments, the polymer comprises a polyether, a polyurethane, a polyester, a polyamino acid, a polysaccharide, a bioerodible polymer, a vinyl polymer, natural polymer, an acrylate, or copolymers or combinations thereof.

In some embodiments, the polymer comprises a polyviologen, an acrylate, a vinyl, an alkyne-functionalized acrylate, a PEG, or a PAA, or copolymers or combination thereof.

In some embodiments, the multi-armed cross-linker is selected from a $SiO_2$ nanoparticle (SNP), a viologen, or a tetra-alkyne cross-linker (TAXL).

In some embodiments, upon exposure to light, the photoredox-responsive material comprises stacked viologen subunits and a contracted polymer network.

In some embodiments, shining a light with a wavelength matching the wavelength of photocatalyst absorption (optionally, between about 450 nm and 490 nm) on the photoredox-responsive material, results in a stacking of viologen subunits and a contraction of the polymer network by photo-induced electron transfer (PET) from the photocatalyst to the viologen subunits.

In some embodiments, introduction of a sacrificial reductant results in a decrease in electrostatic repulsion, loss of corresponding counteranions, or an intramolecular folding of polyviologen chains.

In some embodiments, the photoredox-responsive material is in a contracted state when reduced and in an expanded state when oxidized.

In some embodiments, the photoredox-responsive material comprises the photoredox catalyst comprising $[Ru(bpy)_3]^{2+}$.

In some embodiments, the sacrificial reductant comprising triethanolamine (TEOA).

In some embodiments, the composition comprises about 80 mol % to about 100 mol % PEG.

In some embodiments, the composition comprises about 0 mol % to about 20 mol % polyviologen.

In some embodiments, the composition comprises a cross-linker selected from viologen, tetra-alkyne, or SNP.

An aspect of the present disclosure provides for a method of using a composition comprising an actuating photoredox-responsive material in a soft robotic; in a drug delivery device; in a light-activated transdermal patch; for the patterning of surfaces using light (e.g., photolithography); in a shape changing material; in an electrochromic material; in a redox flow battery; in a self-healing material; in a mechanical actuator; in a sensor; or in an artificial muscle.

In some embodiments, upon application or removal of an external stimulant, a rapid translation (e.g., seconds, minutes, or tens of minutes) of responses occurs at the (macro) molecular level.

In some embodiments, upon addition of oxygen and water, the material quickly (e.g., seconds, minutes, or tens of minutes) regains its original size and mechanical properties and optionally, recycled many times over.

In some embodiments, the composition is redox-responsive; the composition is flexible; the composition is three dimensional; the composition or material self-assembles; the composition is an actuating material; the composition is a stimuli-responsive material; the composition comprises an electrochromic hydrogel; or the composition comprises a ruthenium(II) trisbipyridine complex.

In some embodiments, the material responds to light. In some embodiments the response is reversible; the response is controlled chemically; the response occurs in seconds, minutes, or tens of minutes; the response reduces the material between about 1% and about 50% or between about 10% and about 20% of its original volume; the response comprises a contraction process; or the response results in about a 2.5-fold increase in elasticity of the composition.

In some embodiments, the material is submerged in a solvent (e.g., a solvent comprising water); or the material is introduced to $O_2$.

In some embodiments, introducing a light source to the material causes the material to contract (e.g., to <50% of its original size).

In some embodiments, the photoredox-responsive material has an inactivated state, a light-activated state, and an electrical- or chemical-activated state. In some embodiments, the photoredox material has a first color in the inactivated state; the photoredox material has a second color in the light-activated state; or the photoredox material has a third color in the electrically or chemically activated state.

In some embodiments, the oligo/poly-viologens possess n number of viologen subunits, wherein n=1, 2, 3, 4, 5, 6, 7, 8, 9, 10, 11, 12, 13, 14, 15, 16, 17, 18, 19, or 20.

In some embodiments, the composition comprises multivalent and cooperative non-covalent bonding interactions between oligomeric main-chain viologens in a cross-linked polyethylene glycol-silica nanoparticle network and a photocatalyst (e.g., ruthenium-bipyridine complexes) in the network allowing for photo-induced electron transfer (PET) from the photocatalyst (e.g., an organometallic complex) to the viologen subunits, thus generating a monocation radical oxidation state that leads to tight columnar-like packing on account of strong radical pairing between viologen subunits.

The composition or method of any one of the preceding claims wherein reversibility of the activated to inactivated state is performed in the absence of chemical reductants or oxidizers.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 1C is a space-filling representation of one of the $MV^{•+}$ stacks illustrates the tight packing resulting from favorable radical-radical pairing interactions.

FIG. 12A illustrates that, in this work, this redox-responsive hydrogel system was adapted to operate through a photoredox-based mechanism. In this case, irradiation with blue light triggers the actuation process and results in reversible contraction of a series of PEG-based hydrogels. FIG. 12B shows the mechanism of actuation relies on photoinduced electron transfer (PET) from an excited state ruthenium-based photocatalyst to the polyviologen chains in the network.

FIG. 14A is an image of the experimental setup for irradiating the polyviologen-containing hydrogels with blue light. The inset image reveals how the experiments were run simultaneously with three hydrogels at a time per glass jar. FIG. 14B is a graph showing contracted volume ratios (%) vs. Time (min) is plotted for experiments where three redox-responsive hydrogels at either 0, 1, 5, 10, or 20 mol % polyviologen concentration were irradiated with blue light for 5 h, with intermittent volume measurements taken as indicated by each data point.

FIG. 15A is an image of a polyviologen-containing hydrogel (5 mol %) swollen in "photoredox" solution at t=0 h. FIG. 15B is an image of the same gel at t=12 h after irradiation with blue light.

FIG. 19A is a graph showing the storage moduli (G) plotted against frequency (rad $s^{-1}$, with constant 1% strain amplitude) for each set of hydrogels with polyviologen molar concentrations ranging from 1, 5, 10, and 20 mol % of network chains. FIG. 19B is a graph showing the storage moduli (G') vs. contraction-expansion Cycle Number for a batch of 5 mol % $8V^{16+}$-containing hydrogels. The data points for each contraction-expansion cycle originate from the data points observed in the plots shown in part A), specifically at 10 rad $s^{-1}$.

FIG. 24A is an image of tape-backed gel with weight suspended in square-capped glass jar (with wet Kimwipe in bottom) positioned approximately 4 inches away from ~450 nm (blue) light source. FIG. 24B is an image of two square glass jars with disc gels being irradiated from top and bottom approximately 5 cm away from ~450 nm (blue) light source.

DETAILED DESCRIPTION OF THE INVENTION

Figures 1A, 1B:
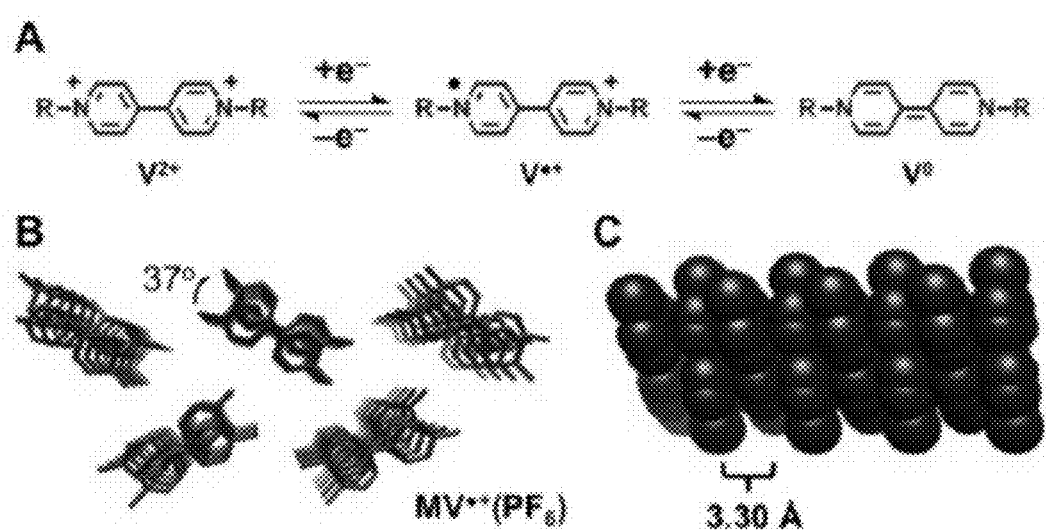
FIG. 1A is a scheme showing the redox processes of viologens are reversible.
FIG. 1B is a top-view of a stacked columnar array consisting of methyl viologens radical cations.

The present disclosure is based, at least in part, on the discovery that unimolecular oligomers and polymers comprised of redox-active subunits called viologens incorporated into a hydrogel respond reversibly to external stimuli. For example, the present disclosure provides for the development of a novel mode of actuation in a series of redox-responsive hydrogels doped with a visible-light-absorbing ruthenium-based photocatalyst. As shown herein, a synthetic protocol has been developed that enables the preparation of unimolecular oligomers and polymers comprised of redox-active subunits called viologens, and have incorporated these well-defined redox-active polymers into three-dimensional bulk materials referred to as hydrogels. These bulk materials are capable of responding reversibly to external stimuli (i.e., light, chemical reducing agents, and applied voltages that can activate the redox-active subunits or viologen subunits), such that the materials exhibit very large changes in shape, mass, and volume—where in most cases, the bulk material can contract to <50% of its original size.

In some embodiments, the photoredox-responsive material can exhibit changes in shape, mass, or volume, contracting to from between about 1% and 100% of its original size. For example, the photoredox-responsive material can contract to about 1%; about 2%; about 3%; about 4%; about 5%; about 6%; about 7%; about 8%; about 9%; about 10%; about 11%; about 12%; about 13%; about 14%; about 15%; about 16%; about 17%; about 18%; about 19%; about 20%; about 21%; about 22%; about 23%; about 24%; about 25%; about 26%; about 27%; about 28%; about 29%; about 30%; about 31%; about 32%; about 33%; about 34%; about 35%; about 36%; about 37%; about 38%; about 39%; about 40%; about 41%; about 42%; about 43%; about 44%; about 45%; about 46%; about 47%; about 48%; about 49%; about 50%; about 51%; about 52%; about 53%; about 54%; about 55%; about 56%; about 57%; about 58%; about 59%; about 60%; about 61%; about 62%; about 63%; about 64%; about 65%; about 66%; about 67%; about 68%; about 69%; about 70%; about 71%; about 72%; about 73%; about 74%; about 75%; about 76%; about 77%; about 78%; about 79%; about 80%; about 81%; about 82%; about 83%; about 84%; about 85%; about 86%; about 87%; about 88%; about 89%; about 90%; about 91%; about 92%; about 93%; about 94%; about 95%; about 96%; about 97%; about 98%; or about 99% of its original size. Recitation of each of these discrete values is understood to include ranges between each value. Recitation of each range is understood to include discrete values within the range.

Moreover, the redox-active viologen subunits are electrochromic, meaning when the system is activated and the bulk material shrinks, it also changes color when activated by light, chemical, or electricity (e.g., from yellow to black). Upon removal of the chemical stimulant and exposure to oxygen and water, the bulk material regains its original size and color. This process has been cycled approximately five times and little to no loss in reversibility has been observed. Lastly, when the redox process has been initiated, and the material reduces its size, it becomes more robust and its elasticity increases by nearly a factor of 2.5. Thus, when the material is activated, the mechanical strength of the shrunken material is dramatically improved when compared to the initial non-activated bulk material.

It is believed, this technology is the first example of a unimolecular viologen-containing oligomer/polymers that can possesses flexible, water-soluble linkers in between each of the redox-active viologen subunits. Furthermore, it is believed there are no reports of viologen oligomers/polymers incorporated into a bulk material and used as a means of inducing shape and color changes. Previous studies have shown examples where a hydrogel has been doped with small molecule viologens, which only change the material's color, but not its shape. One commercial example of this takes place in the new 747 airplanes, where the windows do not have pull-down shades, but rather they use methyl viologen-doped gels in between two glass panes and after a current is applied, the gel changes color (towards black) and the window visibility decreases. The present material can change color as well, but has the added benefit of changing the materials size, shape, and mechanical strength.

As shown herein, these redox-active polymers can be made and incorporated into hydrogels, which can be activated to contract either chemically, electrically, or by irradiation with light. The proprietary olio-/polymers are a first, as are the gels and demonstration of this type of a contraction-expansion process. Moreover, it is believed the degree with which these materials change shape and volume appears to be a record. Because of the above-stated properties, it is believed this material can be applied in applications such as in soft robotics, drug delivery in the form of light-activated transdermal patches, or patterning of surfaces using light (i.e., photolithography).

The rich redox chemistry of viologens (technically referred to as 4,4'-bipyridiniums) are well known, however, it is believed there are no examples, where anyone has (i) been able to make flexible, water-soluble, and unimolecular oligo-/poly-viologens capable of complete intramolecular collapse of the viologen-containing polymer; and (ii) incorporated oligo-poly-viologens into 3D bulk materials for the purposes of shape changing. In the enclosed literature and patent examples, it is evident that the main applications are electrochromic materials that cannot change shape, or redox flow batteries, which do not use main-chain viologen polymers capable of intramolecular collapse of the viologen-containing oligo-/polymer.

As shown herein, a protocol has been successfully developed that allows for the synthesis of viologen-based oligo-/poly-mers that possess n number of viologen subunits (e.g., where n=2, 4, 6, 8, or 10). The viologen-based oligo-/poly-mers were incorporated into 3D polymer networks called hydrogels. Upon chemical, electrochemical, or irradiation with visible light from an LED bulb, the hydrogel contracts to <50% of its original size and it changes colors (e.g., black for chemical, electrochemical reduction, or light-activation). The change in mechanical properties that occurs when the gel is contracted was also tested. A 2.5 increase in elasticity of the material was observed, which means it can stretch further without breaking and is mechanically stiffer, or more robust. It has also been demonstrated that this process is reversible as soon as the material is exposed to oxygen and water. This latter emphasis on oxygen and water can be important because the material can be contracted and then exposed to oxygen, which will oxidize it, but it will not expand until it soaks up water. This also implies that it could be useful as a shape memory material.

It is believed that these materials represent a first in terms of the design of the proprietary polymers/oligomers and the gels that contain them. These gels can be activated electrically, chemically, or by light. Applications can include soft robotics (especially if mixed with even stronger polymers used in rubbers rather than the current design which uses soft, biocompatible polyethylene glycol), drug delivery (e.g., nicotine patches that slowly reduce in size and release a drug molecule transdermally as light hits the back of a semi-opaque backing), and photolithography. For photolithography, thin films on wafers can be made and shine light through a photomask onto a surface, which would only activate certain portions of the film and thereby shrink only parts of the film that was exposed to light. This type of feature can be highly attractive in the electronics field for new ways to make patterns on surfaces.

Interest in the design and development of new stimuli-responsive materials has surged over the last few decades; typically with an eye towards creating self-healing materials and mechanical actuators that possess novel properties, but also more recently redox-flow batteries. The more commonly employed modes of inducing mechanical responses in a bulk material include i) electrochemical activation that initiates ion mobility between two electrodes, ii) controlling pH or temperature that results in electrostatic repulsion or entropically-driven desolvation, respectively, or iii) irradiation with light, which may isomerize an azobenzene-containing polymer, or initiate unidirectional rotation about an overcrowded olefin in a molecular motor. While the latter modes of action have been investigated in the context of hydrogels and thin films, there are certain factors that may limit performance and scalability—such as slow response times, synthetic complexity, and/or moderate 'returns' in the form of mass and volume changes after the chemical 'switch' has been activated.

Actuating Material

As described herein, is an actuating photoredox-active material was developed. As described here, a novel mode of actuation was discovered in a series of redox-responsive hydrogels doped with a visible-light-absorbing photocatalyst (e.g., ruthenium-based).

The present disclosure provides for actuating materials comprising hydrogels composed primarily of polyethylene glycol (PEG) and low molar concentrations of a unimolecular electroactive polyviologen that is activated through a PET mechanism. The rate and degree of contraction of the hydrogels were measured over several hours while irradiating with blue light. Likewise, the change in mechanical properties—determined through oscillatory shear rheology experiments—was assessed as a function of polyviologen concentration. Finally, an artificial molecular muscle was fabricated using the best-performing hydrogel composition, and its ability to perform work, while irradiated, was demonstrated by lifting a small weight (see e.g., Example 4).

As described herein, an actuating material (e.g., a responsive supramolecular material) was designed to respond at a (macro)molecular level upon application or removal of an external stimulant. For example, as shown herein, a radical-based self-assembly of viologen-based oligomer links, present at only 5 mol % within a 3D cross-linked network has been investigated, which allows for contraction of electrochromic hydrogels by effectively decreasing the mesh size in situ; a process which occurs within tens of minutes and results in a reduction of the bulk material to 10-20% of its original volume, whilst remaining submerged in water. This contraction process is controlled chemically, and can lead to a 2.5-fold increase in elasticity of the material. Upon addition of oxygen and water, the gels quickly regain their original size and mechanical properties and can be recycled many times over.

In some embodiments, the contracted photoredox-responsive material can have an increase in elasticity compared to the inactivated photoredox-responsive material. For example, the photoredox-responsive material can have an increase in elasticity of about 1×, about 2×; about 3×; about 4×; about 5×; about 6×; about 7×; about 8×; about 9×; about 10×, about 11×; about 12×; about 13×; about 14×; about 15×; about 16×; about 17×; about 18×; about 19×; about 20×; about 21×; about 22×; about 23×; about 24×; about 25×; about 26×; about 27×; about 28×; about 29×; about 30×; about 31×; about 32×; about 33×; about 34×; about 35×; about 36×; about 37×; about 38×; about 39×; about 40×; about 41×; about 42×; about 43×; about 44×; about 45×; about 46×; about 47×; about 48×; about 49×; about 50×; about 51×; about 52×; about 53×; about 54×; about 55×; about 56×; about 57×; about 58×; about 59×; about 60×; about 61×; about 62×; about 63×; about 64×; about 65×; about 66×; about 67×; about 68×; about 69×; about 70×; about 71×; about 72×; about 73×; about 74×; about 75×;

about 76×; about 77×; about 78×; about 79×; about 80×; about 81×; about 82×; about 83×; about 84×; about 85×; about 86×; about 87×; about 88×; about 89×; about 90×; about 91×; about 92×; about 93×; about 94×; about 95×; about 96×; about 97×; about 98×; about 99×; or about 100× that of the inactivated photoredox-responsive material.

A substantial challenge in the area of stimuli-responsive materials, that has been overcome by the disclosed discovery, is the rapid translation of responses that occur at the (macro)molecular level—upon application or removal of an external stimulant—up to the bulk scale, while simultaneously maintaining suitable performance metrics, such as the degree and reversibility of the actuation process. Furthermore, the actuatable technology should be scalable and operationally straightforward, methods of which have been described herein.

Responsive supramolecular materials that can be actuated reversibly by numerous external stimuli can typically rely on non-covalent bonding interactions—usually of the host-guest variety—that function as the "glue" which holds the individual components of a network together. These interactions allow for materials that can respond to changes in pH, temperature, and light, to name a few, and in some cases imbue the material with the ability to heal itself through cyclical dissociative/associative mechanisms of action that effectively enatures/rebuilds the crosslinking junctions in the network. Although this dynamic design strategy has been demonstrated in a number of systems, the overall degree with which the material can change at the macroscopic level is limited on account of the distance associated with each non-covalent bonding interaction.

Hydrogels are capable of undergoing large changes in shape and volume, a process which is largely driven by solvation during swelling experiments and ultimately stretches the cross-linked polymer chains until a maximum network size is achieved.

Described herein are light- and redox-responsive (photoredox-responsive) nanocomposite hydrogels. A novel strategy is discussed that aims to investigate these fundamental processes by actively controlling the network chain lengths through multivalent and cooperative non-covalent bonding interactions between oligomeric main-chain viologens in a cross-linked polyethylene glycol-silica nanoparticle network. Also described herein are oligomeric viologens cross-linked with viologens, optionally with additional polymers for desirable characteristics, such as strength and durability. Incorporation of ruthenium-bipyridine complexes in the network allowed for photo-induced electron transfer from the organometallic complex to the viologen subunits, thus generating their monocation radical oxidation states that lead to tight columnar-like packing on account of strong radical pairing between viologen subunits.

Nature typically relies on non-covalent bonding to control important biological processes. Typically, these types of through-space bonding interactions are presented using a biomacromolecular platform that allows for greater complexity in structure and scale—albeit beginning from relatively simple and discrete monomer libraries. Chemists have long sought to emulate nature's ability to control hierarchical self-assembly by employing synthetic, non-natural building blocks; however, a comprehensive knowledge of how to translate individual recognition events to the bulk scale, and do so in a controllable manner, has been a formidable challenge.

In some embodiments, an actuating material can utilize visible-light-absorbing photoredox catalysts. For example, a photocatalyst (e.g., ruthenium-bipyridine complexes) in the network can allow for photo-induced electron transfer from the organometallic complex to the viologen subunits. As another example, a visible-light-triggered contraction of a gel by can be capitalized on the plasmon resonance of Ag nanoparticles deposited on a semiconducting $TiO_2$ photocatalyst. For example, irradiating with visible light can result in the oxidation of Ag to $Ag^+$, and the hydrogel (e.g., a poly(acrylic acid) (PAA) gel network) can contract as the dangling carboxylate groups chelate the freed $Ag^+$.

The present disclosure provides for photoredox-based actuating materials. As described herein, a photoredox-responsive material includes redox-responsive materials that are catalyzed by a photocatalyst. Although interest in photoredox catalysis has risen exponentially in the past decade, there few examples where photoinduced electron transfer (PET) processes have been employed to actuate materials. Here, a ruthenium-based photoredox catalyst is described (see e.g., Example 4).

Figure 8:
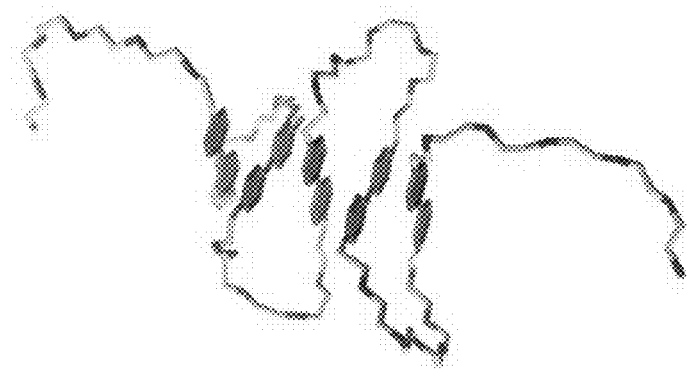
FIG. 8 is a series of images showing non-covalent bonding in macromolecular systems.

As described herein, redox-active units in the context of precise polymer networks are explored, providing a greater fundamental understanding of self-assembly in complex materials. By capitalizing on the reversible redox chemistry of 4,4'-bipyridiniums (i.e., viologens), the degree of bulk actuation of a material can be investigated and correlated to the concentration of radical-radical pairing interactions that are present in the network, as well as to the degree of molecular motion during the formation of each radical domain. An example of non-covalent bonding in macromolecular systems is shown in FIG. 8.

Figures 12A, 12B:
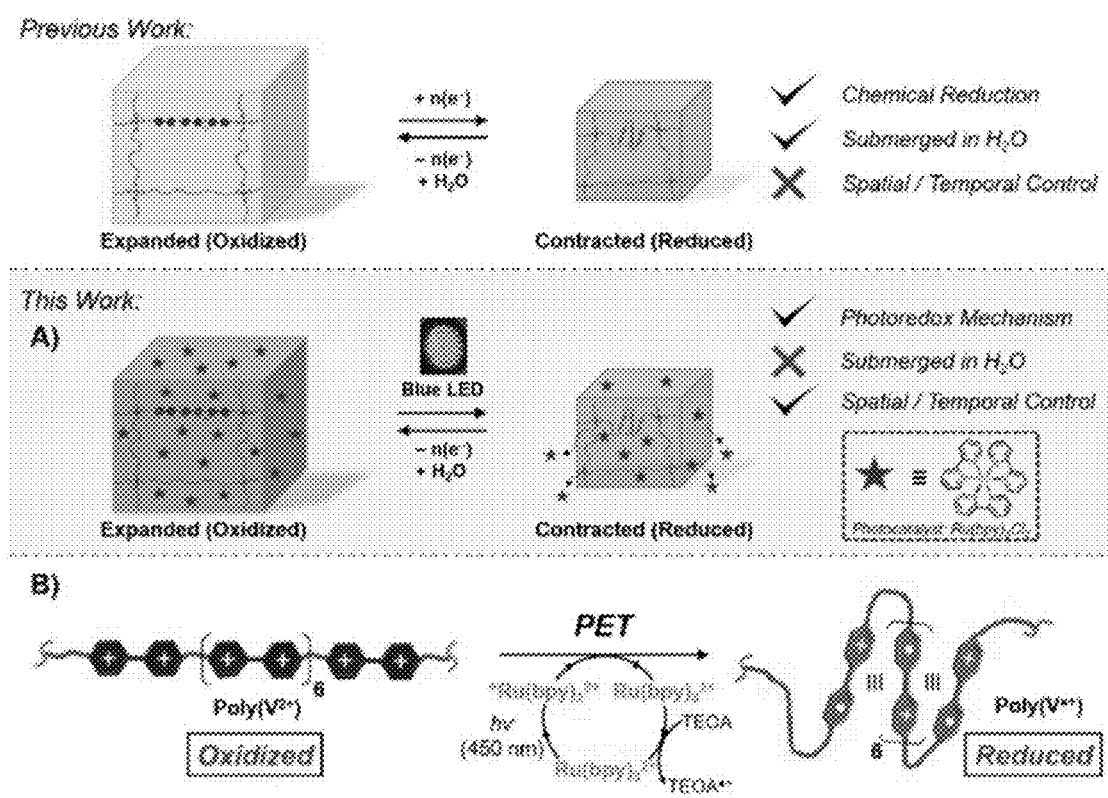
FIG. 12A-FIG. 12B is a series of illustrations depicting the general concept for light-triggered contraction and expansion of a hydrogel. It was demonstrated that polyviologens incorporated into a three-dimensional polymer network could be reduced chemically resulting in large degrees of actuation of a PEG-based hydrogel.

The inventors showed a redox-responsive hydrogel system (see e.g., FIG. 5C, FIG. 12) that was prepared via copper-mediated 'click' chemistry and composed of poly (ethylene glycol) (PEG), a low molar amount of electroactive and unimolecular oligoviologens of different lengths, and a tetra-alkyne crosslinker. Actuation of this redox-responsive hydrogel was achieved by submerging it in an aqueous 1 M $Na_2S_2O_4$ solution that reduced each viologen subunit to the corresponding radical cation (i.e., $V^{2+}$ to $V^{\cdot+}$), a process which resulted in a decrease in electrostatic repulsion, a loss of counteranions, and intramolecular self-assembly, or chain folding, of the integrated oligoviologen chains. This actuation mechanism ultimately led to relatively fast contraction of the hydrogel to 35% of its original volume in the first 25 min, and 9% after several hours. Expansion of the reduced hydrogels was achieved in this case by soaking them in $O_2$-saturated $H_2O$, and reversibility was demonstrated over multiple contraction-expansion cycles. Although an effective method for quickly actuating hydrogels, the present disclosure provides for control over the actuation process without having to submerge the hydrogel in a solution containing chemical reductants or oxidizers.

As described herein, an actuating material can be a light-responsive actuating material. The use of light to actuate materials can be advantageous because it represents a cost-effective and operationally straightforward way to introduce energy into a stimuli-responsive system. Common strategies for photoinduced actuation of materials typically rely on light irradiation to isomerize azobenzene derivatives or induce unidirectional rotation of molecular motors incorporated into a three-dimensional polymer network. The present disclosure provides for a photocatalyst (e.g., a ruthenium-bipyridine complex) allowing for photo-induced electron transfer from the organometallic complex to the viologen subunits, thus generating their monocation radical oxidation states that lead to tight columnar-like packing on account of strong radical pairing between viologen subunits.

Photocatalyst

The present disclosure provides for an actuating material catalyzed with a visible-light-absorbing photocatalyst. The photocatalyst can be any photocatalyst capable of catalyzing the redox reaction. As an example, the photocatalyst can be an organometallic complex. For example, the photocatalyst can be a ruthenium-based photocatalyst, such as a ruthenium-bipyridine complex (e.g., tris(bipyridine)-ruthenium (II) ([Ru(bpy)$_3$])). As another example, the photocatalyst can be an iridium-based catalyst.

The photocatalyst can be any visible-light absorbing catalyst used in established photoredox chemistry. For example, the photocatalyst can be any photocatalyst known in the art (see e.g., Teegardin et al. 2016 Advances in Photocatalysis: A Microreview of Visible Light Mediated Ruthenium and Iridium Catalyzed Organic Transformations Org. Process Res. Dev., 2016, 20 (7), pp 1156-1163) that is a visible-light absorbing catalyst or can catalyze the redox reaction, as described herein.

The visible-light absorbing catalyst can catalyze the redox reaction when exposed to a wavelength between about 380 nm and 70 nm. For example, the visible-light absorbing catalyst can catalyze the redox reaction when exposed to a wavelength between about 380 nm and 450 nm (violet light); between about 450 nm and 495 nm (blue light); between about 495 nm and 570 nm (green light); between about 570 nm and 590 nm (yellow light); between about 590 nm and 620 nm (orange light); or between about 620 nm and 750 nm (red light).

Redox-Active Composition (e.g., Viologens)

The actuating materials as described herein utilize reversible redox chemistry (e.g., 4,4'-bipyridiniums (i.e., viologens)). A redox-active composition can be referred to as a redox active subunit (e.g., a viologen).

Viologens—or more specifically 4,4'- and 2,2'-dialkyl-bipyridiniums and derivatives thereof—are electro-active molecules whose redox chemistry was initially reported by Michaelis over 85 years ago. Since then, they have been used as bioassay indicators, herbicides, electrochromic materials in devices, redox mediators in energy storage applications, and as either 7-electron-deficient moieties or as a source of persistent or stable radicals, the latter of which can function as molecular recognition units that are used to template the synthesis of small-molecule and oligomeric mechanically interlocked molecules, such as catenanes and rotaxanes.

Viologens are well known in the art and are derivatives of

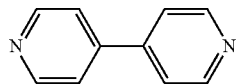 [SMILES: c1cc(-c2ccncc2)ccn1]

4,4'-bipyridniums and

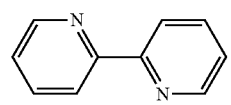

2,2'-bipyridiniums.

A viologen can be of the formula:

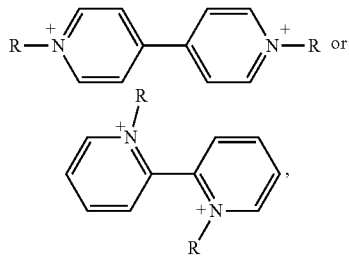

where R can be a substituted or unsubstituted $C_{1-10}$alkyl. For example, R can be H, Me, Et, Pr, Bu, $C_5H_{11}$, $C_6H_{13}$, $C_7H_{15}$, or $C_8H_{17}$.

Viologens are well-known in the art and can be of any formula suitable for use in an actuating material (see e.g., Bird and Kuhn 1981 Electrochemistry of the viologens, Chem Soc Rev. 10 49-82).

Viologens can be used for electrochromic systems because of their ability to change color reversibly many times upon reduction and oxidation.

In extended viologens, conjugated oligomers such as those based on aryl, ethylene, or thiophene units can be inserted between the pyridine units. A bipolaron di-octyl bis(4-pyridyl)biphenyl viologen can be reduced to a neutral viologen.

In some embodiments, the actuating material can comprise an oligo/poly-viologen of the formula nV. For example, the oligo/poly-viologen of formula nV can have an n value between 1 and 100 or more preferably, between 1 and 20. For example, n can be an even number between 1 and 100, or n can be 1; 2; 3; 4; 5; 6; 7; 8; 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100. Recitation of each of these discrete values is understood to include ranges between each value. Recitation of each range is understood to include discrete values within the range.

In some embodiments, the precursor to the actuating material can comprise a tosyl group (e.g., a tosyl capped viologen). As described herein, the majority of the counterions make up the total number of tosylates that are present in the polymer, whereas the two end-capping leaving groups are replaced by more bipyridine units as the synthesis of the polymer progresses. For example, the viologen or oligo/poly-viologen can comprise about 1 to about 50 Tosyl (Tos) leaving groups or counterions. As another example, the viologen or oligo/poly-viologen can comprise 1 Tos; 2 Tos; 3 Tos; 4 Tos; 5 Tos; 6 Tos; 7 Tos; 8 Tos; 9 Tos; 10 Tos; 11 Tos; 12 Tos; 13 Tos; 14 Tos; 15 Tos; 16 Tos; 17 Tos; 18 Tos; 19 Tos; 20 Tos; 21 Tos; 22 Tos; 23 Tos; 24 Tos; 25 Tos; 26 Tos; 27 Tos; 28 Tos; 29 Tos; 30 Tos; 31 Tos; 32 Tos; 33 Tos; 34 Tos; 35 Tos; 36 Tos; 37 Tos; 38 Tos; 39 Tos; 40 Tos; 41 Tos; 42 Tos; 43 Tos; 44 Tos; 45 Tos; 46 Tos; 47 Tos; 48 Tos; 49 Tos; 50 Tos; 51 Tos; 52 Tos; 53 Tos; 54 Tos; 55 Tos; 56 Tos; 57 Tos; 58 Tos; 59 Tos; 60 Tos; 61 Tos; 62 Tos; 63 Tos; 64 Tos; 65 Tos; 66 Tos; 67 Tos; 68 Tos; 69 Tos; 70 Tos; 71 Tos; 72 Tos; 73 Tos; 74 Tos; 75 Tos; 76 Tos; 77 Tos; 78 Tos; 79 Tos; 80 Tos; 81 Tos; 82 Tos; 83 Tos; 84 Tos; 85 Tos; 86 Tos; 87 Tos; 88 Tos; 89 Tos; 90 Tos; 91 Tos; 92 Tos; 93 Tos; 94 Tos; 95 Tos; 96 Tos; 97 Tos; 98 Tos; 99 Tos; or 100 Tos.

Recitation of each of these discrete values is understood to include ranges between each value. Recitation of each range is understood to include discrete values within the range.

In some embodiments, the actuating material can comprise a concentration of a redox-active composition (e.g., oligo/poly-viologen) between about 1 mol % and about 100 mol %. For example, the redox-active composition (e.g., oligo/poly-viologen) can be at a concentration of about 1 mol %; about 2 mol %; about 3 mol %; about 4 mol %; about 5 mol %; about 6 mol %; about 7 mol %; about 8 mol %; about 9 mol %; about 10 mol %; about 11 mol %; about 12 mol %; about 13 mol %; about 14 mol %; about 15 mol %; about 16 mol %; about 17 mol %; about 18 mol %; about 19 mol %; about 20 mol %; about 21 mol %; about 22 mol %; about 23 mol %; about 24 mol %; about 25 mol %; about 26 mol %; about 27 mol %; about 28 mol %; about 29 mol %; about 30 mol %; about 31 mol %; about 32 mol %; about 33 mol %; about 34 mol %; about 35 mol %; about 36 mol %; about 37 mol %; about 38 mol %; about 39 mol %; about 40 mol %; about 41 mol %; about 42 mol %; about 43 mol %; about 44 mol %; about 45 mol %; about 46 mol %; about 47 mol %; about 48 mol %; about 49 mol %; about 50 mol %; about 51 mol %; about 52 mol %; about 53 mol %; about 54 mol %; about 55 mol %; about 56 mol %; about 57 mol %; about 58 mol %; about 59 mol %; about 60 mol %; about 61 mol %; about 62 mol %; about 63 mol %; about 64 mol %; about 65 mol %; about 66 mol %; about 67 mol %; about 68 mol %; about 69 mol %; about 70 mol %; about 71 mol %; about 72 mol %; about 73 mol %; about 74 mol %; about 75 mol %; about 76 mol %; about 77 mol %; about 78 mol %; about 79 mol %; about 80 mol %; about 81 mol %; about 82 mol %; about 83 mol %; about 84 mol %; about 85 mol %; about 86 mol %; about 87 mol %; about 88 mol %; about 89 mol %; about 90 mol %; about 91 mol %; about 92 mol %; about 93 mol %; about 94 mol %; about 95 mol %; about 96 mol %; about 97 mol %; about 98 mol %; about 99 mol %; or about 100 mol %. Recitation of each of these discrete values is understood to include ranges between each value. Recitation of each range is understood to include discrete values within the range.

Polymers

Any polymer suitable for use in the disclosed actuating materials can be used in combination with the oligomers and polymers comprised of redox-active subunits called viologens as described herein. The use of additional polymers can be used to produce a stronger or tougher material (see e.g., Example 5). For example, polymer-based actuators are materials that are capable of changing their shape in response to a variety of external stimuli—such as light, temperature, pH, moisture, chemicals, gases, and electric and magnetic fields. One of the key advantages of using polymers in actuators is the ability to target a particular physical or chemical stimulus-response (cause-effect) relationship through the careful molecular design of the monomer precursors. This level of chemical versatility opens up the door for a number of applications, where polymeric actuators have been used in biomedical engineering, drug delivery, sensors, electronics, microfluidics, artificial muscles, and microfabrication, to name a few. Within the field of polymer-based actuators, there are several classes of materials that are able to work in different environments and possess disparate levels of elasticity and mechanical robustness, ultimately resulting in differing modes of actuation.

As an example, the polymer can be used as a linker between oligo/poly-viologens or as a linker between a cross-linking group (e.g., SNP) and other crosslinking groups or oligo/poly-viologens.

Stronger polymers such as those used in robotics, can be utilized in the actuating material such as polymers used in rubbers.

For example, a biocompatible polymer (e.g., bioabsorbable/biodissolvable/meltable/biodegradable/bioerrodable polymer) can be used. As an example, a biocompatible polymer can be a:

(i) polyether (e.g., polyethylene glycol (PEG), high molecular weight PEG is PEG3350, low molecular weight PEG is PEG400, PEG can be, for example, polyethylene oxide (PEO) or polyoxyethylene (POE), poly(ethylene glycol) (PEG), poly(propylene glycol) (PPG), poly(tetrahydrofuran), hexaethylene glycol (HEG), triethylene glycol (TEG));

(ii) polyurethane (iii) polyester (e.g., polycaprolactone (PCL), polylactide or polylactic acid (PLA), polyglycolide or polyglycolic acid (PGA), poly(lactide-glycolide) (PLGA), poly(propylene fumarate) (PPF), poly(caprolactone fumarate) (PCLF), poly(glycolide-co-caprolactone) (PGCL), poly(L-lactic acid) (PLLA), poly(D-lactic acid) (PDLA), poly(D,L-lactic acid) (PDLLA)—a racemic mixture of PLLA and PDLA, polyortho ester, polyhydroxobutyrate (PHB), meso-poly(lactic acid));

(iv) polyamino acid (e.g., poly(γ-glutamic acid) (γ-PGA) and poly(L-lysine), poly(L-glutamic acid) (L-PGA) and poly(aspartic acid)(PAA));

(v) polysaccharide (e.g., hyaluronic acid (HA), chitin, alginate, chitosan);

(vi) bioerodible polymer (e.g., polyphosphazenes (bulk or surface erosion); polyanhydrides (surface erosion));

(vii) vinyl polymer (e.g., polyethylene vinyl acetate (PEVA), polyvinylpyrrolidone (PVP)); or (viii) natural polymer (e.g., elastin & elastin-like polypeptides, albumin, fibrin, collagen, fibronectin);

(ix) acrylate (comprising a vinyl group and a carboxylic add terminus) (e.g., acrylics or polyacrylates such as methacrylates, methyl acrylate, methyl methacrylate (MMA), ethyl acrylate, 2-chloroethyl vinyl ether, 2-ethylhexyl acrylate, hydroxyethyl methacrylate, butyl acrylate, butyl methacrylate, TMPTA, polymethyl methacrylate, PVAc, polyacrylarnide), or (x) copolymers or combinations thereof.

In some embodiments, the actuating material can comprise a concentration of a polymer (e.g., PEG) between about 1 mol % and about 100 mol %. For example, the polymer can be at a concentration of about 1 mol %; about 2 mol %; about 3 mol %; about 4 mol %; about 5 mol %; about 6 mol %; about 7 mol %; about 8 mol %; about 9 mol %; about 10 mol %; about 11 mol %; about 12 mol %; about 13 mol %; about 14 mol %; about 15 mol %; about 16 mol %; about 17 mol %; about 18 mol %; about 19 mol %; about 20 mol %; about 21 mol %; about 22 mol %; about 23 mol %; about 24 mol %; about 25 mol %; about 26 mol %; about 27 mol %; about 28 mol %; about 29 mol %; about 30 mol %; about 31 mol %; about 32 mol %; about 33 mol %; about 34 mol %; about 35 mol %; about 36 mol %; about 37 mol %; about 38 mol %; about 39 mol %; about 40 mol %; about 41 mol %; about 42 mol %; about 43 mol %; about 44 mol %; about 45 mol %; about 46 mol %; about 47 mol %; about 48 mol %; about 49 mol %; about 50 mol %; about 51 mol %; about 52 mol %; about 53 mol %; about 54 mol %; about 55 mol %; about 56 mol %; about 57 mol %; about 58 mol %; about 59 mol %; about 60 mol %; about 61 mol %; about 62 mol %; about 63 mol %; about 64 mol %; about 65 mol %; about 66 mol %; about 67 mol %; about 68 mol %; about 69 mol %; about 70 mol %; about 71 mol %; about 72 mol %; about 73 mol %; about 74 mol %; about 75 mol %; about 76 mol %; about 77 mol %; about 78 mol %; about 79 mol %; about 80 mol %; about 81 mol %; about 82 mol %; about 83 mol %; about 84 mol %; about 85 mol %; about 86 mol %; about 87 mol %; about 88 mol %; about 89 mol %; about 90 mol %; about 91 mol %; about 92 mol %; about 93 mol %; about 94 mol %; about 95 mol %; about 96 mol %; about 97 mol %; about 98 mol %; about 99 mol %; or about 100 mol %. Recitation of each of these discrete values is understood to include ranges between each value. Recitation of each range is understood to include discrete values within the range.

Cross-Linking Component

The actuating material as described herein can comprise a cross-linking component.

The cross-linking component can comprise a cross-linking group. The cross-linking component or cross-linking group can be used to link cross-linking groups to other cross-linking groups; link cross-linking groups to redox-active compositions (e.g., oligo/poly-viologens); or link redox-active compositions to other redox-active compositions.

The cross-linking component can be a multi-armed cross-linking component. For example, the multi-armed cross-linking component can be a viologen, a polyviologen, an oligoviologen, a nanoparticle, a SiO₂ nanoparticle (SNP), or tri- and tetra-alkyne cross-linkers (TAXLs).

For example, a viologen cross-linker is described in Example 5. Viologen cross linkers can comprise

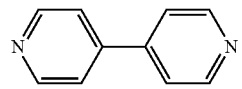 [SMILES: c1cc(-c2ccncc2)ccn1]

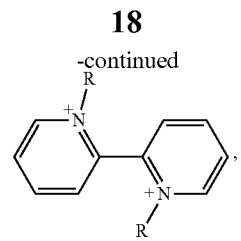

where R can be

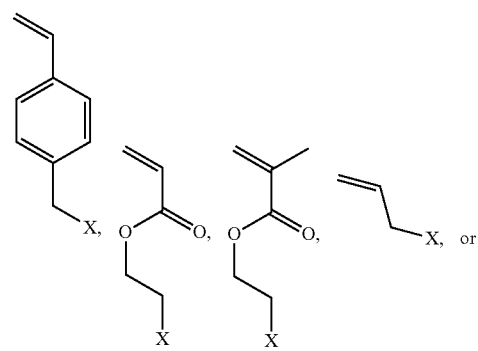

The viologen cross-linker can be of the formula:

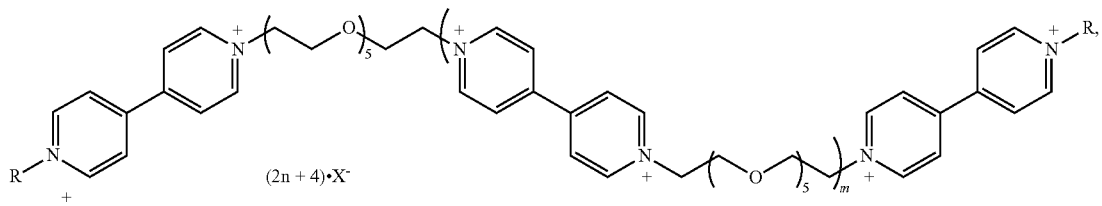

4,4'-bipyridniums and

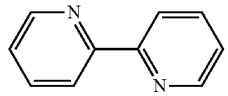

2,2'-bipyridiniums and derivatives thereof.

A viologen cross-linker can comprise:

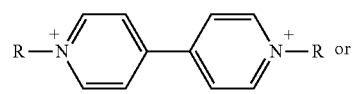

where R can be

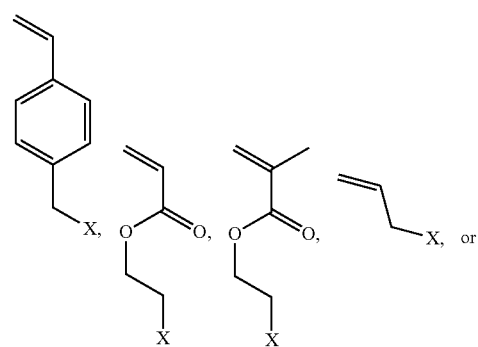

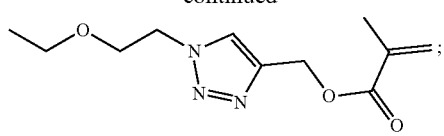

X can be: Cl, Br, I, or OTos;

M can be

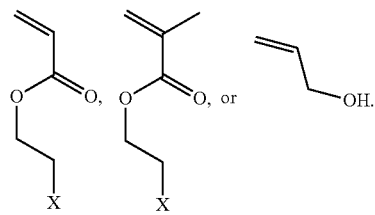

The 3D polymer network can be of the formula:

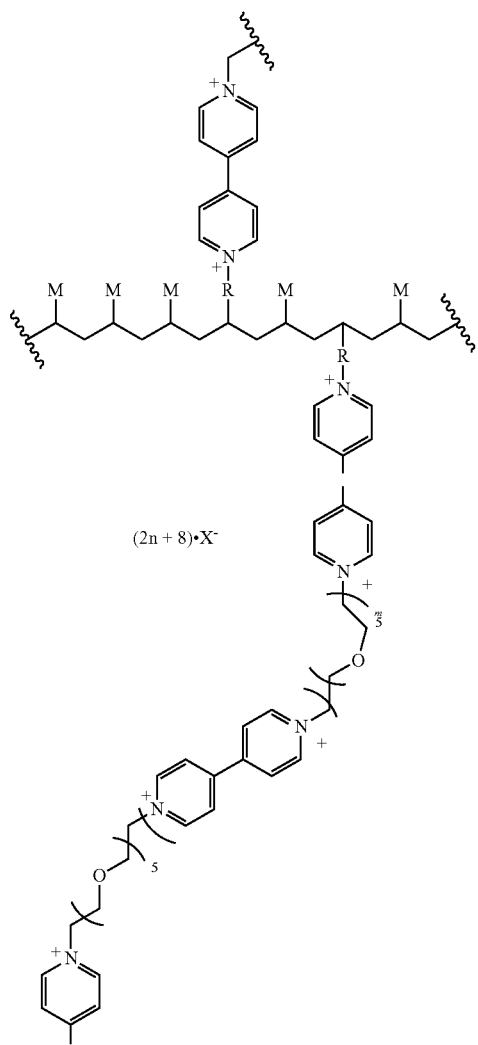

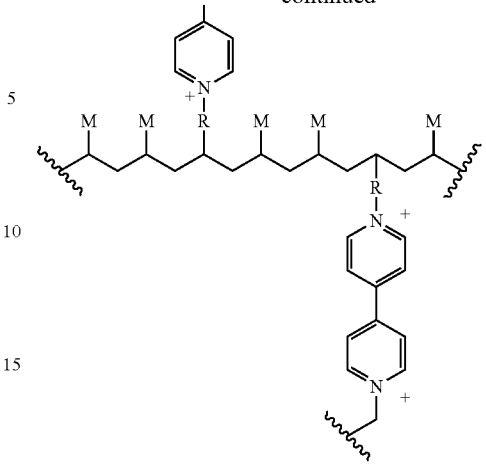

wherein R and M are as described above.

The cross-linking component can be any component capable of linking polymers and redox-active groups. For example, the polyviologen can be a cross-linker (see e.g., Example 5 describing polyacrylate-based 3D polymer networks, where the polyviologen serves as the crosslinker). The cross-linker can also be any cross-linker suitable for use in hydrogel systems. For example, cross-linkers described in U.S. Pat. Nos. 8,192,485 and 8,877,227 can be used for such purposes and are incorporated by reference in their entirety. As another example, the linker can comprise a poly(ethylene glycol) (PEG) derivative. As another example, the linker can comprise PEG, TA-PEG-Maleimide, TA-PEG-OMe, or TA-PEG. As another example, a linker can comprise an isothiocyanate group, a carboxylic acid or carboxylate groups, a dendrimer, a dendron, Fmoc-protected-2,3-diaminopropanoic acid, ascorbic acid, a silane linker, minopropyltrimethoxysilane (APTMS), or dopamine. Other covalent coupling methods can employ the use of 2 thiol groups, 2 primary amines, a carboxylic acid and primary amine, maleimide and thiol, hydrazide and aldehyde, or a primary amine and aldehyde. For example, the linker can be an amide, a thioether, a disulfide, an acetyl-hydrazone group, a polycyclic group, a click chemistry (CC) group (e.g., cycloadditions, for example, Huisgen catalytic cycloaddition; nucleophilic substitution chemistry, for example, ring opening of heterocyclic electrophiles; carbonyl chemistry of the "nonaldol" type, for example, formation of ureas, thioureas, and hydrazones; additions to carbon-carbon multiple bonds, for example, epoxidation and dihydroxylation); or a physical or chemical bond.

The cross-linking component can be a nanoparticle. Nanoparticles can be combined with a polymeric network to obtain nanocomposite hydrogels. For example, the nanoparticle can be an inorganic nanoparticle, such as a $SiO_2$ nanoparticle. As another example, the nanoparticle can be biodegradable polymeric nanoparticles, polymeric micelles, solid nanoparticles, lipid-based nanoparticles, e.g., Solid lipid nanoparticles (SLN), nanostructured lipid carriers (NLC) and lipid drug conjugate (LDC), nanoliposomes, inorganic nanoparticles, dendrimers, magnetic nanoparticles, Ferrofluids, or quantum dots. An example of inorganic nanoparticles can comprise hydroxyapatite, silica, silicates, or calcium phosphate. As another example, the nanoparticle can comprise carbon-based nanomaterials (e.g., carbon nanotubes (CNTs), graphene, nano diamonds), polymeric nanoparticles (e.g., polymer nanoparticles, dendrimers, hyperbranched polyesters), inorganic/ceramic nanoparticles (e.g., hydroxyapatite, silica, silicates, calcium phosphate), or metal/metal-oxide nanoparticles (e.g., gold, silver, iron-oxide).

The cross-linking component can also be a small-molecule linking group such as tri- or tetra-alkyne cross-linker (TAXL).

Hydrogels

As described herein, any hydrogel suitable for use in an actuating material can be used.

Methods of making and choosing appropriate hydrogel systems are well known; see e.g. Ahmed 2015 J Adv Res. 6(2) 105-121; Calo 2015 Eur Poly J. 65 252-267. Except as otherwise noted herein, therefore, the process of the present disclosure can be carried out in accordance with such processes.

Compositions and methods as described herein can use hydrogels. Hydrogels can be capable of exhibiting a large degree of actuation because they consist largely of water and function through solvation/desolvation pathways of a three dimensional (3D) crosslinked polymer network. As an example, nanocomposite hydrogels are constructed using inorganic nanoparticles in combination with a polymer network to afford tensile strengths that are orders of magnitude greater than the singular polymer network alone, whilst still retaining a large percentage of the original elasticity. The combination of a nanocomposite design with a structurally versatile stimuli-responsive polymer network comprised of dynamic bonds (either covalent or non-covalent) results in adaptive supramolecular materials that undergo a reorganization of the polymer structure in response to a particular stimulus. The last few decades have seen an explosion of interest in the implementation of supramolecular chemistry motifs in a wide variety of supramolecular polymers. These polymers capitalize on the equilibria associated with non-covalent bonding interactions—e.g., metal-ligand coordination, hydrogen bonding, π-π stacking, etc.—between molecular recognition units in order to adapt to changes in the local environment and thus possess actuation processes that are reversible. Although there are many recognition motifs that have been investigated in polymers, there are only a few examples which capitalize on the donor-acceptor molecular recognition of petroleum-derived viologens ($V^{2+}$), and even fewer that take advantage of the facile redox chemistry of viologens (see e.g., FIG. 1A), the latter of which allows for self-recognition (see e.g., FIG. 1B) through strong (in some cases $K_a > 10^6$-$10^7 M^{-1}$ in water) radical-radical spin pairing interactions. In fact, most examples that explore viologen redox processes do so for the purpose of developing electrochromic/conducting materials or redox mediators, whereas in only a few cases the viologens are (electro) chemically reduced as a means toward radical-based actuation. In all of these cases, however, the actuation takes place on small molecules (i.e., rotaxanes and catenanes) or on the surface of non-cross-linked porous particles. What is lacking is an investigation into whether or not a multivalent supramolecular strategy—which capitalizes on electrochromic switching between a reduced state ($V^{\bullet +}$) possessing many strong viologen radical pairing interactions to an oxidized one ($V^{2+}$) comprised of repulsive electrostatic interactions—is capable of rapid and reversible changes in network chain lengths that lead to macroscopic shape changes in a bulk 3D material.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Figures 2A, 2B:
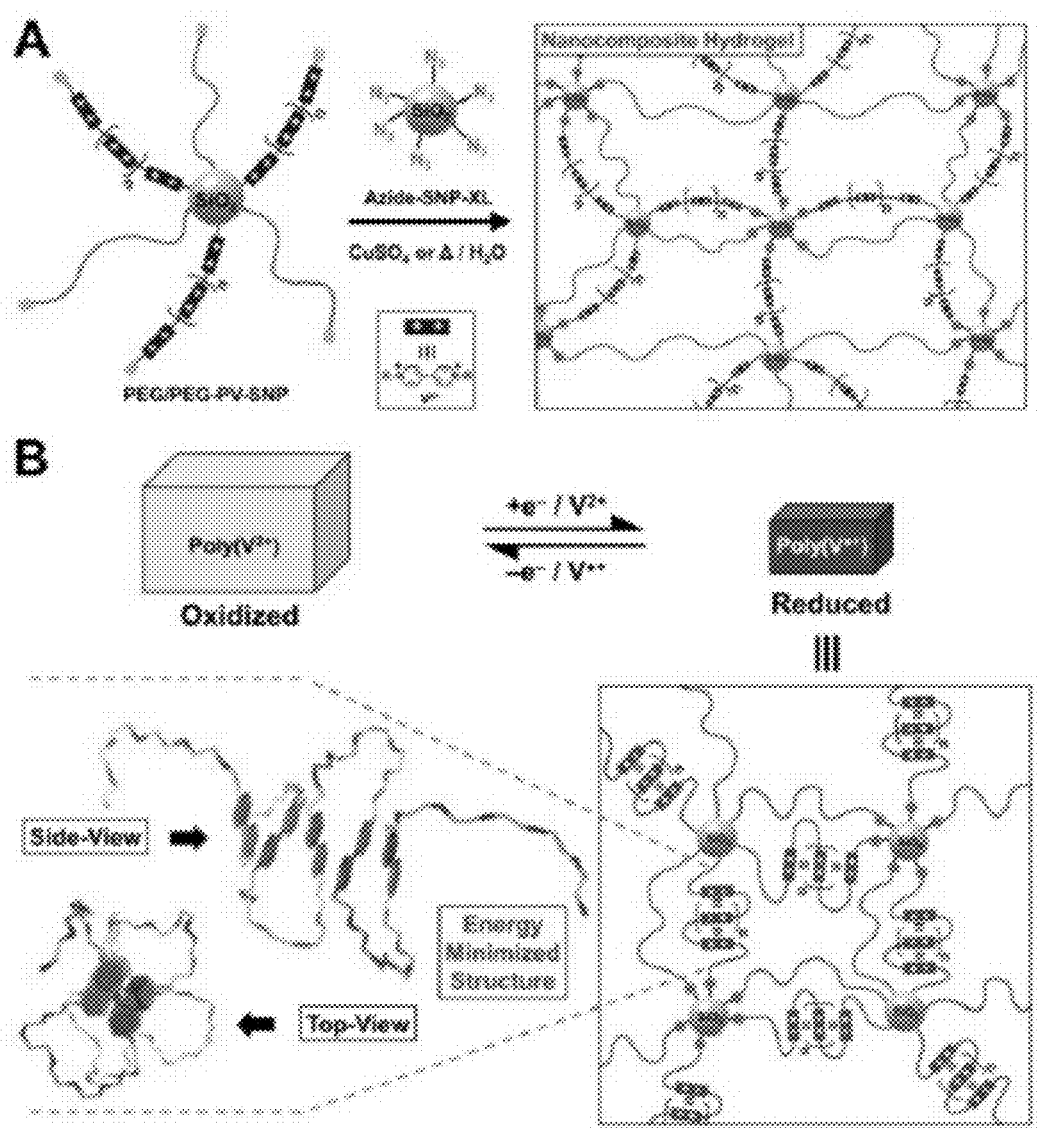
FIG. 2A is a schematic showing that cross-linking the PEG-PEG-PV SNP with Azide-SNP-XL results in the formation of a solvated nanocomposite polymer network.
FIG. 2B is a schematic showing a single electron reduction of each viologen subunit ($V^{2+}$) to its corresponding monoradical ($V^{•+}$) results in a contraction of the bulk material, and the expulsion of water. The enlarged inset of part (B) shows an energy minimized structure (side- and top-views) consisting of a 5-unit containing PEG-PV polymer, where the $V^{•+}$ subunits form a tightly packed columnar domain.
Figures 3A, 3B, 3C:
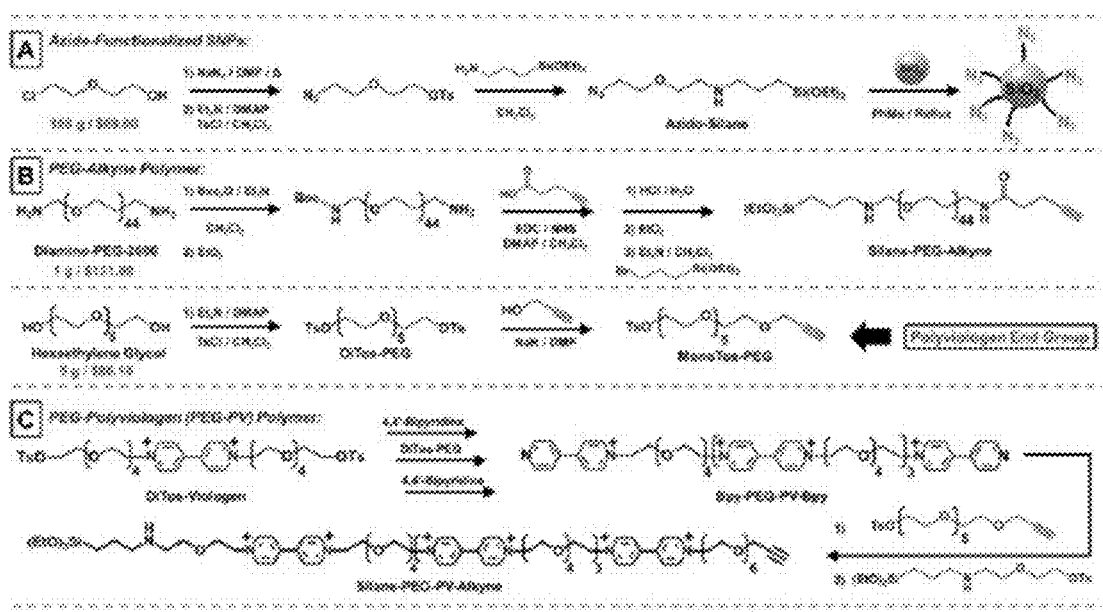
FIG. 3A is a scheme showing the synthesis of the Azido-Silane compound can be achieved in three steps, followed by grafting it onto the surface of the SNPs using standard condensation chemistry.
FIG. 3B is a scheme showing the synthesis of the Silane-PEGAlkyne is carried out in three steps using commercially available Diamino-PEG-2000 (~44 ethylene glycol units). The alkyne end group for the polyviologen (PV) can be synthesized in only two steps from hexaethylene glycol.
FIG. 3C is a scheme showing the PEG-PV polymer is synthesized through successive quaternization reactions of the nitrogen atom of 4,4'-bipyridine, generating each $V^{2+}$ subunit, followed by precipitation in $Et_2O$ (i.e., little to no chromatography).

Example 1: Developing Redox-Responsive Polyviologen-Silica Nanocomposite Hydrogels The modular design of the nanocomposite hydrogel network (see e.g., FIG. 2) can be modified/tuned to fit a desired application by adapting three key areas: i) the size (down to small silsesquioxane cages) and porosity of the silica nanoparticles (SNPs), ii) the concentration of poly(ethylene glycol) (PEG) and PEG-based polyviologen (PEG-PV) chains, as well as the number of $V^{2+}$ subunits per chain, and iii) the size, type, and concentration of the azide-functionalized cross-linker (e.g., Azide-SNP-XL). At the start, it was proposed to use the standard Stöber protocol to synthesize ~100 nm sized SNPs as the hard domain cross-linking junctions, and primarily focus on the concentration of $V^{2+}$ subunits present in the hydrogel network in order to establish the number of $V^{\cdot+}$-$V^{\cdot+}$ interactions needed to obtain the greatest macroscopic actuation—defined by the greatest change in total volume of the hydrogel. The cross-linking step (see e.g., FIG. 2A) can be carried out in a 1:1 mixture of water:tert-butanol ($H_2O$:tBuOH) by either using copper reagents to undergo efficient and regioselective copper-catalyzed azide-alkyne cycloaddition (CuAAC)—i.e., "click" chemistry—to generate 1,4-triazole linkers. The synthesis (see e.g., FIG. 3A-FIG. 3C) of the polymer chains is rather straight-forward, such that more or less $V^{2+}$ subunits can be achieved in only a few reaction steps, followed by immobilization of the polymers on the surface of the nanoparticles through standard silane condensation reactions (see e.g., FIG. 3A) at elevated temperatures. Characterization of the initial actuation process that takes place on the surface of the functionalized SNPs can be carried out before the cross-linking step by carrying out dynamic light scattering (DLS) measurements. The degree of radical-radical pairing interactions can be monitored by measuring the change in light scattering intensity as the nanoparticles become slightly smaller. Since DLS is a sensitive method of detecting small structural changes in materials, it will be a suitable characterization technique to confirm actuation. Once the network is formed via the "click" reaction step that cross-links the functionalized SNPs, the physical properties of the material—namely, the stress-strain curve, the corresponding Young's modulus, and tensile strength—will be measured using a Universal Testing Machine. Additionally, the storage and loss moduli (G' and G", respectively) can be measured using an oscillatory shear rheometer. Based on the desired application for the nanocomposite hydrogel material, the elasticity and mechanical strength can be tuned selectively by varying the concentration and size of the azide-functionalized SNP cross-linker. Furthermore, the shape of the bulk 3D material can be controlled by adding the functionalized SNPs and the SNP XLs to Teflon molds, followed by the cross-linking "click" reaction step (either in the presence of Cu or with heat) to yield the desired fixed hydrogel shape.

After the chemistry to generate the nanocomposite hydrogel network is optimized to fit a particular range of different elasticities and mechanical strengths, the different modes of actuation will be investigated, beginning with electrochemical stimulation via bulk electrolysis in an Argon-purged aqueous bath in a glovebox. The setup for this experiment is very similar to cyclic voltammetry measurements, except instead of sweeping through a voltage range, only one potential value is maintained in between the first and second reduction steps of the $V^{2+}$ subunits (so as not to overshoot the $V^{\cdot+}$ radical cation oxidation state). Moreover, the applied potential (−0.5 to −0.7 V) needed to activate the system is sufficiently low such that water splitting (at ~1.2-1.3 V) and the generation of oxygen within the hydrogel medium will not be an issue. Full characterization of this de-swelling process can be achieved by monitoring the change in UV-Vis absorption concurrently during the bulk electrolysis on an indium tin oxide (ITO) optically transparent slide, followed by measuring the total volume change associated with the electrochromic actuation. The nanocomposite hydrogel can also be activated chemically using either sodium dithionite, or simply by adding Zn dust through a heterogeneous electron transfer mechanism. After testing different nanocomposite hydrogel materials and shapes for actuation, the reverse process will be examined, initially by removing the material from the inert environment of the glovebox and exposing it to ambient conditions. The $O_2$ in the air will gradually oxidize the material and cause it to expand in an aqueous bath (via solvation and influx of counteranions in the polymer network). The other alternative is to treat the local aqueous environment around the nanocomposite hydrogel—while still in the glovebox—with a solution comprised of $NO^+PF6-$, a chemical oxidant which is capable of converting $V^{\cdot+}$ back to $V^{2+}$ and expelling NO gas as a byproduct. The doubling of the positive charges associated with the viologen subunits, in combination with the loss of the radical molecular recognition between each subunit, will ultimately result in network expansion and swelling of the nanocomposite hydrogel via solvation. The cyclability of this reversible electrochromic actuation process will be tested until material failure, if any, becomes evident.

Example 2: Light-Induced Actuation of the Nanocomposite Hydrogel

In order to gain spatial and temporal control over the actuation process of the nanocomposite hydrogel, it was proposed to introduce tris(bipyridine)-ruthenium(II) [Ru(bpy)$_3$] derivatives into the polymer network. It has been shown that photo-induced electron transfer (PET) can occur between Ru(bpy)$_3$ and viologen subunits of small molecules and oligomers in the presence of triethanolamine (TEOA) (the latter prevents back electron transfer from the viologen to the ruthenium center, as well as Ru$^{3+}$-induced water splitting). By irradiating a solution containing these small molecules with blue visible light (450-495 nm), photo-excitation of the ruthenium center occurs, followed by the transfer of an electron to generate the mono-reduced V$^{\bullet+}$ oxidation state. In principle, if a sufficient number of Ru(bpy)$_3$ complexes are available in the nanocomposite hydrogel network, then it should be feasible to achieve complete reduction of the V$^{2+}$ subunits to their corresponding mono-radical states in response to blue light.

Figures 4A, 4B, 4C:
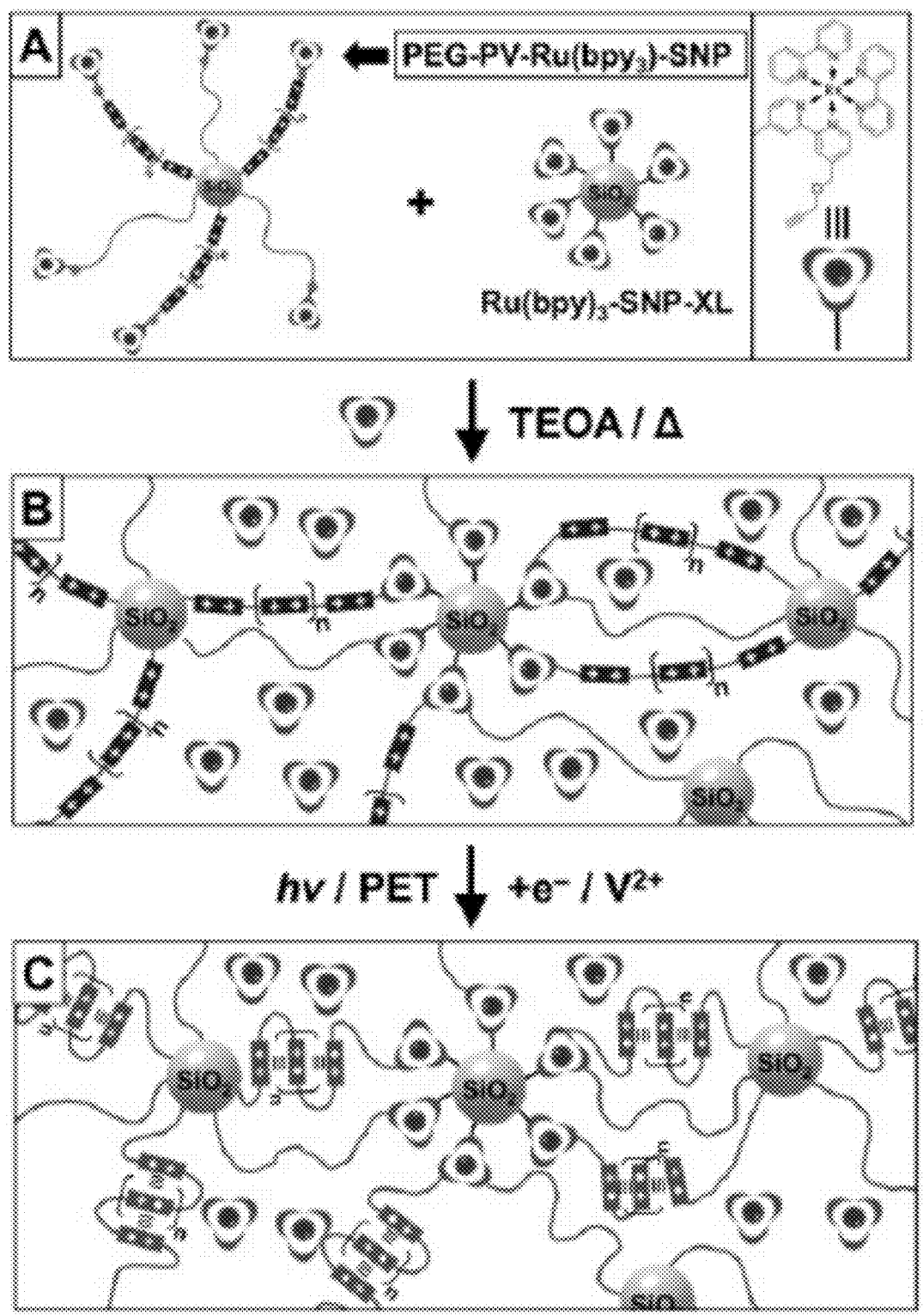
FIG. 4A is an illustration showing doping with tris(bipyridine)ruthenium(II) (Ru(bpy)) complexes (either free in solution or as functional end groups on the PEG/PEG-PV-SNP instead of alkyne groups), the cross-linking step can be carried out while heating in the presence of SNPs (namely, $Ru(bpy)_3$-SNP-XL) functionalized with existing $Ru(bpy)_3^{2+}$ complexes.
FIG. 4B illustrates the result is a photo-active supramolecular cross-linked nanocomposite hydrogel that can be activated by shining blue light (450-495 nm) on the bulk material.
FIG. 4C is an illustration showing the blue light causes stacking of $V_{•+}$ subunits and contraction of the polymer network as a consequence of photo-induced electron transfer (PET) from the ruthenium complexes to the $V^{2+}$ subunits. (TEOA=triethanolamine, a sacrificial reductant).

Therefore, a new method of cross-linking (see e.g., FIG. 4A, FIG. 4B) the PEG/PEG-PV-functionalized SNPs is proposed, whereby the ends of each polymer chain and the surface of the cross-linking SNPs will be functionalized covalently with Ru(bpy)$_3$ complexes. Heating a mixture of both surface-functionalized SNPs will disrupt the metal-to-ligand coordination on the surface of the cross-linker, such that some of the bipyridine units from the PEG/PEG-PV-functionalized SNPs will bind the ruthenium, effectively cross-linking and forming the nanocomposite hydrogel network. The cross-linking density, and thus the mechanical strength, of the polymer network can be manipulated simply by controlling the amount of the Ru(bpy$_3$)-SNP-XL that is added.

Once the physical properties of these more dynamic nanocomposite hydrogels have been established—similar to the manner described in Example 1—the site-selective and light-induced actuation of the material (see e.g., FIG. 4C) will be investigated, as well as the reversibility and cyclability after repeated PET activation of a particular region of a nanocomposite hydrogel. This method of cross-linking and light-induced actuation could potentially lead to stepwise manipulation of the adaptive materials in order to create new shapes and work functions, such as hydrogels capable of swimming or walking.

In short, a strategy has been proposed to develop novel light- and redox-responsive nanocomposite hydrogels that are capable of undergoing large, reversible volume changes in response to (electro)chemical stimulation. This supramolecular-based means of actuation will allow for greater reversible control over network chain lengths and will uncover new fundamental understandings of how non-covalent bonding interactions can serve as a collective driving force capable of macroscopic actuation of a bulk material.

Example 3: Redox-Responsive Artificial Molecular Muscles: Reversible Radical-Based Self-Assembly for Actuating 3D Soft Materials As described herein, the synthesis (see e.g., FIG. 5A-FIG. 5B) and application (see e.g., FIG. 5C) of water-soluble and unimolecular main-chain oligoviologens are reported for the first time as a cheap, robust, and highly responsive means of reversibly contracting and expanding three-dimensional (3D) soft materials in the timeframe of only tens of minutes. The novel mechanism of actuation (see e.g., FIG. 5C) involves the intramolecular collapse of the redox-active oligomer through the non-covalent, radical-based self-assembly of reduced main-chain viologen subunits—where a viologen radical-cation is generated chemically at each subunit. This mechanism is analogous to that of an accordion, whereby the thermodynamically favorable pairing of radical electrons between viologen subunits in the same network link results in a decrease in its length and mass and ultimately leads to a reduction in the overall mesh size of the 3D network. This radical-pairing effect serves as the driving force to reorganize the network and contract the bulk material down to 10-20% of its original volume and mass. Thus, even while sitting in salt-containing water, the driving force for network reorganization in a viologen-containing hydrogel (referred to hereafter as a viologel) is capable of excluding water and counterions from the bulk material.

In order to determine what effect the role of changing the oligomeric chain length plays in actuating a hydrogel—in terms of the total amount, or degree, that it can be contracted and expanded, as well as how quickly this process can be completed—an iterative synthesis was carried out (see e.g., FIG. 5A) that is akin to a sequential step-growth polymerization. Beginning with a bipyridine (BIPY) end-capped hexaethylene glycol (HEG) precursor, (HEG-BIPY), a viologen-containing dimer was synthesized in the presence of 20 equiv of tosyl end-capped HEG (HEG-Tos) in MeCN, heated to 130° C. in a sealed high-pressure flask. After 12-16 h, the HEG-BIPY is converted to $2V^{4+}$ (see e.g., FIG. 5A, top chemical structure) and the product was isolated through precipitation in a 1:1 mixture of PhMe and MeCN, followed by centrifugation. Similarly, the BIPY end-capped compound $2V^{6+}$ was prepared by treating $2V^{4+}$ with 20 equiv of 4,4'-bipyridine in MeCN, heated to 130° C. for 12-16 h, followed by precipitation and material recovery after centrifugation. This iterative synthetic protocol has been repeated several times, resulting in the synthesis of 100's of milligrams of the higher molecular weight oligomers and several grams of the shorter ones (i.e., n=2-4) of a series of unimolecular and even-numbered oligoviologens, where n=2, 4, 6, 8, or 10 for $nV^{(2n)+}$.

Figure 13:
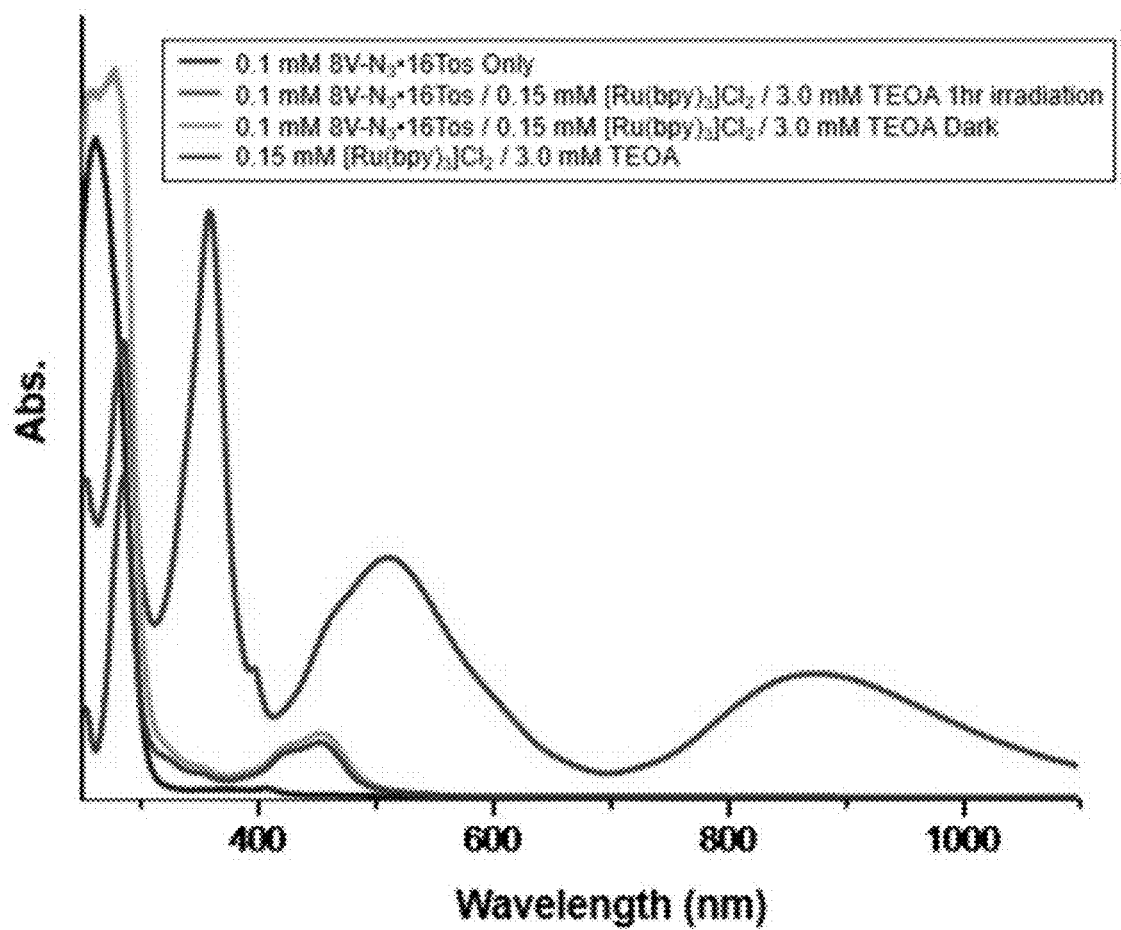
FIG. 13 is a UV-vis-NIR spectra of $8V-N_3.16Tos$ (0.1 mM in $H_2O$), $[Ru(bpy)_3]Cl_2/TEOA$ (0.15 mM/3.0 mM in $H_2O$), and a mixture of $8V-N_3.16Tos/[Ru(bpy)_3]Cl_2/TEOA$ (0.1 mM/0.15 mM/3.0 mM in $H_2O$, respectively) before (dark) and after irradiation with ~450 nm light for 1 h. Low energy absorptions at 515 nm and 875 nm in the trace corresponding to the irradiated $8V-N_3.16Tos/[Ru(bpy)_3]Cl_2/TEOA$ solution confirm photochemical reduction of the dicationic viologen subunits in the polyviologen chain to the radical cation state where subsequent formation of the radical cation pi-dimer (pimer) has occurred, respectively.

An investigation into the radical-pairing-induced intramolecular self-assembly, or collapse, of the oligoviologens was carried out separately in MeCN and H$_2$O, whereby each $nV^{(2n)+}$ compound (at 0.2 mM) was reduced to the corresponding $nV^{(n)\bullet+}$ radical cation by the excessive addition of zinc dust (Zn$^0$) or sodium dithionite (Na$_2$S$_2$O$_4$), respectively. Absorption spectroscopy (UV-vis-NIR) was then performed (see e.g., FIG. 13) on each of the dark purple colored oligoviologen solutions. In MeCN, two intense bands were observed with maximum absorptions at approx. 520 and 850 nm, with only mild bathochromic shifting observed as more viologen subunits were added in the higher molecular weight oligoviologens. In contrast, the study carried out in H$_2$O not only showed two intense absorption bands centered around 520 and 850 nm, but as the oligoviologens increased in molecular weight and degree of polymerization (DP), a strong bathochromic shift was observed, where the absorption peak centered about 850 nm for $2V^{4+}$ red-shifted up to 899 nm in the case of $10V^{20+}$ (see e.g., FIG. 13) and produced a broad shoulder that carried over into the 1000-1100 nm range. These trends associated with the absorption profiles of each oligoviologen have been investigated previously in other viologen-containing systems, and are an indication that while radical-radical dimerization is occurring in both solutions, there is some percent population in H$_2$O that is forming intramolecular tris(radical) stacks, as evidenced by the large amount of red-shifting that occurs as more viologen subunits are added to the oligomeric compound. To corroborate these results, an electron paramagnetic resonance (EPR) experiment was performed at room temperature on a 0.2 mM solution of $6V^{12+}$ dissolved in dry, degassed DMF (X-band). Since the radical pairing between reduced viologens is weaker in DMF, a signal possessing hyperfine splitting was observed, similar to what Winters and co-workers reported previously. Upon addition of H$_2$O (in aliquots) to the DMF solution containing $6V^{6(\cdot+)}$, a decrease in the EPR signal was observed, a trend which is presumably attributable to an increase in radical pairing between the $V^{\cdot+}$ subunits along the backbone of the oligomer. Moreover, this phenomenon is aided by the hydrophobic effect, which induces aggregation in less polar π-systems upon exposure to $H_2O$.

Figures 5A, 5B, 5C:
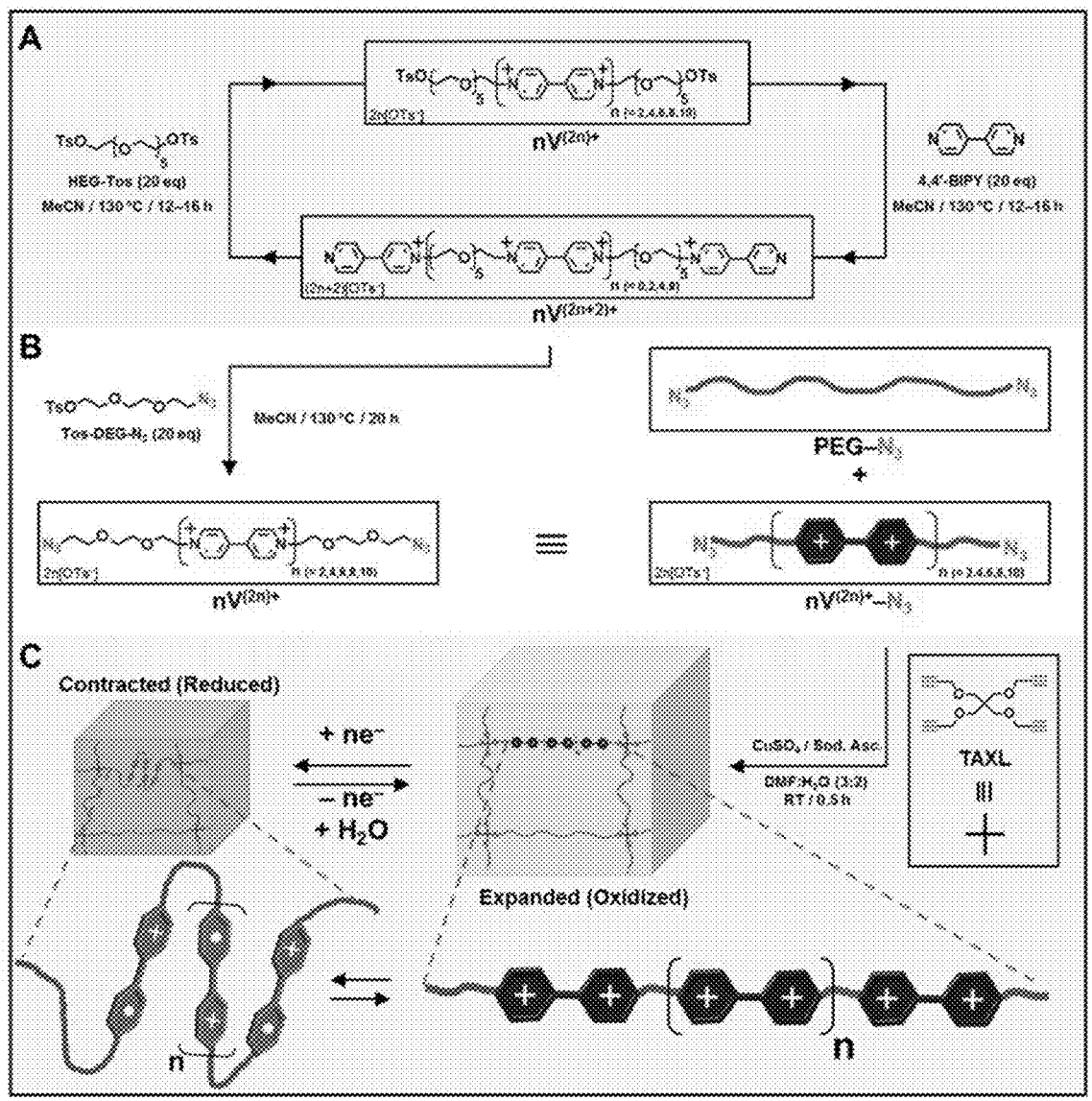
FIG. 5A-FIG. 5C is a series of schematics showing the production of the material (A-B) and the material in the contracted (reduced) and expanded (oxidized) state (C).

To fabricate the viologels, an azide end-capped polyethylene glycol ($PEG-N_3$) was prepared and combined with only 5 mol % of azide end-capped $nV^{(2n)+}$ (i.e., $nV^{(2n)+}-N_3$), and this mixture was dissolved in DMF along with 0.5 equiv of a tetra-alkyne cross-linker (TAXL) (see e.g., FIG. 5C). In a separate solution, 0.5 equiv of copper sulfate ($CuSO_4$) and 0.5 equiv of sodium ascorbate were dissolved in $H_2O$ and added to the DMF mixture in a 3:2 DMF:$H_2O$ ratio. This mixture of starting materials was vortexed for approx. 10 s before being deposited as a semi-viscous liquid into a cubic silicone mold, wherein the final cross-linking goes to completion, and the gel was thus formed. The copper was then removed by soaking the gel for 12-16 h in an aqueous Versene solution that contains 0.2 M ethylenediaminetetraacetic acid (EDTA) ligand in phosphate buffered saline (PBS), followed by washing in pure $H_2O$ solutions for an additional 4-6 h to remove any excess EDTA ligand. This process was repeated for all values of n noted above, such that three gels containing 5 mol % of each oligoviologen chain could be prepared, totaling 15 cubic hydrogels in all. Additionally, this protocol was also adapted to other molds, such as LC/MS vial caps and rubber septa, thus allowing for the preparation of disk-like gels that were used for assessing the mechanical properties of the gels (vide infra).

Figures 6A, 6B, 6C, 6D:
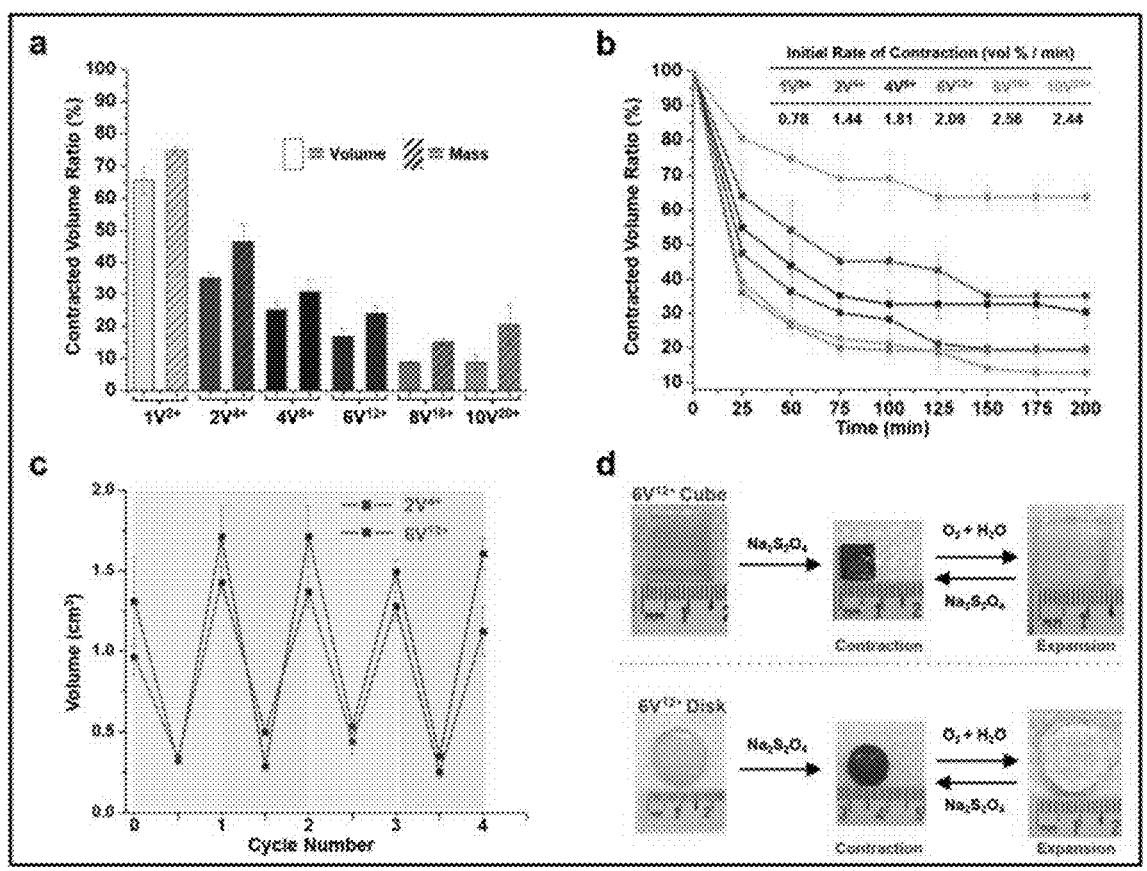
FIG. 6A-FIG. 6D is a series of graphs and images showing properties and characteristics of the materials.

With each oligoviologel now in hand, a systematic investigation was carried out where the number of available oligoviologen chains in the network was kept constant (i.e., identical mol % for all hydrogels), and instead only the length and molecular weight were varied as the different oligoviologens (n=2-10 subunits) were employed to make the corresponding viologels. The contraction of each gel (prepared in triplicate) was initiated by submerging each in a 1 M solution of $Na_2S_2O_4$ in an $N_2$-filled glovebox. It is important to note that the reduction can also be carried out on the bench top, with the caveat that fresh $Na_2S_2O_4$ solution be used since it degrades within a few hours upon exposure to atmospheric $O_2$. Placement of the hydrogels in the reducing solution resulted in a rapid change in color of the swollen hydrogels in only a matter of minutes, where the outside, and shortly thereafter the inside, of the hydrogel turned to a dark purple color. After sitting for a few hours in the reducing solution, the total degree of contraction was measured (see e.g., FIG. 6A) as the difference between the starting volume and mass of the swollen hydrogel (taller columns in FIG. 6A) and the corresponding volume and mass of the fully reduced and contracted hydrogel (smaller columns adjacent to the taller ones in FIG. 6A). A general trend becomes clear when looking at the contraction data across all oligoviologen samples in FIG. 6A. Specifically, the delta between the expanded and contracted states grows larger as more viologen subunits are introduced into the oligoviologen links in the 3D polymer network. This dramatic change in size and mass may be attributed to efficient collapse of the constituent oligoviologen chains as a consequence of radical pairing between subunits, but it is also largely due to the fact that a greater number of counterions are lost as more dicationic viologens ($V^{2+}$) are reduced to their corresponding radical cation ($V^{\cdot+}$). To our surprise, the kinetic assessment of each of the cubic viologels (see e.g., FIG. 6B)—particularly in the linear portion of the curve during the first 25 minutes— shows an increase in the rate of contraction ($cm^3 min^{-1}$) as higher DP oligoviologens are introduced into the network. This is counterintuitive since the longer oligoviologens constitute a slightly higher mass loading on account of the fact that the mol %—and therefore the number of oligomeric links—is kept constant across all hydrogels. The 'heavier' hydrogels would naturally thus be expected to diffuse and reorganize at a slower rate, an expectation which stands in contrast with the data shown in FIG. 6B.

In terms of the robustness of each hydrogel, four cycles of contractions and expansions were performed in triplicate (see e.g., FIG. 6C) for each cubic viologel. The first cycle typically started from a slightly smaller initial volume than the starting point of the second cycle, however, this may be attributed to the fact that more free void space is created after the first contraction pushes out any residual ligand or salt. Thereafter, the reversibility of the viologel actuation has been demonstrated successfully, with little to no loss in size and mass recovery. Generally speaking, the majority of the contraction of each of the swollen hydrogels occurs during the first 25 to 45 min. Thereafter, each viologel will lose a few more millimeters in each dimension, however, the fully contracted state can be realized in only a few hours, as evidenced by the images shown in FIG. 6D, which illustrate the change in color of the viologels upon reduction, as well as the dramatic size changes that occur for both cubic (top) and disk-like (bottom) hydrogels that contain 5 mol % of the oligoviologen chains ($nV^{(2n)+}$). Furthermore, it is important to note that the viologels are incapable of re-expansion when only $O_2$ or $H_2O$ is present. In other words, if a reduced/contracted viologel is exposed to $O_2$ on the benchtop (away from the chemically reducing solution), the color of the hydrogel will change from dark purple to yellow—an indication that the reduced viologen subunits have been oxidized—however the material cannot increase in size and mass since there is no $H_2O$ present. Likewise, the contracted viologel will remain dark purple in color and will not swell back to its original size when removed from the chemically reducing solution and placed in $N_2$-degassed $H_2O$ in a glovebox. Thus, both $O_2$ and $H_2O$ are required to activate the re-expansion of the material, a process where the latter usually results in 97-99% recovery in size and mass of the viologel (see e.g., FIG. 6D).

Figures 7A, 7B:
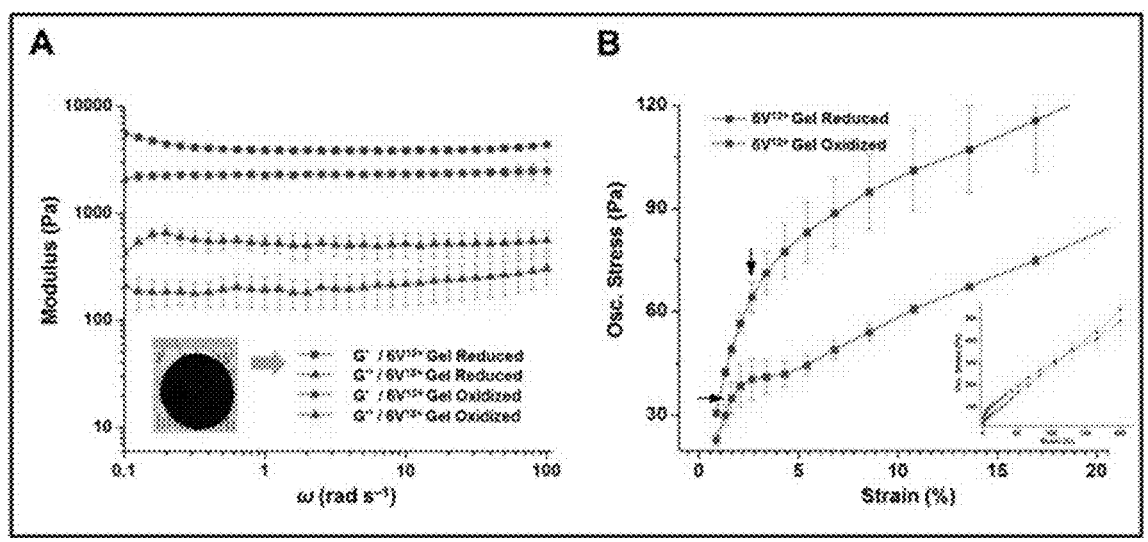
FIG. 7A-FIG. 7B is a series of graphs showing characterization of the dynamic viscoelastic behavior of the contracted and expanded viologels (A) and stress vs. strain curves (B).

Once the protocol for controlling the contraction and expansion had been established, it was then sought to quantify the change in mechanical properties of the viologel material as a function of the contracted state possessing decreased mesh sizes and a reorganized network. To characterize the dynamic viscoelastic behavior of the contracted and expanded viologels, an oscillatory shear rheometer (AR-G2, TA Instruments, Newcastle, Del.) was employed (see e.g., FIG. 7A) using a 20 mm flat geometry on disk-like $6V^{12+}$ viologels, which were 20 mm in diameter for both the contracted ($6V^{6(\cdot+)}$) and expanded states. The first experiment consisted of a frequency sweep (at 1% strain) from 0.1 Hz to 100 Hz on both the reduced and expanded viologels (performed in triplicate) in order to identify whether or not any viscous behavior could be observed at higher rates of shear torque. For both states, the material behaved as an elastic solid, where at no point a cross-over of G' and G" was observed, even at higher frequencies. There was, however, a roughly 2.5-fold increase in the elastic moduli (G') observed for the contracted viologels (purple squares shown in FIG. 7A) in comparison to the oxidized/expanded viologels (red squares in FIG. 7A). Moreover, the storage moduli G' was an order of magnitude greater than that of the loss moduli G" in the reduced state (i.e., ~5.4 vs. 0.5 kPa), compared to a difference of only a factor of four between the storage moduli (G'=~2.2 kPa) and loss moduli (G"=~0.23 kPa) in the oxidized state. Additionally, a strain sweep experiment was performed in triplicate at 10 rad/s on both the contracted and expanded viologels. This investigation resulted in stress vs. strain curves (see e.g., FIG. 7B), which show a linear viscoelastic region (LVR) in response to low strain in the range of 0-3%. The black arrows shown in FIG. 7B indicate the yield stress points for the reduced/contracted (purple trace) and oxidized/expanded (red trace) states of the viologels. As expected, the contracted viologels can undergo 63 Pa of stress at a slightly higher strain (3%) versus only 32 Pa of stress at approx. 1.5% strain. These results indicate that the decreased mesh size and corresponding reorganized network that results from the reduction of the oligoviologen chains in the viologels leads to a mechanically more robust material that can be handled more readily and even stretch farther before breaking.

Lastly, to demonstrate the versatility and performance of our novel actuatable platform, introducing only 5 mol % of the $2V^{4+}$ oligomer into a variety of 'showcase' viologels of different shapes, sizes, and masses was performed. Different viologel morphologies were synthesized (data not shown).

In conclusion, the development and implementation of a novel actuatable platform was successfully demonstrated. It was shown that the actuatable material based on flexible, water-soluble, and unimolecular oligoviologens can be incorporated in small molar amounts into a 3D bulk material for the purposes of reversibly controlling the contraction and expansion process of different hydrogel morphologies comprised of different shapes, sizes, and masses. The actuation mechanism is driven by the thermodynamically favorable radical pairing that occurs between main-chain viologen radical cations present in a series of oligoviologens that have been synthesized with even-numbered DPs ranging from 2-10 viologen subunits. The rapid collapse of these oligoviologen chains within the confines of 3D cross-linked polymer network—even whilst still submerged in $H_2O$—results in an overall reorganization that decreases the material's mesh size and excludes counterions and $H_2O$ from the material. It was also observed that the degree and rate of actuation is markedly improved for larger values of DP, and the bulk material can only be returned to its original state upon exposure of the reduced and contracted viologels to $O_2$ and $H_2O$. Moreover, it has been demonstrated that this process is completely reversible over several cycles and can be used to manipulate the mechanical properties of the material post-reorganization of the network, where a 2.5 fold increase in the elastic shear moduli (G') was observed upon contraction of the material as a result of chemical reduction of the oligoviologens and their subsequent non-covalent self-assembly into a collapsed aggregate. This process can be expanded to other materials outside of PEG and hydrogels and can be useful for a number of potential real-world materials applications.

Materials/General Methods/Instrumentation

All reagents were purchased from commercial suppliers and used without further purification unless stated otherwise. Literature procedures were employed in the synthesis of hexaethylene glycol di-p-toluenesulfonate (1) (Ts-HEG-Ts); 2-[2-(2-Azidoethoxy)ethoxy]ethyl-4-methylbenzenesulfonate (10) (Azido-Tos)[2]; PEG diazide (11) ($N_3$—PEG—$N_3$)[3]; and tetrakis(2-propynyloxymethyl)methane (12) (TAXL). All chemical reductions of hydrogels, electrochemical measurements, and EPR samples were performed or prepared under an inert atmosphere of UHP nitrogen. Column chromatography was carried out on silica gel 60F (EMD Millipore, 0.040-0.063 mm). To aid in the precipitation of Oligo/polyviologen material from the crude reaction mixture a Thermo Scientific Sorvall ST 8 small benchtop centrifuge was employed. All Nuclear magnetic resonance (NMR) spectra were recorded on Varian (nova-500 and Varian Mercury-300 spectrometers at 25° C., with working frequencies of 500 ($^1H$) and ($^{13}C$) MHz and 300 ($^1H$) MHz, respectively. Chemical shifts are reported in ppm relative to the signals corresponding to the residual non-deuterated solvents: $CD_3CN$: δH=1.94 ppm and δC=1.32 ppm; $CDCl_3$: δH=7.24 ppm and δC=77.0 ppm. Ultraviolet-Visible-Near Infrared (UV-Vis-NIR) absorbance spectra were recorded on an Agilent Cary 5000 spectrophotometer with a PbSmart NIR detector. Electrochemical measurements were obtained with a Gamry multipurpose potentiostat with a Ag/AgCl reference electrode, glassy carbon working electrode, platinum wire auxiliary electrode, and [$^nBu_4N$][$PF_6$] as supporting electrolyte, all measurements were calibrated vs. $Cp_2Fe$. Electron Paramagnetic resonance (EPR) spectra were recorded at X-band frequency (9.2 GHz) on a JOEL JES-FA X-BAND EPR spectrometer at 298 K. Frequency sweep and strain sweep experiments were performed on an Anton Paar MCR 301 rheometer with 20 mm geometry.

Synthetic Protocols

1) Iterative Synthesis of Tosyl-Capped Oligo/Poly-Viologen Crosslinker a) 2a: 2V·2Tos, Dimer Precursor (Scheme 1)

Scheme 1. Synthesis of 2V·2Tos (2a)

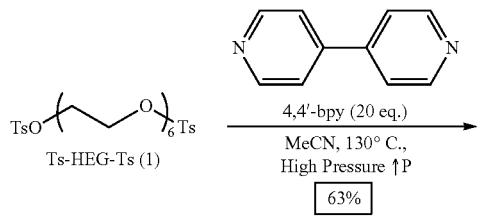

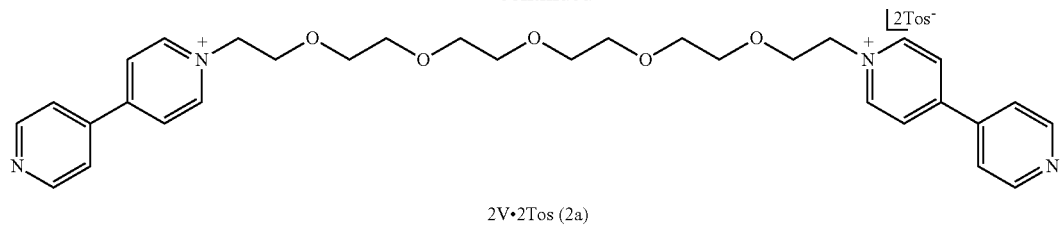

2V·2Tos (2a)

2V·2Tos: A 100 mL thick walled high pressure flask with Teflon screw cap and stir bar was charged with (1) (1.206 g, 2.3 mmol), 4,4-bipyridine (6.5 g, 40 mmol), and MeCN (15 mL). The flask was capped tightly and the mixture was stirred at high-pressure at 130° C. for 12 h. After 12 h, the reaction mixture was cooled to room temperature (caution: do not open vessel until room temperature is achieved) and the crude golden brown mixture was transferred to a 50 mL plastic centrifuge tube and toluene (30 mL) was added to precipitate the pure product as a sticky brown oil. To assist in the precipitation and purification of the product the MeCN/toluene mixture was centrifuged twice at 4490 rpm at −10° C. for 35 min, replacing the supernatant with fresh toluene between runs. To maximize yields the MeCN/Toluene supernatant should be concentrated under reduced pressure and centrifuged a third time at identical conditions (1.176 g, 63%). $^1$H NMR (300 MHz, CD$_3$CN) δ 8.93 (d, J=6.9 Hz, 4H), 8.80 (dd, J=4.5, 1.7 Hz, 4H), 8.30 (d, J=6.8 Hz, 4H), 7.86-7.67 (m, 4H), 7.59 (d, J=8.1 Hz, 4H), 7.12 (d, J=7.9 Hz, 4H), 4.83-4.69 (m, 4H), 4.03-3.86 (m, 4H), 3.63-3.38 (m, 16H), 2.29 (s, 6H); $^{13}$C NMR (75 MHz, CD$_3$CN) δ 161.68, 152.17, 146.73, 129.29, 126.61, 126.34, 122.76, 71.06, 70.99, 70.99, 70.75, 69.66, 21.16, 21.13.

b) 2b: 2V·4Tos, Dimer (Scheme 2)

2V·4Tos: A 100 mL thick walled high pressure flask with Teflon screw cap and stir bar was charged with (2a) (1.206 g, 0.69 mmol), Ts-HEG-Ts (8.25 g, 13.9 mmol), and MeCN (20 mL). The flask was capped tightly and the mixture was stirred at high-pressure at 130° C. for 16 h. After 16 h, the reaction mixture was cooled to room temperature and the crude golden brown mixture was transferred in equal parts to two 50 mL plastic centrifuge tubes and toluene (30 mL) was added to each tube to precipitate the pure product as a sticky brown oil. To assist in the precipitation and purification of the product the MeCN/toluene mixture was centrifuged twice at 4490 rpm at −10° C. for 35 min, replacing the supernatant with fresh toluene between runs. To maximize yields the MeCN/Toluene supernatant should be concentrated under reduced pressure and centrifuged a third time at identical conditions (1.238 g, 86%). $^1$H NMR (500 MHz, CD3CN) δ 9.03 (s, broad, 8H), 8.48 (s, broad, 8H), 7.79-7.66 (m, 4H), 7.62-7.51 (m, 8H), 7.38 (m, 4H), 7.17-7.00 (m, 8H), 4.80 (s, broad, 8H), 4.12-3.77 (m, 8H), 3.63-3.30 (m, 56H), 2.43-2.33 (m, 6H), 2.30-2.16 (m, 12H). $^{13}$C NMR (126 MHz, CD3CN) δ 149.29, 146.51, 145.45, 143.18, 140.06, 132.64, 130.15, 128.84, 127.79, 126.66, 125.88, 70.17, 70.14, 70.06, 69.92, 69.80, 68.82, 68.18, 61.36, 20.76, 20.47.

Scheme 2. Synthesis of 2V•4Tos (2b), dimer

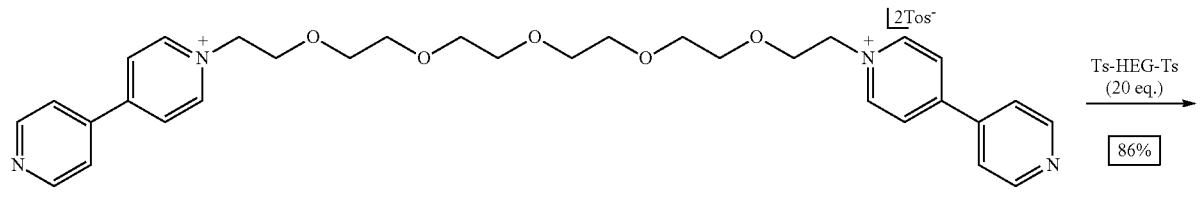

2V·2Tos (2a)

Ts-HEG-Ts (20 eq.) →

86%

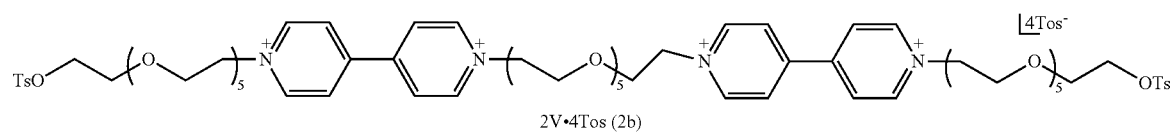

2V·4Tos (2b)

c) 3a: 4V·6Tos, Tetramer Precursor (Scheme 3)

Scheme 3. Synthesis of 4V•6Tos (3a)

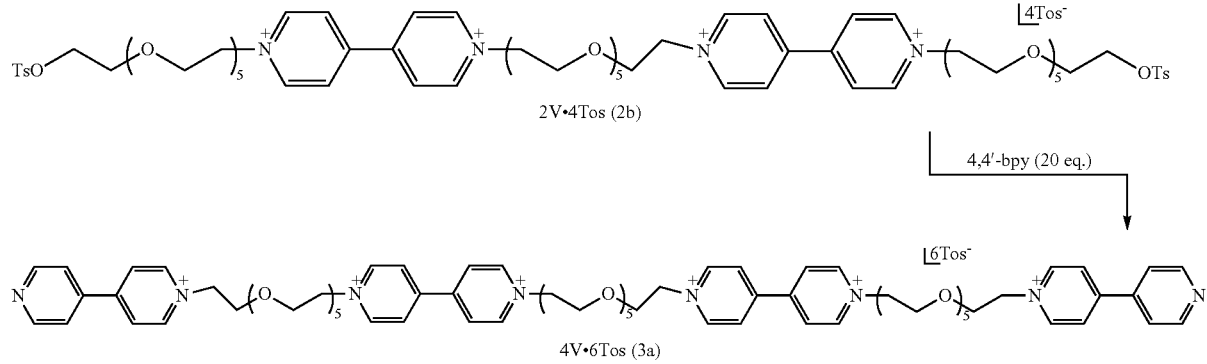

4V·6Tos: A 100 mL thick walled high pressure flask with Teflon screw cap and stir bar was charged with (2b) (0.500 g, 0.24 mmol), 4,4-bypyridine (4.8 mmol), and MeCN (20 mL). The flask was capped tightly and the mixture stirred at high-pressure at 130° C. for 16 h. After 16 h, the reaction mixture was cooled to room temperature and the crude dark brown mixture was transferred in equal parts to two 50 mL plastic centrifuge tubes and toluene (30 mL) was added to each tube to precipitate the pure product as a sticky brown oil. To assist in the precipitation and purification of the product the MeCN/toluene mixture was centrifuged three times at 4490 rpm at −10° C. for 35 min, replacing the supernatant with fresh toluene between runs. To maximize yields the MeCN/Toluene supernatant should be concentrated under reduced pressure and centrifuged a fourth time at identical conditions (0.468 g, 81%). $^1$H NMR (500 MHz, CD$_3$CN) δ 9.13-9.03 (m, 8H), 8.98-8.88 (m, 4H), 8.78-8.70 (m, 4H), 8.58-8.47 (m, 8H), 8.30-8.18 (m, 4H), 7.77-7.70 (m, 4H), 7.57 (d, J=8.1 Hz, 12H), 7.08 (d, J=8.1 Hz, 12H), 4.89-4.70 (m, 12H), 3.90 (s, 12H), 3.58-3.31 (m, 48H), 2.22 (s, 18H). $^{13}$C NMR (126 MHz, cd3cn) δ 151.88, 147.51, 146.89, 146.23, 139.82, 129.47, 127.59, 126.68, 126.29, 122.88, 118.26, 71.10, 70.99, 70.74, 69.75, 62.15, 21.25.

d) 3b: 4V·8Tos, Tetramer (Scheme 4)

Scheme 4. Synthesis of 4V•8Tos (3b)

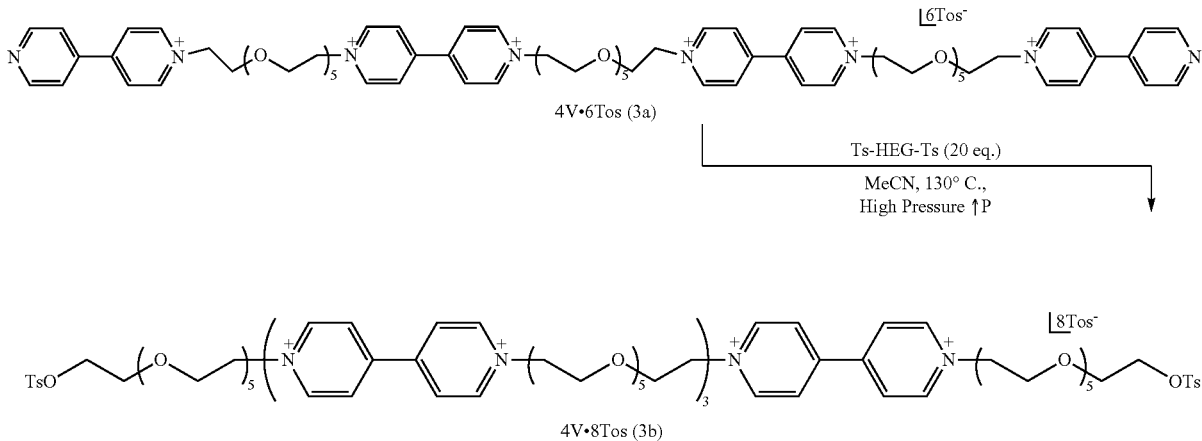

4V·8Tos: The preparation of (3b) follows the protocol previously established for compound (2b). (3a) (0.230 g, 0.06 mmol), Ts-HEG 73% (1.13 g, 1.2 mmol), and MeCN (10 mL), (0.25 g, 73%). $^1$H NMR (500 MHz, CD$_3$CN) δ 9.03 (s, broad, 16H), 8.52 (s, broad, 16H), 7.74-7.67 (m, 4H), 7.61-7.50 (m, 16H), 7.41-7.38 (m, 4H), 7.11-7.09 (m, 16H), 4.80 (s, broad, 16H), 4.04-3.89 (m, 16H), 3.55-3.43 (m, 88H), 2.43-2.33 (m, 6H), 2.30-2.16 (m, 24H). $^{13}$C NMR (126 MHz, CD$_3$CN) δ 147.33, 145.04, 140.26, 130.90, 129.47, 128.58, 127.45, 126.59, 70.93, 70.84, 70.71, 70.57, 69.60, 68.97, 21.16.

e) 4a: 6V·10Tos, Hexamer Precursor (Scheme 5)

Scheme 5. Synthesis of 6V·10Tos (4a)

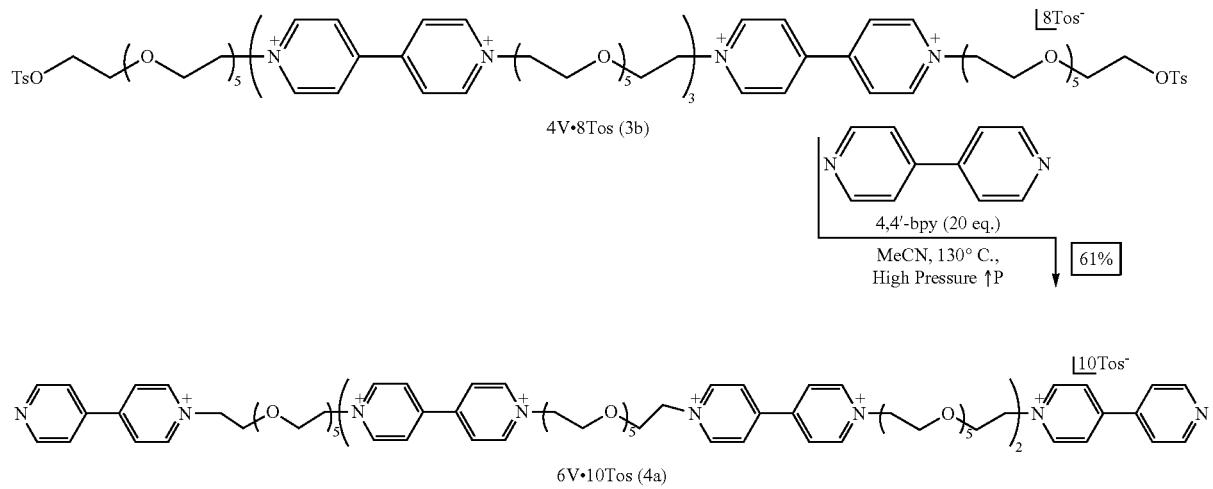

6V·10Tos: The preparation of (4a) follows the protocol previously established for compound (3a). (3b) (0.98 g, 0.27 mmol), 4,4-bypiridine (0.87 g, 5.4 mmol), and MeCN (20 mL), (0.64 g, 61%). $^1$H NMR (500 MHz, CD$_3$CN) δ 9.10 (s, broad, 16H), 8.94 (s, broad, 4H), 8.78 (s, broad, 4H), 8.55 (s, broad, 16H), 8.29 (s, 4H), 7.82-7.70 (m, 4H), 7.64-7.49 (m, 20H), 7.15-7.01 (m, 20H), 4.81 (t, broad, 20H), 3.93-3.90 (m, broad, 20H), 3.62-3.34 (m, 80H), 2.31-2.23 (m, 30H). $^{13}$C NMR (126 MHz, CD$_3$CN) δ 147.52, 146.31, 139.80, 129.46, 126.69, 71.01, 21.26.

f) 4b: 6V·12Tos, Hexamer (Scheme 6)

Scheme 6. Synthesis of 6V·12Tos (4b)

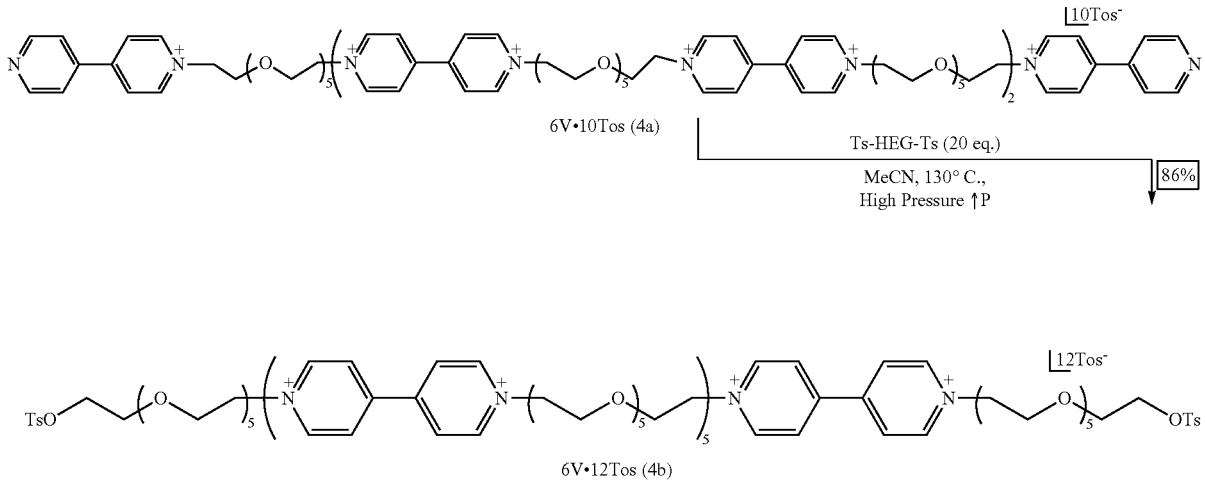

6V·12Tos: The preparation of (4b) follows the protocol previously established for compound (2b). (4a) (0.16 g, 0.04 mmol), Ts-HEG-Ts (0.44 g, 0.74 mmol), and MeCN (10 mL), (0.16 g, 86%). 1HNMR (500 MHz, CD3CN) δ 9.06 (s, broad, 24H), 8.50 (s, broad, 24H), 7.81-7.75 (m, 4H), 7.61-7.60 (d, broad, 24H), 7.41-7.38 (m, 4H), 7.11-7.09 (d, broad, 24H), 4.81 (s, broad, 24H), 4.04-3.89 (m, 24H), 3.55-3.43 (m, 120H), 2.43-2.33 (m, 6H), 2.30-2.16 (m, 36H). 13C NMR (126 MHz, cd3cn) δ 147.36, 141.45, 131.70, 130.92, 129.84, 127.56, 126.92, 70.95, 70.70, 69.57, 62.21, 21.33.

g) 5a: 8V·14Tos, Octamer Precursor (Scheme 7)

Scheme 7. Synthesis of 8V·14Tos (5a)

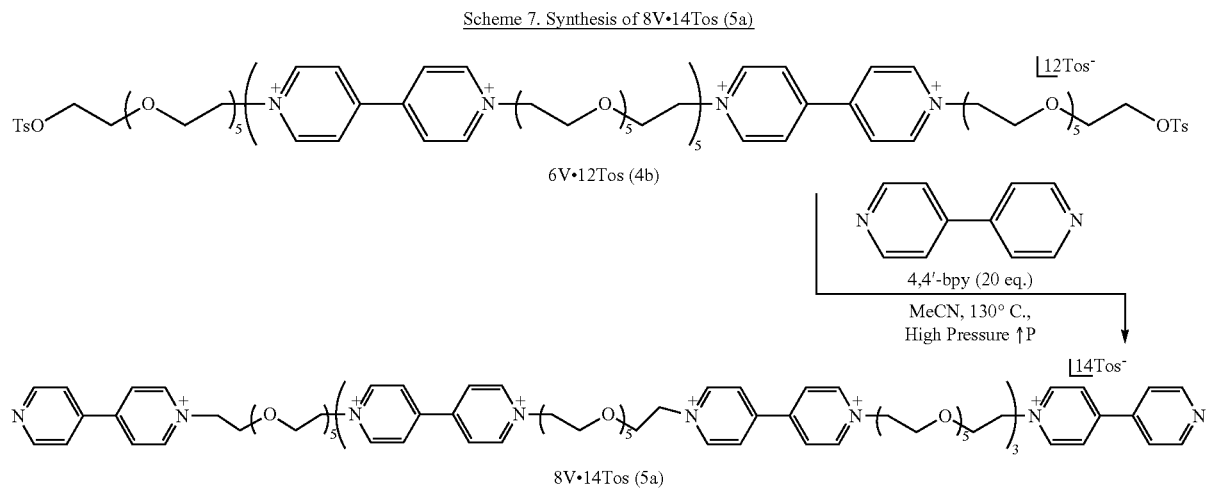

8V·14Tos (5a)

8V·14Tos: The preparation of (5a) follows the protocol previously established for compound (3a). (4b) (0.48 g, 0.09 mmol), 4,4-bypiridine (0.30 g, 1.8 mmol), and MeCN (10 mL), (0.469 g, 93%). $^1$H NMR (500 MHz, CD$_3$CN) δ 9.09 (s, broad, 24H), 8.93 (s, broad, 4H), 8.76 (s, broad, 4H), 8.52 (s, broad, 24H), 8.27 (s, 4H), 7.85-7.79 (m, 4H), 7.59-7.49 (m, 28H), 7.11-7.02 (m, 28H), 4.79 (t, broad, 28H), 3.86 (s, broad, 28H), 3.49-3.41 (m, 112H), 2.27-2.19 (m, 42H). $^{13}$C NMR (126 MHz, CD$_3$CN) δ 146.57, 145.96, 145.31, 138.85, 128.51, 126.65, 125.73, 70.15, 70.04, 68.79, 61.13, 20.30.

h) 5b: 8V·16Tos, Octamer (Scheme 8)

Scheme 8. Synthesis of 8V·16Tos (5b)

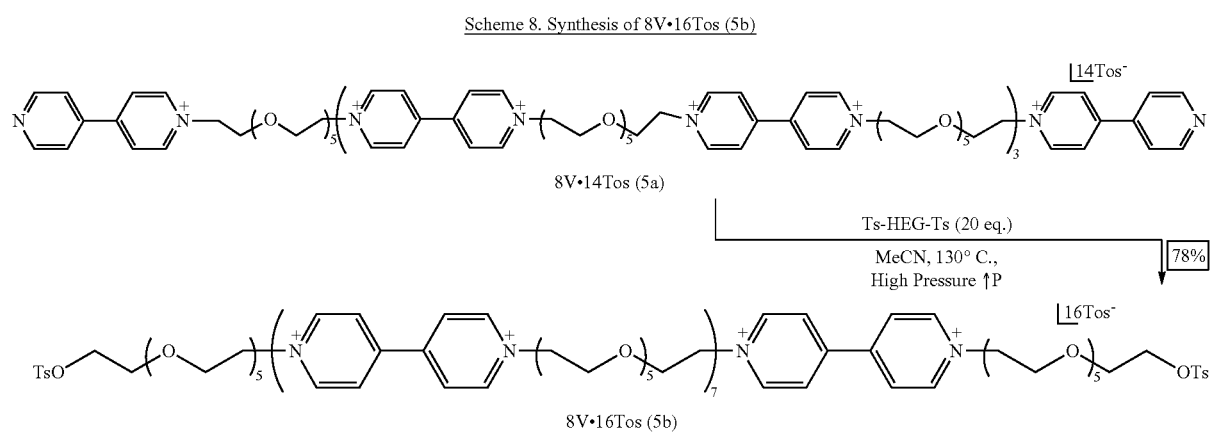

8V·16Tos (5b)

8V·16Tos: The preparation of (5b) follows the protocol previously established for compound (2b). (5a) (0.19 g, 0.04 mmol), Ts-HEG-Ts (0.41 g, 0.70 mmol), and MeCN (10 mL), (0.18 g, 78%). $^1$H NMR (500 MHz, CD$_3$CN) δ 9.09 (s, broad, 32H), 8.54 (s, broad, 32H), 7.83-7.77 (m, 4H), 7.62-7.60 (m, 32H), 7.54-7.49 (m, 4H), 7.17-7.09 (m, 32H), 4.82 (s, broad, 32H), 4.14-3.91 (m, 32H), 3.62-3.47 (m, 152H), 2.1 (s, broad, 6H), 2.29 (s, 48H). $^{13}$C NMR (126 MHz, CD$_3$CN) δ 147.40, 145.43, 140.21, 130.92, 129.54, 128.60, 127.55, 126.66, 71.03, 70.91, 70.67, 69.61, 62.20, 21.25.

i) 6a: 10V·18Tos, Decamer Precursor (Scheme 9)

Scheme 9. Synthesis of 10V•18Tos (6a)

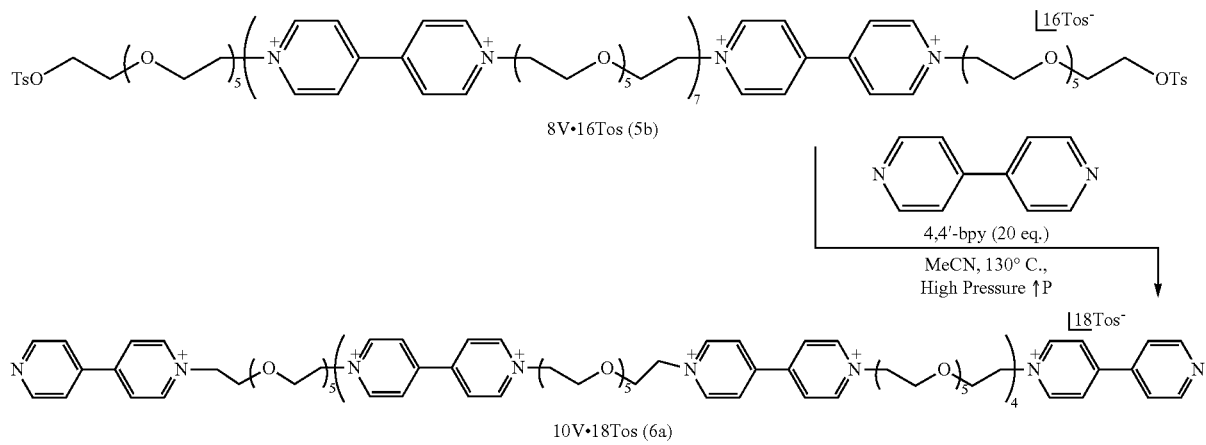

10V•18Tos (6a)

10V·18Tos: The preparation of (6a) follows the protocol previously established for compound (3a). (5b) (0.31 g, 0.47 mmol), 4,4-bypiridine (0.15 g, 0.09 mmol), and MeCN (10 mL), (0.27 g, 82%). $^1$H NMR (500 MHz, $CD_3CN$) δ 9.09 (s, broad, 32H), 8.93 (s, broad, 4H), 8.78 (s, broad, 4H), 8.52 (s, broad, 32H), 8.27 (s, 4H), 7.80-7.76 (m, 4H), 7.59-7.53 (m, 36H), 7.13-7.04 (m, 36H), 4.80 (t, broad, 36H), 3.89 (s, broad, 36H), 3.52-3.43 (m, 144H), 2.31-2.22 (m, 54H). $^{13}$C NMR (126 MHz, $CD_3CN$) δ 146.52, 145.37, 138.81, 128.48, 128.48, 126.63, 125.72, 70.04, 69.95, 68.77, 60.90, 20.29.

f) 6b: 10V·20Tos, Decamer (Scheme 10)

Scheme 10. Synthesis of 10V•20Tos (6b)

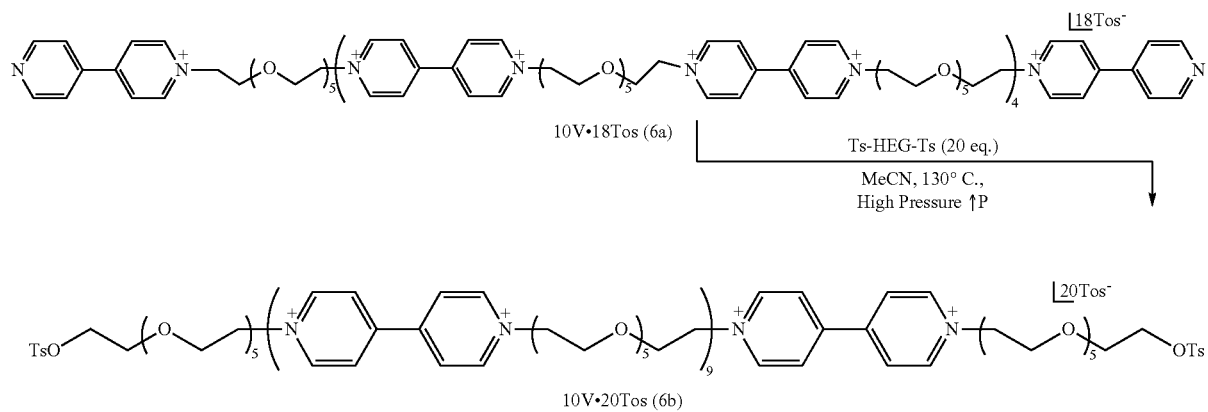

10V•20Tos (6b)

10V·20Tos: The preparation of (6b) follows the protocol previously established for compound (2b). (6a) (0.12 g, 0.02 mmol), Ts-HEG-Ts (0.55 g, 0.34 mmol), and MeCN (10 mL), (0.18 g, 78%). $^1$HNMR (500 MHz, $CD_3CN$) δ 9.06 (s, broad, 40H), 8.50 (s, broad, 40H), 7.78-7.7 (m, 4H), 7.55 (d, J=8.1 Hz, 40H), 7.42-7.39 (m, 4H), 7.09 (d, J=8.0 Hz, 40H), 4.83-4.79 (m, broad, 40H), 4.10-3.87 (m, 40H), 3.59-3.43 (m, 184H), 2.43-2.33 (m, 6H), 2.30-2.16 (m, 60H). 13C NMR (126 MHz, $CD_3CN$) δ 147.43, 144.74, 140.63, 131.03, 129.66, 128.74, 127.56, 126.76, 70.97, 69.67, 69.19, 21.31.

2) Preparation of Azide-Capped Oligo/Polyviologen Crosslinker a) 2c: 2V-N3·20Tos, Dimer (Scheme 11)

Scheme 11. Synthesis of 2V-N$_3$•4Tos (2c)

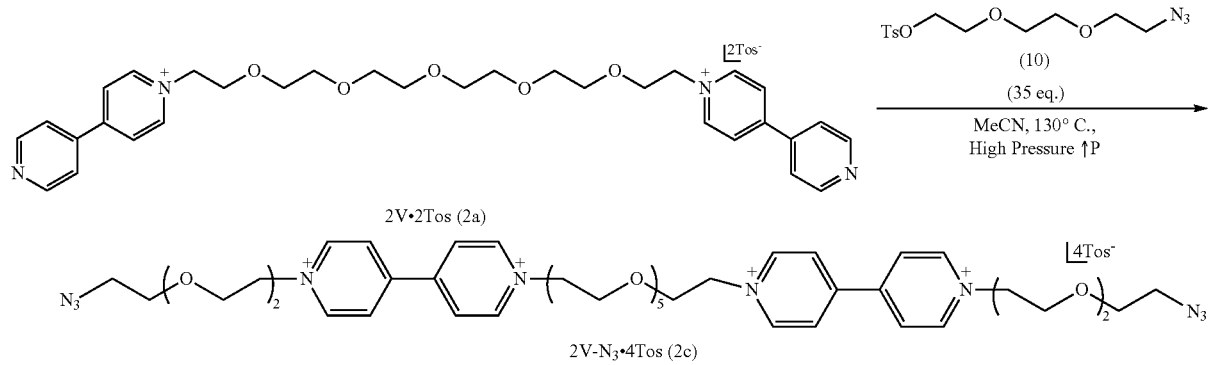

2V-N3·4Tos: A 100 mL thick walled high pressure flask with Teflon screw cap and stir bar was charged with (1) (0.300 g, 0.33 mmol), (10) (3.98 g, 11.5 mmol), and MeCN (15 mL). The flask was capped tightly and the mixture was stirred at high-pressure at 130° C. for 24 h. After 24 h, the reaction mixture was cooled to room temperature and the crude golden brown mixture was transferred to a 50 mL plastic centrifuge tube and toluene (30 mL) was added to precipitate the pure product as a sticky brown oil. To assist in the precipitation and purification of the product the MeCN/toluene mixture was centrifuged twice at 4490 rpm at −10° C. for 35 min, replacing the supernatant with fresh toluene between runs. To maximize yields the MeCN/Toluene supernatant should be concentrated under reduced pressure and centrifuged a third time at identical conditions (0.30 g, 56%). This protocol was also employed in the preparation of 3c, 4c, 5c, and 6c. $^1$H NMR (500 MHz, CD$_3$CN) δ 9.04 (s, broad, 8H), 8.49 (s, broad, 8H), 7.56 (s, broad, 8H), 7.10 (s, broad, 8H), 4.80 (s, broad, 8H), 3.90 (s, broad, 8H), 3.51-3.44 (m, broad, 24H), 3.28 (s, broad, 4H), 2.24 (s, 12H).

b) 3c: 4V-N3·8Tos, Tetramer

4V-N3·8Tos: (3a) (0.40 g, 0.18 mmol), (10) (2.17 g, 6.3 mmol), and MeCN (15 mL), (0.42 g, 79%). $^1$H NMR (500 MHz, CD$_3$CN, ppm): δH 9.07 (s, broad, 16H), 8.52 (s, broad, 16H), 7.55 (s, broad, 16H), 7.10 (s, broad, 16H), 4.79 (s, broad, 12H), 3.89 (s, broad, 12H), 3.51-3.43 (m, broad, 48H), 3.22 (s, broad, 4H), 2.24 (s, 24H).

c) 4c: 6V-N3·12Tos, Hexamer

6V-N3·12Tos: (4a) (0.28 g, 0.7 mmol), (10) (0.27 g, 2.2 mmol), and MeCN (15 mL), (0.18 g, 88%). $^1$H NMR (500 MHz, CD$_3$CN, ppm): δH$^1$ 9.08 (s, broad, 24H), 8.53 (s, broad, 24H), 7.55 (s, broad, 24H), 7.08 (s, broad, 24H), 4.81 (s, broad, 16H), 3.89 (s, broad, 16H), 3.51-3.42 (m, broad, 72H), 3.29 (s, broad, 4H), 2.24 (s, 36H).

d) 5c: 8V-N3·16Tos, Octamer

8V-N3·16Tos: (5a) (0.17 g, 0.03 mmol), (10) (0.381 g, 1.1 mmol), and MeCN (10 mL), (0.18 g, 78%). $^1$H NMR (500 MHz, CD$_3$CN, ppm): δH$^1$ 9.07 (s, broad, 32H), 8.53 (s, broad, 32H), 7.55 (s, broad, 32H), 7.09 (s, broad, 32H), 4.81 (s, broad, 20H), 3.89 (s, broad, 20H), 3.51-3.43 (m, broad, 96H), 3.29 (s, broad, 4H), 2.24 (s, 48H).

e) 6c: 10V-N3·20Tos, Decamer

10V-N3·20Tos: (6a) (0.12 g, 0.02 mmol), (10) (0.21 g, 0.61 mmol), and MeCN (10 mL), (0.12 g, 93%). $^1$H NMR (500 MHz, CD$_3$CN, ppm): δH 1 9.05 (s, broad, 20H), 8.51 (s, broad, 40H), 7.53 (s, broad, 40H), 7.06 (s, broad, 40H), 4.81 (s, broad, 24H), 3.87 (s, broad, 24H), 3.49-3.42 (m, broad, 120H), 3.29 (s, broad, 4H), 2.24 (s, 60H)

3) General Procedure for the Preparation of Oligo/Polyviologen Click Hydrogels 5 mol % Oligo/polyviologen "Click" Hydrogel—dimer, tetramer, hexamer, octamer: N$_3$—PEG-N$_3$ (11) (0.100 g, 0.05 mmol), TAXL (12) (0.068 g, 0.02 mmol), and azide capped oligo/polyviologen (2.3 μmol) were added to a glass scintillation vial and 0.9 mL of DMF was added. The mixture was vortexed until all of the solid entered solution. Then, Cu$_2$SO$_4$ (0.04 g, 0.02 mmol) and sodium ascorbate (0.05 g, 0.05 mmol) were added to separate 1 dram vials and dissolved in 0.3 mL of deionized water. The CuSO$_4$/H$_2$O solution was then added in its entirety via a syringe to the polymer/DMF solution and the viscous green colored solution was vortexed for 10 sec. to ensure homogeneity of the pre-gel mixture. Then, using a syringe the sodium ascorbate soln. in H$_2$O was quickly added to the pre-gel mixture and then vortexed for an additional 10 sec. The gel reaction mixture was then carefully and rapidly plated into three 1 cm cubic silicone mold via a syringe. The gelation process was complete after 30 min. The resulting hydrogels were then swollen in Versene overnight to remove excess copper ions remaining in the gel.

Spectroscopic Methods

Figure 9:
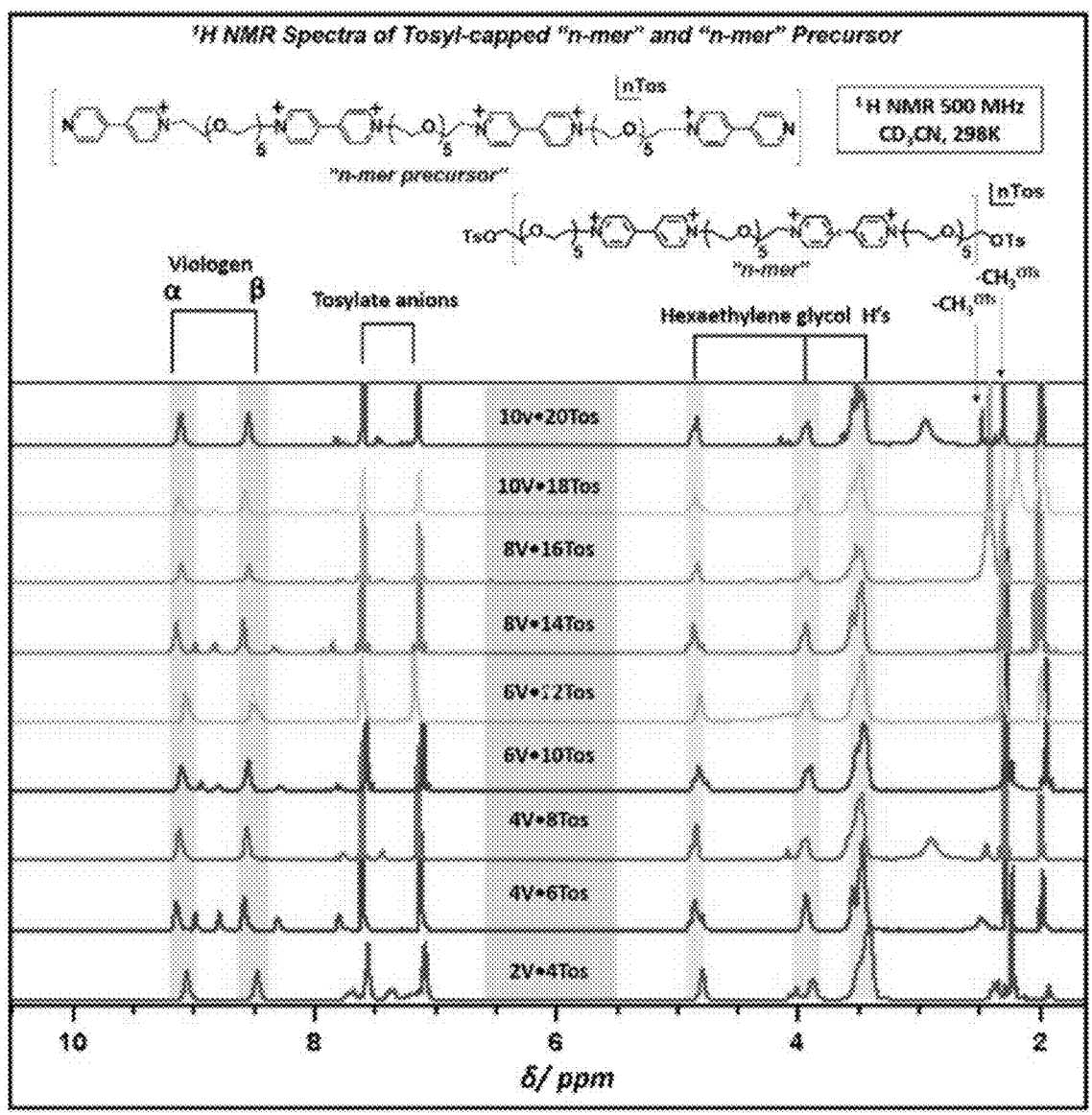
FIG. 9 is a series of NMR spectra of Tosyl-capped "n-mer" and "n-mer" precursor.

1) $^1$H NMR Spectra (See e.g., FIG. 9)

All tosyl-capped oligo/polyviologens and precursors.

Figure 10:
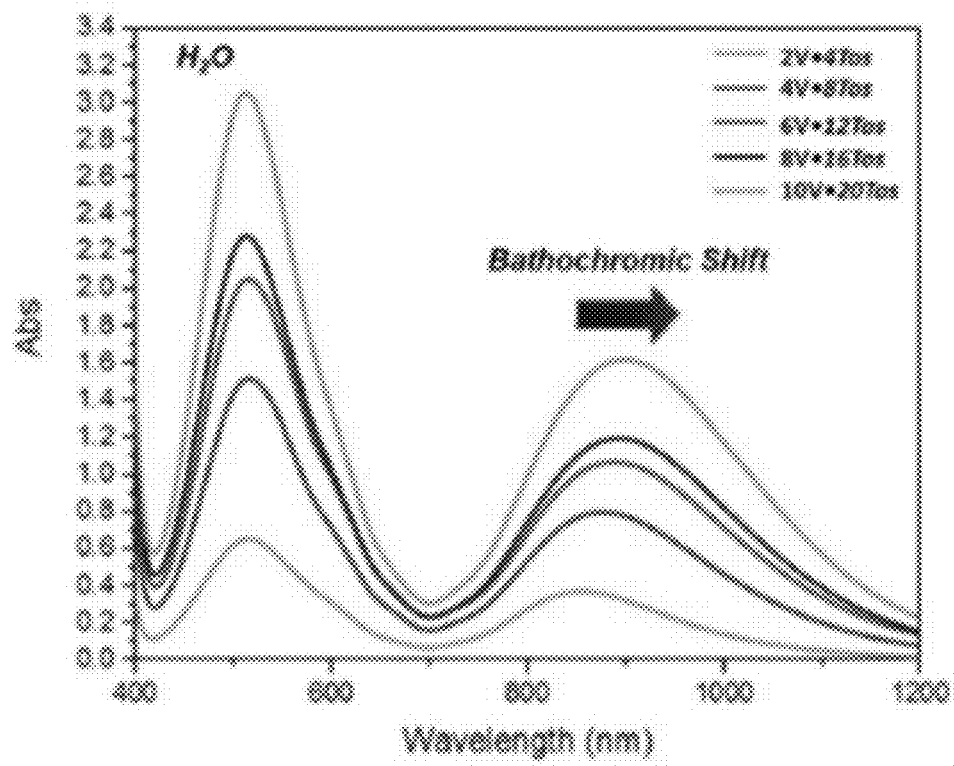
FIG. 10 is a series of UV Vis NIR spectra of Tosyl-capped oligo/polyviologens.
Figure 10:
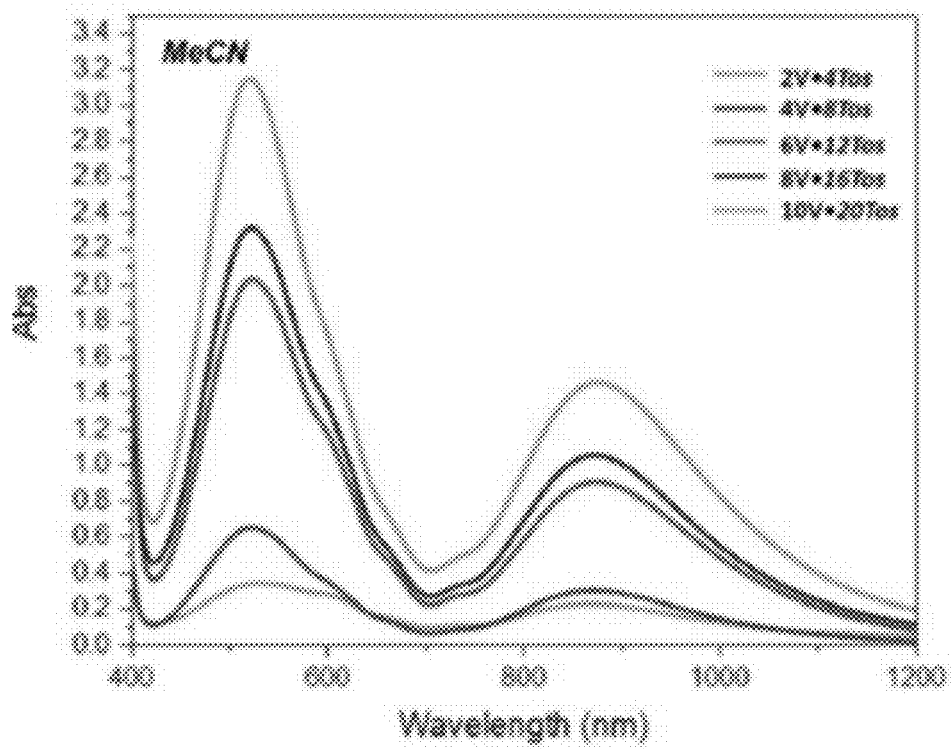

2) UV-VIS-NIR Spectra (See e.g., FIG. 10)

All tosyl capped oligo/polyviologen in H$_2$O, 0.2 mM

The UV-Vis-NIR spectra of the chemically reduced forms of assorted oligo/polyviologens were recorded at a concentration of 0.2 mM in H$_2$O employing excess 1M sodium dithionite as a water soluble and in MeCN using zinc dust as a reductant. The generation of viologen radical cations in solution triggers self-assembly in the form of spin-paired pi-stacked dimers (pimers); these pimers show a characteristic low energy absorption in the near IR around 800-850 nm. In addition to dimer formation, tris(radical) pi-stacks can also form in solution and show a characteristic absorption around 1000 nm. The purpose of this spectroscopic study is to investigate the self-assembly in solution of oligo/polyviologen chains as a function of chain length. It is observed as the chains increase in length the lambda max in the near IR region shows a distinct red-shift in the spectral profile in the spectra taken in water; this is due to hydrophobic effects which push the equilibrium toward pimer formation. This suggests that with increasing oligo/polyviologen chain length the more diverse the conformations of self-assembled viologen in solution.

Figure 11:
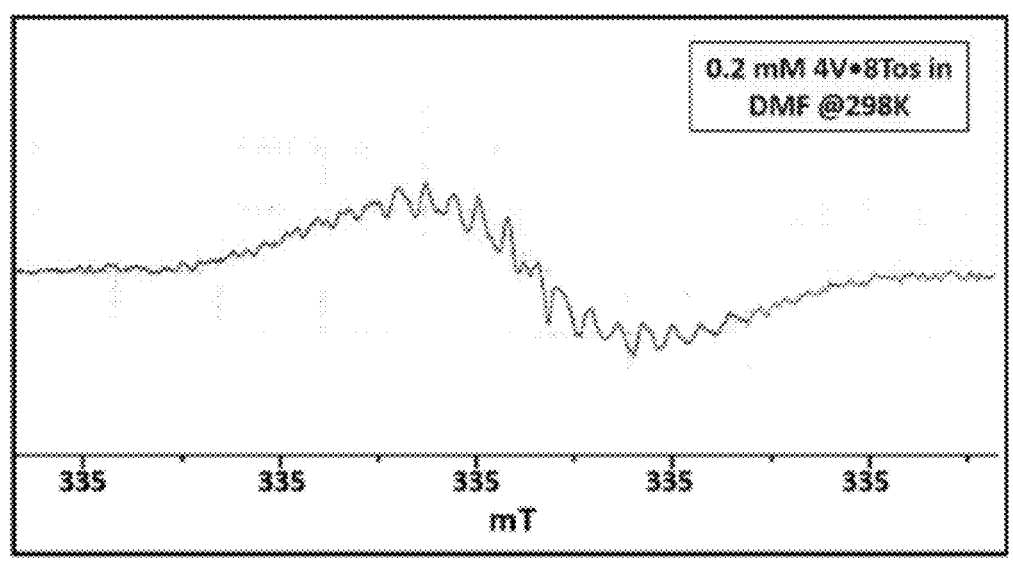
FIG. 11 is the EPR spectrum of 4V·8Tos.

3) Electron Paramagnetic Resonance (EPR) (See e.g., FIG. 11)

4V·8Tos, Hexamer in DMF, 0.2 mM in Dilute Sodium Dithionite

EPR Spectrum: EPR Spectra of a 0.2 mM solution of 4V·8Tos with 0.25 eq. of 0.05 M of sodium dithionite added to generate radical cation state. Experimental parameters are as follows: Modulation Frequency=100 kHz, Modulation Amplitude=1.0 G, sweep time=4 min, time constant=0.03 s, center field=337.160 mT, sweep width=2.5 mT, and microwave power=2 mW.

Example 4: Photoredox-Based Actuation of an Artificial Molecular Muscle

Here, a hydrogel actuation strategy (see e.g., FIG. 12A) is reported that incorporates a blue light (~450 nm) absorbing [Ru(bpy)$_3$]$^{2+}$ photoredox catalyst (and triethanolamine (TEOA) as a sacrificial reductant) in a series of hydrogels composed of 80-100 mol % PEG, 0-20 mol % polyviologen (8V$^{16+}$), and a stoichiometric amount of a tetra-alkyne crosslinker. Irradiation of each hydrogel with blue light (see e.g., FIG. 12B) resulted in a photoinduced electron transfer (PET) from [Ru(bpy)$_3$]$^{2+*}$ to each viologen subunit in the 8V$^{16+}$ chains incorporated into the three-dimensional network. This reduction of 8V$^{16+}$ to 8V$^{8(\cdot+)}$ led to a decrease in electrostatic repulsion, loss of the corresponding counteranions, and intramolecular folding of the polyviologen chains. To determine the ideal concentration of polyviologen needed for optimal actuation performance, the 8V$^{16+}$ molar concentration was increased in each hydrogel from 0 to 5, 10, and 20 mol %, while the PEG molar concentration was decreased from 100 to 95, 90, and 80 mol %. The rate and degree of contraction of each hydrogel was monitored while being irradiated over 5 h, and their mechanical properties were assessed by measuring their respective storage (G') and loss (G") moduli. From these data, the best-performing hydrogel was identified, and the mechanical robustness was evaluated over three contraction-expansion cycles. Lastly, an artificial molecular muscle (AMM) was fabricated by adhering the best-performing hydrogel to black electrical tape attached to a dangling wire bearing a small weight. Irradiation of the AMM with blue light triggered the PET-based contraction of the hydrogel and subsequent bending of the tape, both of which resulted in the lifting of the weight several centimeters from its original starting position.

Results and Discussion

Viologens are a well-known class of redox-active molecules that can accept up to two electrons per viologen, and their ability to enter into radical-radical noncovalent bonding interactions between viologen radical cations (i.e., V$^{\cdot+}$-V$^{\cdot+}$) has been investigated for over half a century. More recently, Stoddart and co-workers exploited this type of radical-based molecular recognition to synthesize molecular switches in the form of rotaxanes and catenanes, as well as artificial molecular pumps.

Our iterative synthetic protocol (see e.g., Scheme 12 and Scheme 13) was modified slightly to prepare grams of the unimolecular 8V$^{16+}$-N$_3$ polyviologen that was used in each of the "click"-based polyviologen-containing hydrogels described in this investigation. Confirmation that PET was feasible between solvated [Ru(bpy)$_3$]$^{2+}$ and 8V$^{16+}$-N$_3$ upon irradiation with blue light was obtained (pre-hydrogel) through optical absorption experiments (see e.g., FIG. 13) that were carried out at low concentrations in H$_2$O. Specifically, a solution containing 0.1 mM polyviologen, 0.15 mM [Ru(bpy)$_3$]Cl$_2$, and 3.0 mM TEOA was prepared and UV-vis-NIR absorption spectra were obtained (see e.g., FIG. 13) before and after 1 h of irradiation with blue light. The diagnostic visible and NIR peaks—indicating radical cation formation and radical-radical pairing, respectively—were observed centered about 500 and 880 nm. Moreover, the absence of either the photocatalyst, polyviologen, or light irradiation resulted in absorption spectra that lacked these specific viologen radical electronic features.

Next, an initial series of hydrogels was prepared using a protocol involving "click" reactions between PEG-N$_3$ (M$_n$=2000 g mol$^{-1}$), 8V$^{16+}$-N$_3$, and a tetra-alkyne crosslinker (see below for general synthetic protocol). The molar ratios between PEG and polyviologen in each hydrogel were chosen (TABLE 1) to steadily increase the redox-responsive component and determine if higher molar amounts of polyviologen (i.e., 0, 5, 10, and 20 mol %) would result in greater rates and degrees of actuation. Once the hydrogels at each polyviologen molar concentration had been synthesized in triplicate, they were swollen in pure H$_2$O, and then brought into a N$_2$-filled glovebox and soaked in a N$_2$-sparged aqueous solution containing 0.15 mM of [Ru(bpy)$_3$]Cl$_2$, and 3.0 mM TEOA for 24 h.

Figures 14A, 14B:
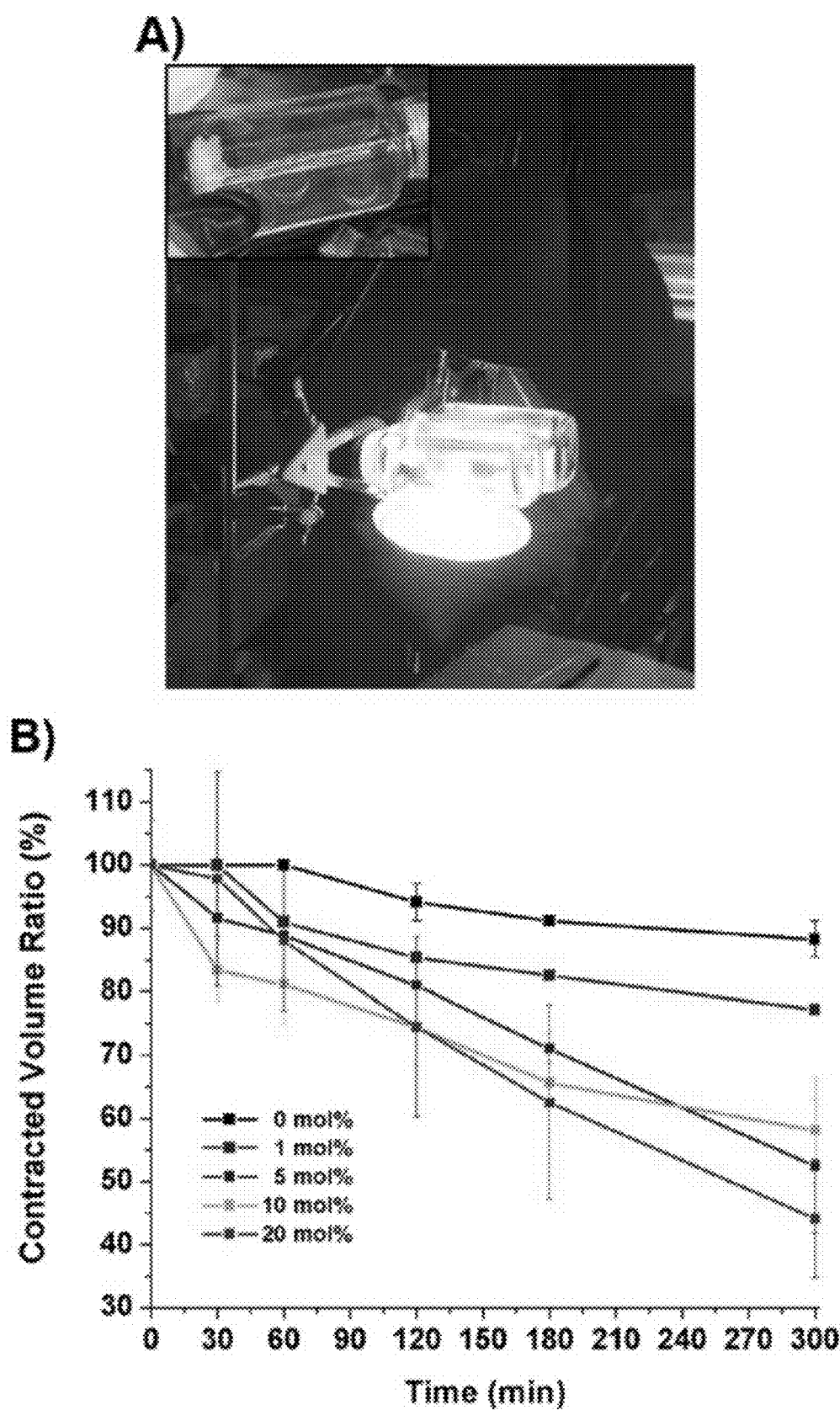
FIG. 14A-FIG. 14B is an image and a graph depicting photoinduced contraction of a series of polyviologen-containing hydrogels.
Figures 15A, 15B:
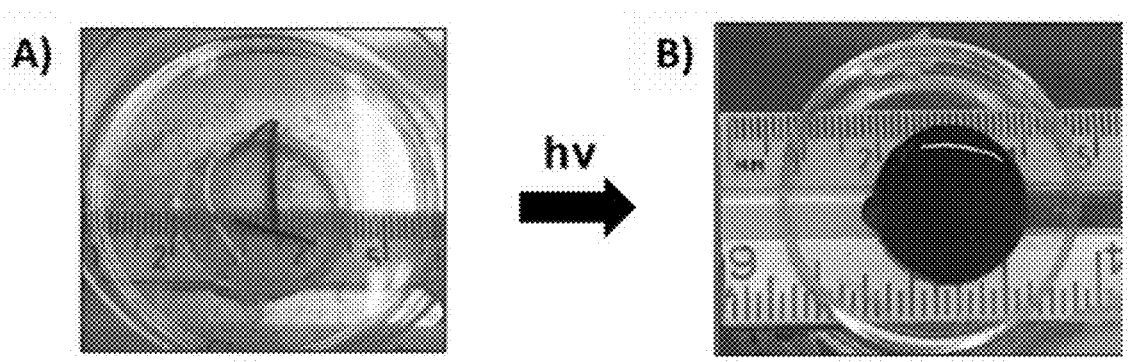
FIG. 15A-FIG. 15B is a series of images and graphs showing polyviologen-containing hydrogels before and after irradiation at ~450 nm.
Figure 16:
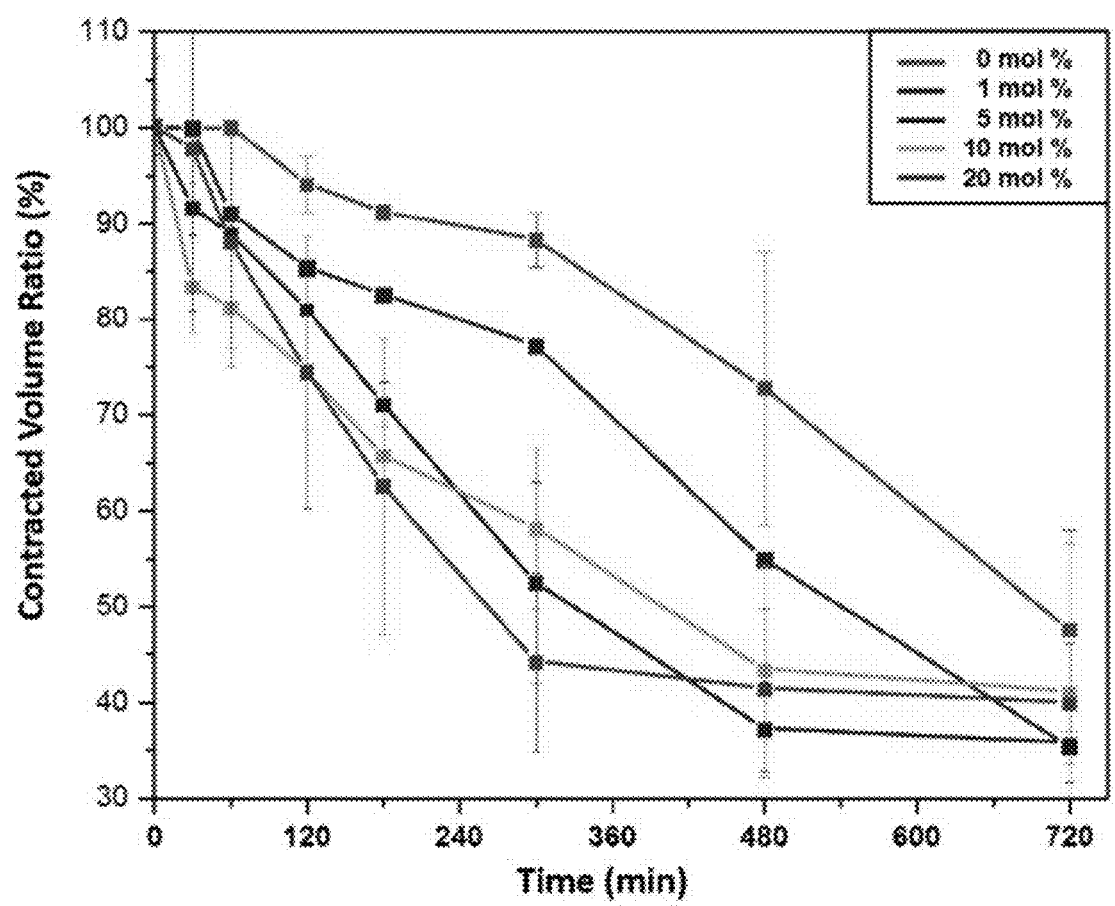
FIG. 16 is a graph showing a full 12 h actuation plot of gels containing different molar equivalents of $8V-N_3.16Tos$. All experiments were performed in triplicate. The actuation plot suggests that the observed contraction in the last seven hours is mostly due to dehydration via factors not associated with the photoredox process, as shown in the large volume loss for the control gel, as well as the plateau for the polyviologen-containing gels.
Figure 19A:
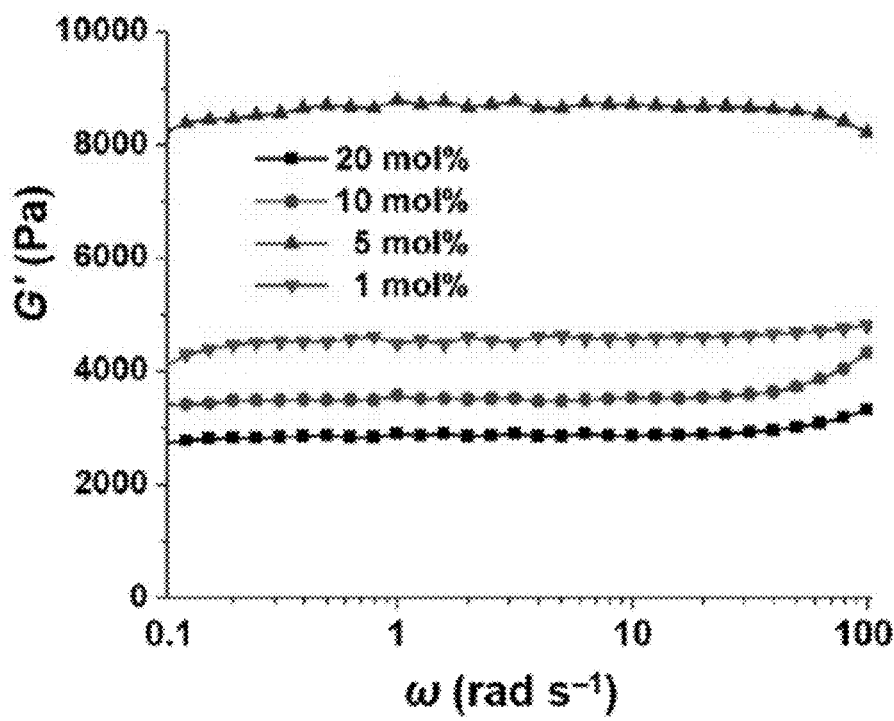
FIG. 19A-FIG. 19B is a series of graphs showing oscillatory shear rheology characterization of polyviologen-containing hydrogels.
Figure 19B:
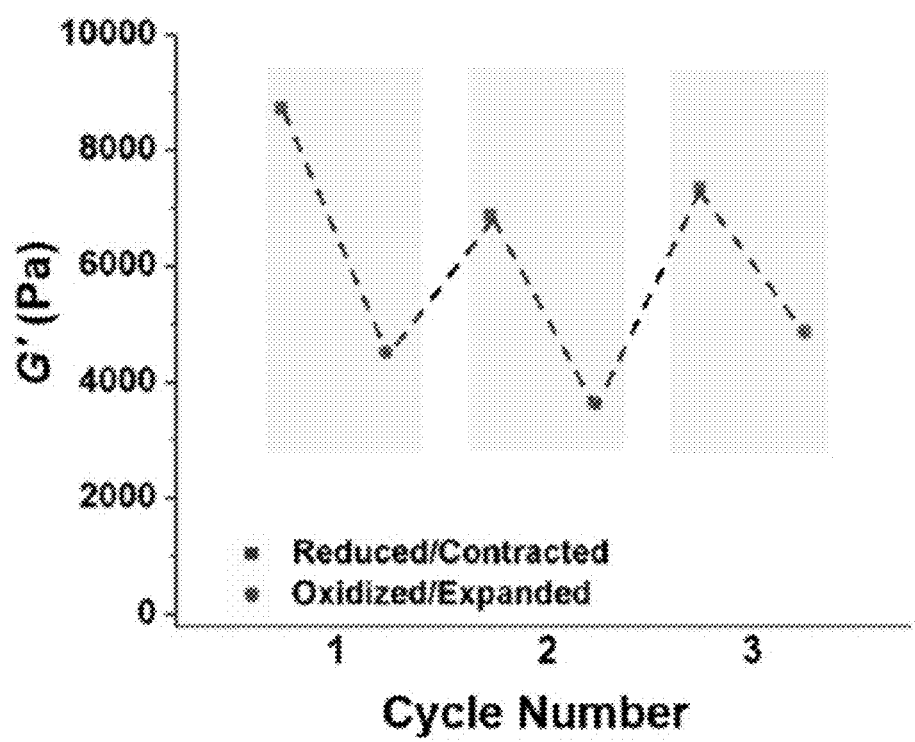

After reaching saturation, each set of hydrogels was removed from the "photoredox" solution and placed inside clear glass jars (see e.g., FIG. 14, inset image). Each jar contained a damp Kimwipe at its base to maintain humidity inside the jar and mitigate any potential dehydration of the hydrogels while in the arid glovebox environment. Then, the glass jars were sealed with black electrical tape and parafilm and clamped in between two desk lamps equipped with blue LED bulbs (see e.g., FIG. 14). Irradiation with blue light from above and below the hydrogel-containing glass jar was initiated, and the volumes of each hydrogel were measured at 0, 30, 60, 120, 180, and 300 min by removing them temporarily from the glass jar and measuring with a caliper. As expected for the polyviologen-containing hydrogels, their yellow color appears black after irradiation (see e.g., FIG. 15), which results in a change from translucent to opaque, followed by a decrease in overall volume. The rate of contraction for each irradiated hydrogel is plotted in FIG. 14 as the percent contracted volume ratio (final/initial volume) for each molar concentration of the polyviologen-containing hydrogels, where the error bars represent the standard error of the mean from the three samples prepared at each concentration. Analysis of the control data, where no polyviologen was present in the hydrogel (i.e., 0 mol %), reveals that an approximate 10% loss in volume is observed under the current experimental conditions and may be attributed to dehydration during the first 5 h of irradiation (see also FIG. 19 which shows full window over 12 h of irradiation). This dehydration could potentially occur as a result of low levels of heating caused by the incident blue light, in addition to brief exposure of the hydrogel to the arid glovebox environment each time the hydrogels were removed from the jars and their respective volumes measured. However, incorporation of 1 mol % 8V$^{16+}$ (99 mol % PEG) resulted in a loss in average hydrogel volume of 22% over the 5 h experiment. Moving to higher concentrations of polyviologen—specifically 5, 10, and 20 mol %—resulted in greater contracted volume ratios, where the 20 mol % 8V$^{16+}$-containing hydrogels exhibited a volume loss of ~65% after 5 h of irradiation. Although the latter result suggests a direct correlation between polyviologen concentration and contracted volume ratios, comparison of the data in FIG. 14 for the 5, 10, and 20 mol % polyviologen-containing hydrogels reveal no statistical difference between the datasets. It was hypothesized this lack of distinction in performance between the contracted volume ratios was related to the mechanical properties of each set of hydrogels since it was observed by hand that the 20 mol % hydrogels were frail and brittle compared to the 5 mol % ones, which are more robust and easier to handle physically.

Figure 17:
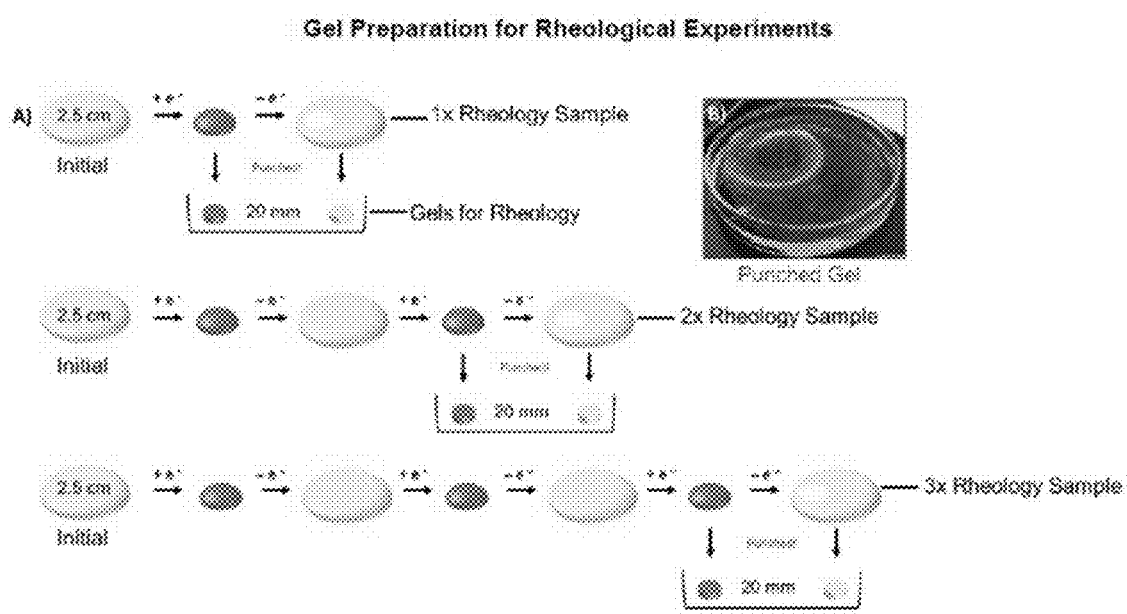
FIG. 17 shows the gel preparation for rheological experiments. A) Flowchart denoting the cycling process. Cycling only done on 5 mol % samples. B) Water solution tinted yellow as ruthenium-based photocatalyst diffuses out of a re-oxidizing gel, which demonstrates the need to diffuse fresh ruthenium photocatalyst into gel matrix with each irradiation cycle.

To quantify the differences in mechanical strength between each of the polyviologen-containing hydrogels, oscillatory shear rheology experiments were carried out on both contracted and expanded hydrogels that were obtained by "punching" out disc-shaped gels 20 mm in diameter after they had been irradiated for 5 h or had been re-swollen in $O_2$-saturated $H_2O$, respectively. Each rheological experiment consisted of frequency sweeps from 0.1 to 100 rad $s^{-1}$, while keeping the strain amplitude constant at 1%. See Supporting Information for more detail on hydrogel preparation (see e.g., FIG. 17), as well as for full plots of G' and G" for each set of contracted and expanded hydrogels (see e.g., FIG. 18). FIG. 19 shows a plot of storage moduli (G) for irradiated hydrogels that contained either 1, 5, 10, or 20 mol % polyviologen. The 20 mol % polyviologen-containing hydrogels (black squares, FIG. 19) exhibit the lowest storage moduli (2800 Pa) of all the molar concentrations, whereas the G' value for the hydrogels that contained 5 mol % polyviologen (purple triangles, FIG. 19) was nearly three times higher at ~8300 Pa. It is also interesting to note that the G' value (~3400 Pa) for the 10 mol % polyviologen-containing hydrogels is comparable to that of the 20 mol % dataset, and that the 1 mol % hydrogels possess higher storage moduli (~4400 Pa) than both the 10 and 20 mol % polyviologen-containing hydrogels. In other words, although higher concentrations of polyviologen in the hydrogel were expected to lead to greater losses in volume, incorporation of 10 or 20 mol % $8V^{16+}$ in the three-dimensional polymer network resulted in a weakening of the material, which affected the hydrogel's overall performance. Moreover, the storage moduli for the 1 mol % $8V^{16+}$-containing hydrogel falls in between that of the 5 and the 10/20 mol % datasets, a position which may be attributed to its decreased ability to contract on account of the small concentration of polyviologen present in the material.

Collectively, the quantitative assessment of performance for each set of hydrogels—in terms of contraction rates, total volume loss, and mechanical strength as a function of polyviologen concentration—allowed for the identification of the 5 mol % $8V^{16+}$-containing hydrogel as the optimal or best-performing composition. To further assess the mechanical performance of the 5 mol % $8V^{16+}$-containing hydrogels, three separate gels were synthesized (see FIG. 17), and carried through either one, two, or three contraction-expansion cycles before being "punched" into 20 mm discs, and their shear moduli measured. As expected, re-swelling of the contracted hydrogels in $O_2$-saturated $H_2O$ led to oxidation/expansion of the material and storage moduli (see e.g., FIG. 19B) that are nearly half the value obtained for the contracted hydrogels. Additionally, the mechanical robustness of each hydrogel was assessed (see e.g., FIG. 19B) as a function of cycle number (i.e., 1×, 2×, or 3× cycles) by again measuring the storage moduli of each sample. Even though the oxidized (red spheres) and reduced (purple squares) states show some variability in the absolute G' values exhibited over the three cycles (see e.g., FIG. 19), the magnitude of each remains 2-3 times higher than the storage moduli corresponding to the 1, 10, and 20 mol % polyviologen-containing hydrogels, and thus illustrates the superior performance of the 5 mol % $8V^{16+}$-containing hydrogels.

Figure 20:
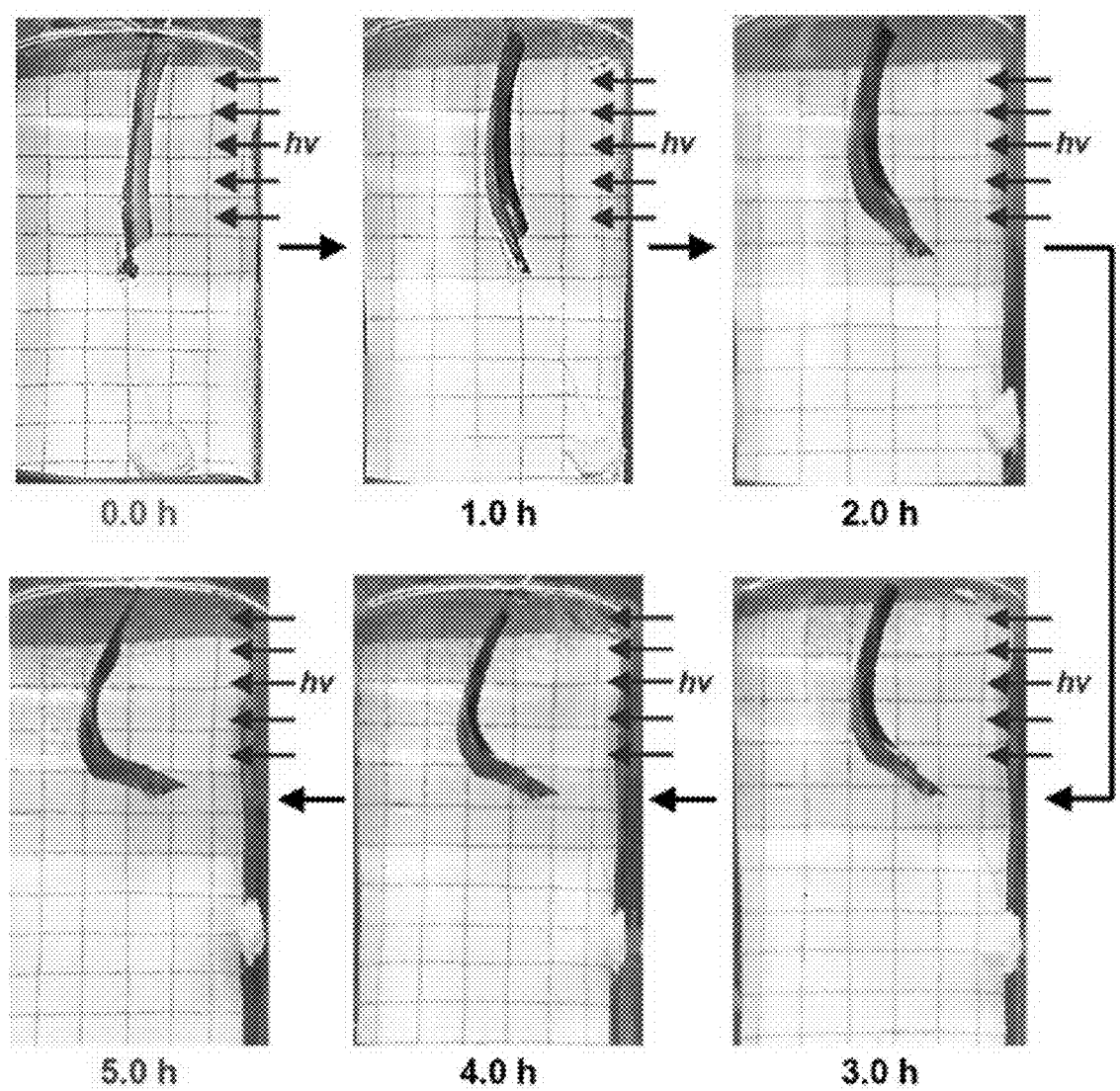
FIG. 20 is a series of images of an artificial molecular muscle (AMM) fabricated by adhering a 5 mol % 8V16+-containing hydrogel to black electrical tape, which was then affixed to the cap of a glass jar before being placed in a $N_2$-filled glovebox. The hydrogel was doped with the ruthenium-based photocatalyst and sacrificial reductant and a small weight in the form of a connecting aluminum wire and a 20.0 mg sponge was attached to one end of the tape. Irradiation of the AMM with blue light quickly changed the color of the hydrogel from a yellowish-orange to appearing almost black. PET-based actuation of the hydrogel, bending of the support tape, and the amount of work being done was monitored for 5 h (while irradiating from the right, blue arrows). After 5 h, the weight was moved several centimeters from its starting position. Note, the grid boxes in the background represent 0.635 cm on each side, and the network polymer mass in the hydrogel is 19.0 mg, whereas the fully swollen hydrogel weighs 503.0 mg.
Figure 21:
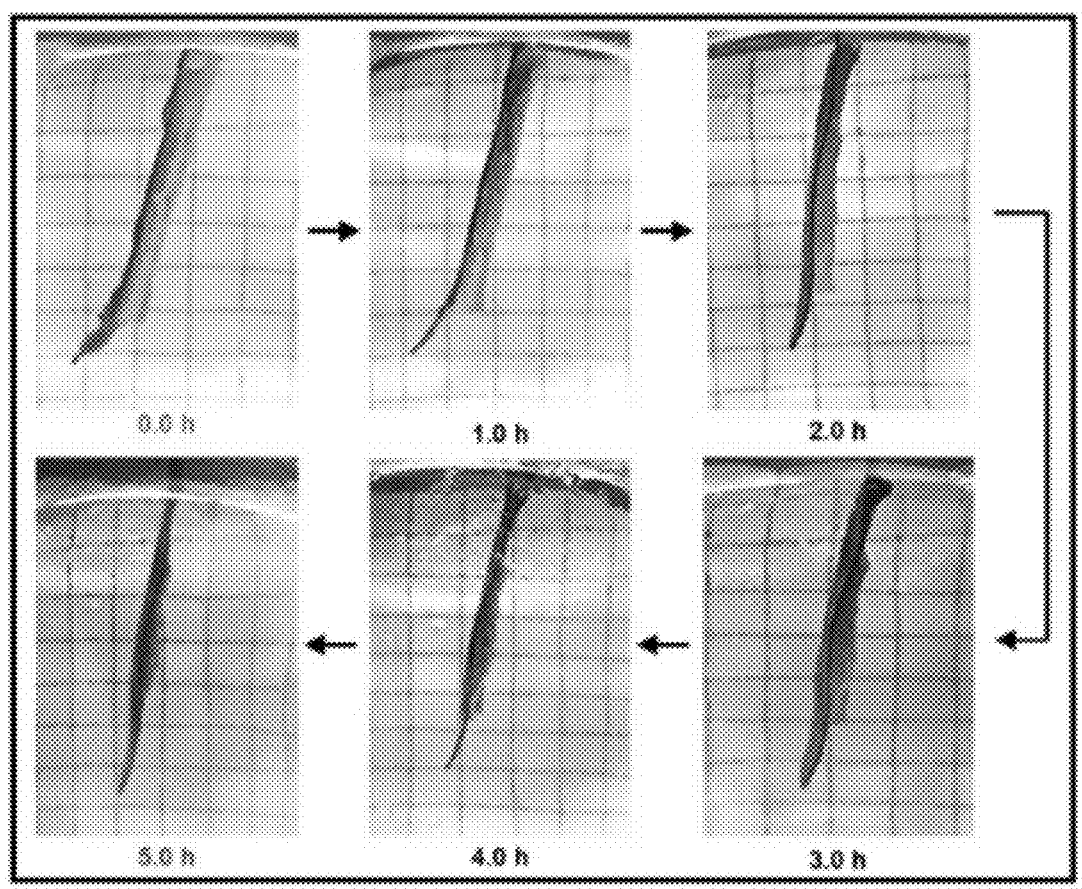
FIG. 21 is a series of images showing a tape bending control experiment, no photoredox catalyst: A 5 mol % polyviologen-containing gel swollen with water only was irradiated with ~450 nm light over a period of 5 h (i.e., no photocatalyst). The gel shows dehydration on the side nearest to the light source, but no tape bending is observed.
Figure 22:
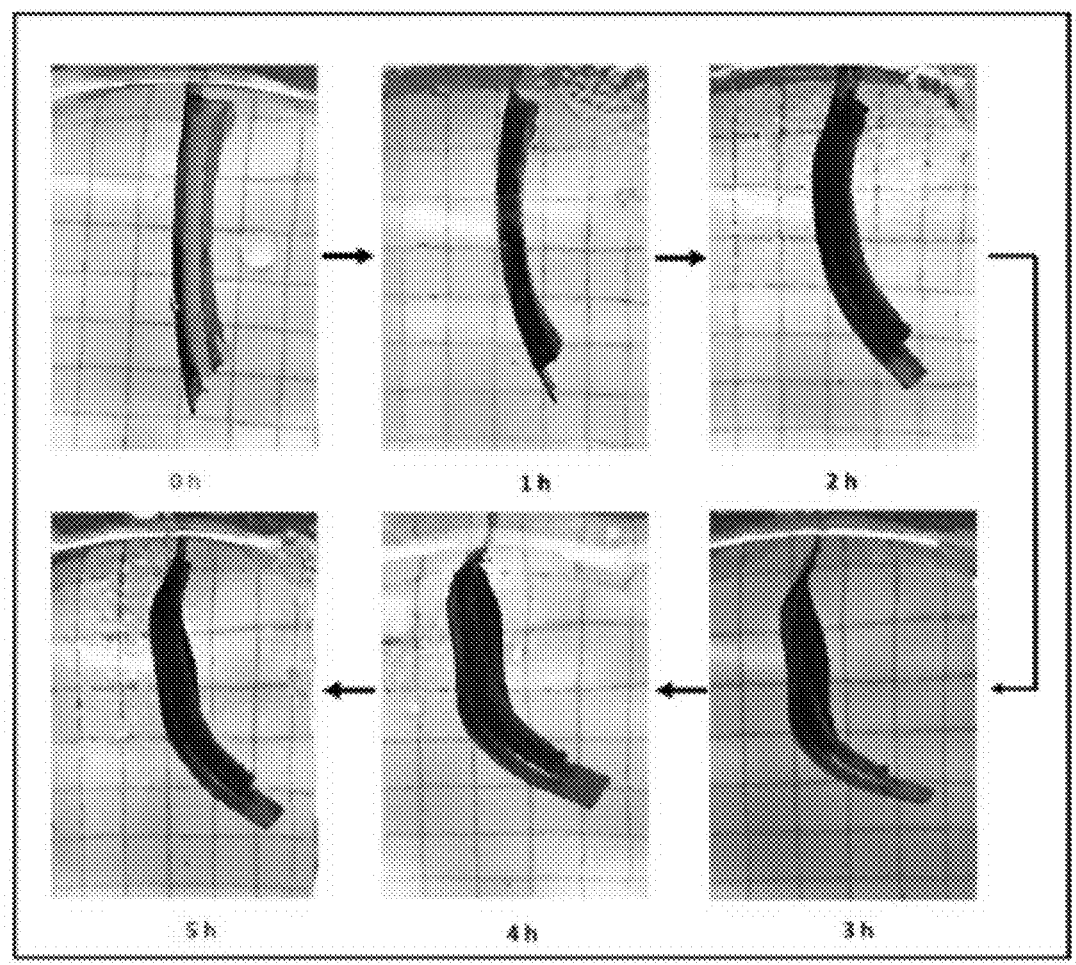
FIG. 22 is a series of images showing a tape bending experiment with photoredox catalyst: A 5 mol % polyviologen-containing gel swollen in "photoredox" solution was irradiated with ~450 nm light over a period of 5 h. Due to the photoinduced actuation process, the gel decreased in volume in all directions, which caused the tape to curl. Also, significant bending and reduction in size can be observed within the first hour of irradiation in contrast to the control gel where no observable change in gel volume is observed.

To demonstrate the redox-responsive hydrogel's ability to do work, an AMM was fabricated on the benchtop by adhering a 0.4 (w)×0.4 (h)×3.1 (l) cm rectangular strip of 5 mol % $8V^{16+}$-containing hydrogel (503.0 mg swollen) to the non-sticky side of a piece of electrical tape via the use of commercial superglue (see Supporting Information for further details on AMM fabrication). Adherence of the hydrogel to the supporting tape occurred in less than 1 min under these conditions, and afterwards excess tape was cut away, such that its width matched that of the rectangular hydrogel, while still leaving ~2 cm of tape exposed at each end. Next, the AMM was moved inside the $N_2$-filled glovebox, and soaked for 24 h in the "photoredox" solution containing the ruthenium-based photocatalyst and sacrificial reductant. Then, one end of the AMM was affixed to a glass jar cap using epoxy resin, and the other end was tethered via aluminum wire to a small sponge weighing exactly 20.0 mg. At t=0 h (see e.g., FIG. 20, upper left image), the "loaded" AMM is nearly linear as it hangs inside the glass jar. Irradiation from the right side of the AMM, as indicated by the blue arrows in FIG. 20, initiated the PET process, which resulted in a change in color of the hydrogel from yellowish-orange to black within the first 30 min. After 1 h of irradiation with blue light, a slight bending of the AMM and a shift in the position of the weight was observed (FIG. 20, top middle image). Further bending of the AMM continued in conjunction with light irradiation, and after 5 h (FIG. 20, bottom left image), the AMM adopts a nearly 90° angle and the weight has been moved ~1.25 cm to the right and 1.91 cm up (as determined using the background grid). The polymer fraction of the hydrogel used in the AMM was 19.0 mg and the mass of the sponge was 20.0 mg. The results of this experiment show how the as-fabricated AMM is capable of lifting a mass at roughly equal to its own weight. Attempts to lift a weight that was five times heavier than the mass of the polymer in the hydrogel (i.e., ~100 mg) proved to be ineffective, however, this result was not surprising since PEG is a soft material. Further evidence that supports the PET-based mechanism of actuation in the AMM was obtained by performing a control experiment (see e.g., FIG. 21), where an identical AMM was prepared, except in this case it was soaked in $H_2O$ only, i.e., no "photoredox" solution. Irradiation of this control AMM resulted in little to no bending, and only some dehydration of the hydrogel was observed. Furthermore, to prove that AMM fabrication and its light-triggered bending are reproducible, another 5 mol % $8V^{18+}$- containing hydrogel was incorporated into a tape-based AMM (except with no weight attached), and the material was monitored over 5 h while irradiated with blue light (see e.g., FIG. 22). As expected, the light-activated polyviologen-containing hydrogel turned black in color and contracted causing the adhered tape support to bend, similarly as the "loaded" AMM experiment.

Figure 23:
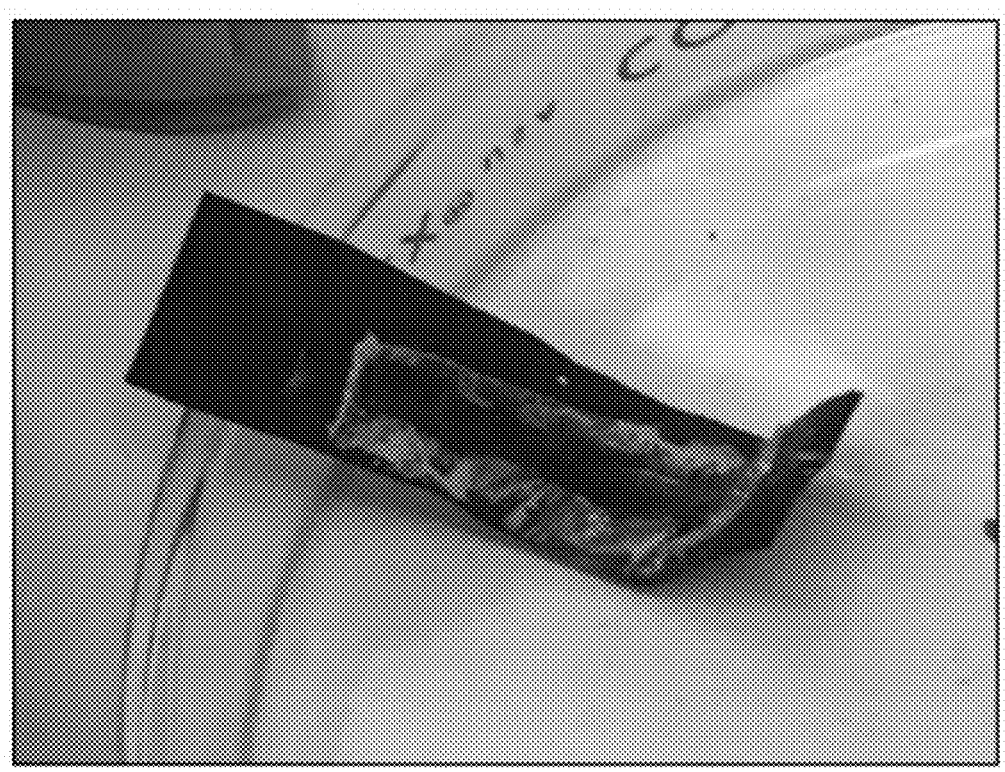
FIG. 23 is an image of a polyviologen-containing hydrogel adhered to black electrical tape following a bending experiment. The gel lost some of its structural integrity, while leaving a white glue residue where it had been previously adhered.
Figure 24A:
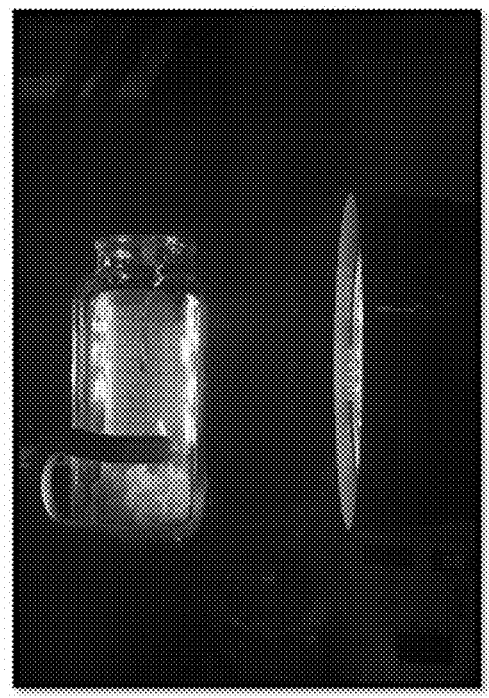
FIG. 24A-FIG. 24B is an image of the Photo-irradiation Experimental Setup.
Figure 24B:
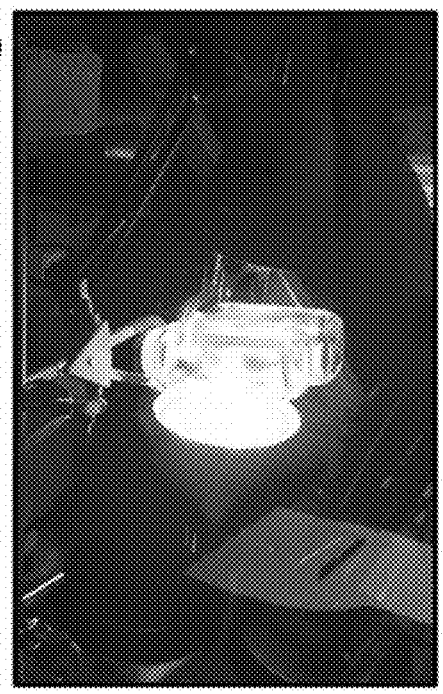

The results from these prototype experiments are highly encouraging since the successful demonstration of reproducible AMM fabrication, light-activated actuation, and work being performed using a redox-responsive hydrogel composed of mostly PEG and low molar concentrations of the electroactive polyviologen. However, the system, as constructed, is not without limitation. For example, after the AMM has been irradiated and bent, the hydrogel component is somewhat damaged (see e.g., FIG. 23) as a consequence of the stronger superglue-based poly(cyanoacrylate) network that forms at the interface between the tape support and the PEG-based hydrogel. Thus, the light-activated contraction of the redox-responsive hydrogel causes parts of the soft material to slough off and stick to the glue residue that is left behind. This degradative pathway limits the reversibility of the polyviologen-containing hydrogel when it is adhered to a substrate of different composition. Nonetheless, this prototype lays the foundation for future development of more robust AMMs.

CONCLUSION

Here, a novel photoredox-based mechanism is described that was used to actuate a series of PEG-based hydrogels that contained increasing concentrations of a unimolecular and electroactive polyviologen consisting of eight viologen subunits ($8V^{16+}$). Reduction of the $8V^{16+}$ chains to $8V^{8(\cdot+)}$ by way of photoinduced electron transfer (PET), followed by contraction of the hydrogel was made possible by doping in an excess of visible-light-absorbing photoredox catalyst and sacrificial reductant—i.e., $[Ru(bpy)_3]^{2+}$ and triethanolamine, respectively. Irradiation of the redox-responsive hydrogels with blue light over the course of 5 h resulted in contracted volume ratios approaching ~35% in the hydrogels that possessed higher molar concentrations of polyviologen. A general trend was observed in terms of polyviologen concentration, where the contracted hydrogels composed of 10 or 20 mol % polyviologen were more fragile by a factor of three than hydrogels consisting of 5 mol % polyviologen—as quantified by oscillatory shear rheology. Based on this, three contraction-expansion cycles were performed for the 5 mol % polyviologen-containing hydrogels and the shear moduli (G' and G') were measured after each contraction and expansion to demonstrate mechanical consistency over several cycles. Lastly, an artificial molecular muscle prototype was fabricated using the best-performing hydrogel composition, and its ability to perform work while being irradiated was assessed by lifting a weight with mass nearly equal to that of the total polymer found in the redox-responsive hydrogel. This type of visible-light-triggered actuation can be used in a variety of potential applications, such as drug delivery, soft robotics, or wearable light-powered devices.

Materials/Synthesis Protocols/Instrumentation

All reagents were purchased from commercial suppliers and used without further purification unless stated otherwise. Literature procedures were used in the synthesis of hexaethylene glycol di-p-toluenesulfonate (HEG-Tos), 2-[2-(2-Azidoethoxy)ethoxy]ethyl-4-methylbenzenesulfonate (Tos-DEG-N3), O,O'-Bis(2-azidoethyl)polyethylene glycol ($M_n$=2000) (PEG-N$_3$), tetrakis(2-propynyloxymethyl)methane (TAXL). The protocol for the synthesis of 8V·14Tos and the azide-capped polyviologen 8V-N$_3$·16Tos, was followed via the previously published procedure, however an updated procedure demonstrating a large scale synthesis of 8V-N$_3$·16Tos is below. All photochemical reductions of polyviologen-containing hydrogels were performed under an inert atmosphere of UHP nitrogen to prevent premature re-oxidation and were encapsulated in a humid environment to mitigate dehydration. Photochemical experiments were performed using two Hampton Bay desk lamps with ABI LED Aquarium Light Bulbs (12 Watt/750 Lumens ea.). Ultraviolet-Visible-Near Infrared (UV-vis-NIR) absorbance spectra were recorded on an Agilent Cary 5000 spectrophotometer with a PbSmart NIR detector. Frequency sweep (1.0% strain, 0.1 to 100 rad s$^{-1}$) and strain sweep (10 rad s$^{-1}$, 0-200% strain) rheology experiments were carried out using a TA AR-G2 oscillatory shear rheometer with a 20 mm smooth geometry.

1) Scheme 12 Depicting the Iterative Synthesis of Polyviologen Cross-Linkers

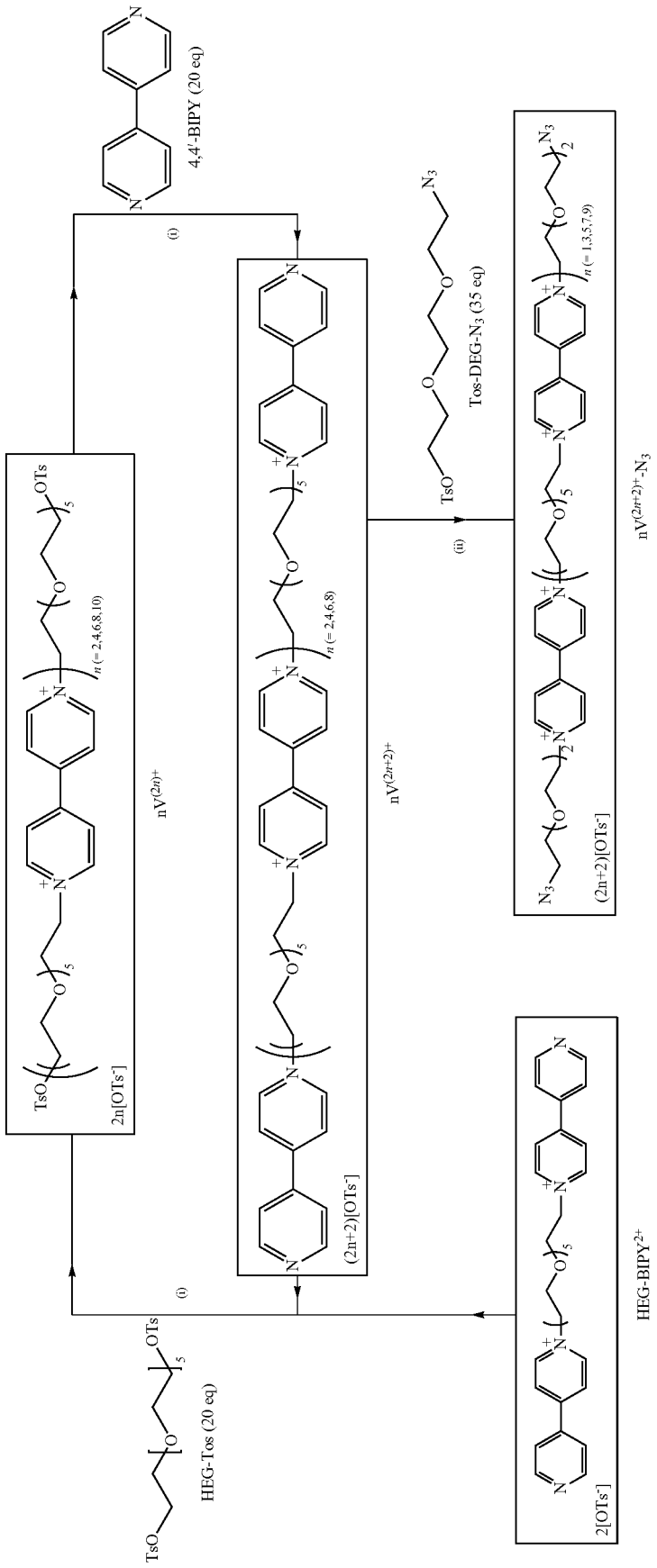

Scheme 12. An iterative synthesis was used to prepare 8V·16Tos polyviologen by (i) alternating between the excessive addition (20 equiv) of tosyl end-capped hexaethylene glycol (HEG-Tos) and 4,4′-bipyridine (BIPY) in MeCN at 130° C. for 12-16 h in a closed reaction vessel. The synthetic cycle begins (green box) with a BIPY end-capped HEG (HEG-BIPY$^{2+}$), and the oligomer $i$ is grown iteratively, with only intermittent precipitations in MeCN:PhMe, followed by centrifugation in order to isolate each product. The BIPY end-capped precursor, 8V·14Tos can be removed and (ii) functionalized with terminal azide groups (red box) through the excessive addition (35 equiv, MeCN, 130° C., 20 h) of a tosylated diethylene glycol possessing one azide at its terminus (Tos-DEG-N$_3$).

2) Scheme 13 Depicting the Large-Scale Synthesis of 8V-N3·16Tos.

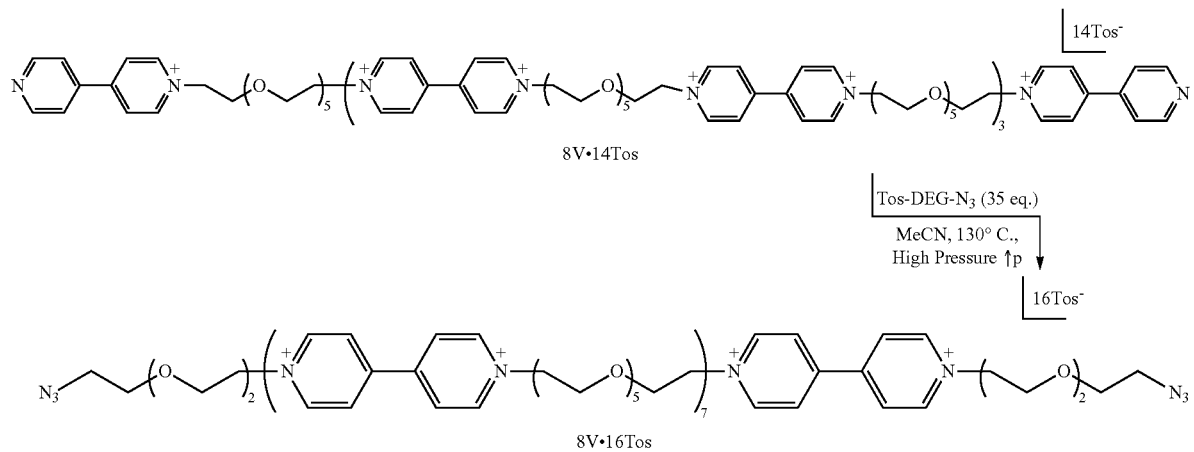

Scheme 13. Large-scale Synthesis of 8V-N₃•16Tos: A 100mL thick walled high-pressure flask with Teflon screw cap and stir bar was charged with 8V•14Tos (0.860 g, 0.170 mmol), Tos-DEG-N₃ (1.927 g, 5.57 mmol), and MeCN (30 mL). The flask was capped tightly, and the mixture was stirred at high-pressure at 130° C. for 24 h. After 24 h, the reaction mixture was cooled to room temperature and the crude golden-brown mixture was transferred evenly to four 50 mL plastic centrifuge tubes and methanol (10 mL) was used to rinse any remaining material out of the reaction flask and evenly distributed among the four centrifuge tubes. PhMe (35 mL) was then added to the tubes to precipitate the pure product as a sticky brown oil. To assist in the precipitation and purification of the product the MeCN/PhMe mixture was centrifuged twice at 4490 rpm at -10° C. for 35 min, replacing the supernatant with fresh PhMe between runs. To maximize yields the MeCN/PhMe supernatant should be concentrated under reduced pressure and centrifuged a third time at identical conditions (1.48 g, 97%).

Kinetics

1) General Procedure for the Preparation of Polyviologen-Containing "Click" Hydrogels 8V-N3·16Tos, PEG-N3, and TAXL were weighed into a glass scintillation vial in appropriate ratios depending on the mole percent of the desired product (see TABLE 1) and dissolved in DMF (0.6 mL). Then, CuSO4 (7.2 mg, 0.046 mmol) and sodium ascorbate (4.6 mg, 0.046 mmol) were added to two separate 2-dram vials and each were dissolved in deionized water (0.2 mL). The CuSO4 solution was then added via syringe to the solution of polymer/TAXL and vortexed for 5-10 seconds turning the solution a pale green color. The solution of sodium ascorbate was then slowly added to the pre-gel mixture and vortexed for another 5-10 seconds to ensure even distribution, a process which turned the solution a bright yellow. The gel mixture was then rapidly distributed by syringe into three separate 1 cm diameter Teflon molds. The gelation process was complete after approximately 30 min and the hydrogels were then transferred and swollen in an aqueous solution of ethyenediaminetetraacetic acid (EDTA) (0.05 M) overnight to remove excess copper ions remaining in the hydrogel. After swelling, the hydrogels were transferred to a fresh solution of DI water to wash the hydrogels and complete the swelling process.

TABLE 1

Total Molar Amounts for 8V-N3•16Tos/PEG-N3/TAXL Containing Hydrogels

| Mole Percent (mol %) of 8V-N₃•16Tos | Moles of 8V-N₃•16Tos | Moles of PEG-N₃ | Moles of TAXL |
|---|---|---|---|
| 0 | 0.00 | $9.4 \times 10^{-5}$ | $4.6 \times 10^{-5}$ |
| 1 | $9.5 \times 10^{-7}$ | $9.3 \times 10^{-5}$ | $4.6 \times 10^{-5}$ |
| 5 | $4.6 \times 10^{-6}$ | $9.0 \times 10^{-5}$ | $4.6 \times 10^{-5}$ |
| 10 | $9.2 \times 10^{-6}$ | $8.4 \times 10^{-5}$ | $4.6 \times 10^{-5}$ |
| 20 | $1.8 \times 10^{-5}$ | $7.6 \times 10^{-5}$ | $4.6 \times 10^{-5}$ |

2) General Procedure for the Photoredox Activation of Polyviologen-Containing "Click" Hydrogels Photoredox Activation Kinetics Protocol: Kinetics experiments were performed in triplicate, on gels containing 1, 5, 10, and 20 mol % polyviologen. The gels were fabricated, purified, and swollen in fresh H₂O. The gels were then brought into an inert nitrogen glovebox environment and soaked for 24 h in a degassed aqueous "photoredox" solution containing [Ru(bpy)₃]C12 (0.15 mM) and TEOA (3.0 mM) to serve as the photoredox catalyst and sacrificial electron donor, respectively. The gels were then removed from solution and placed in a Kimble™ 8 oz. French Square bottle. A water-soaked Kimwipe was also placed inside the bottle to provide ambient moisture. The lid of the bottle was covered in parafilm followed by electrical tape to prevent moisture escaping into the arid glovebox atmosphere. A PEG-only hydrogel was also soaked in the "photoredox" solution and similarly placed inside of a glass container containing a moist Kimwipe to serve as a control. The two bottles, experimental and control, were suspended and irradiated with ~450 nm light from the top and bottom, maintaining a 5 cm distance between the gel and the light source at all times. The gels were irradiated for 12 h with diameter and height measurements taken at regular intervals. After irradiation, the gels were transferred to a fresh DI water solution in atmosphere to re-oxidize and swell.

Rheological Protocols and Mechanical Properties

1) Polyviologen-Containing Gel Rheology Protocol

Gels were fabricated as stated previously. Gel solution was poured into a 2 cm diameter circular mold and allowed to set. The gels were then removed from the mold and submerged in EDTA solution [0.5 mM] and fresh solution was replaced until it was colorless. Each gel was placed in a 3.5 cm petri dish and brought into the glove box, where it was soaked in "photoredox" solution for 12 h. A water-soaked Kimwipe was then added to the petri dish, parafilmed, and taped close. The gels were then irradiated for 5 h from the top and bottom with ~450 nm light, removed from the light source, and a disc was punched out of the material 20 mm in diameter. The gel discs were placed into an airtight container, parafilmed and taped and rheological experiments were performed to obtain the reduced polyviologen-containing hydrogel data. The remaining gel material was removed from the nitrogen atmosphere and placed in DI water to re-oxidize and swell. The oxidized rheological data were then taken from a 20 mm disc gel sample that had been reduced once followed by re-oxidation. The 5 mol % gels were cycled to determine mechanical strength over multiple contractions. A single cycle is defined by photochemical reduction under UHP nitrogen followed by re-oxidation in atmosphere, returning it to the fully oxidized state.

Figures 18A, 18B, 18C, 18D:
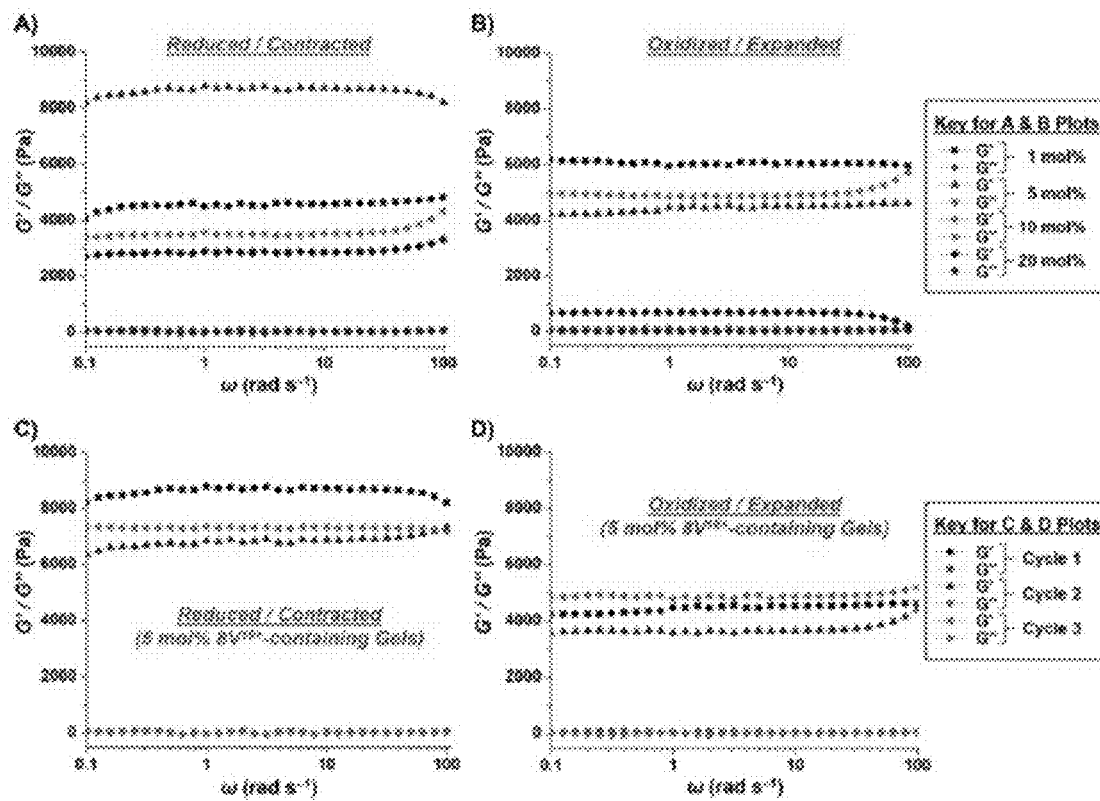
FIG. 18A-FIG. 18D is a series of graphs showing full rheological characterization of 1, 5, 10, 20 mol % Polyviologen-containing Hydrogels. The dynamic viscoelastic behavior of polyviologen-containing hydrogels composed of 1, 5, 10, and 20 mol % $8V-N_3.16Tos$-A) in their contracted and B) expanded states—was assessed by oscillatory shear rheometry. Each mole percent was synthesized in a 4.5 cm (diameter) petri dish, followed by reduction/contraction to approximately 2.5 cm and using a punch-out tool to obtain 20 mm diameter samples that matched the instrument geometry. A cycling experiment was also performed on 5 mol % gels, similarly prepared, where the storage and loss moduli were determined after C) one, two, and three reductions and D) oxidation cycles. The rheology experiments consisted of frequency sweeps from 0.1 to 100 rad $s^{-1}$ for all samples while keeping the strain amplitude constant at 1%. At no point during the course of the experiment is a cross-over point observed between the storage (G') and loss (G") moduli; an outcome which indicates elastic behavior at all angular frequencies.

2) Full Rheological Characterization of 1, 5, 10, 20 Mol % Polyviologen-Containing Hydrogels (See e.g., FIG. 18)

Gel-to-Tape Adherence Protocol and Additional Bending Experiments

1) General Protocol for Adhering Polyviologen-Containing Gel to Black Electrical Tape A strip of fully swollen polyviologen-containing gel was cut using a precision cutting tool to approximately 0.4 cm×0.4 cm×3.1 cm with an approximate mass of 503.0 mg. The excess moisture was gently dabbed away using a cotton tipped swab, while two 3.5 cm strips of black electrical tape were cut and pressed together with the adhesive sides turned inward to form one sturdy support. The black electrical tape support was then left under a flat heavy weight for 5 min to ensure that the support was straight and flat before gel adherence. Then, super glue was poured into a dish and a cotton tipped swab was thoroughly saturated in the glue and which was then applied to the portion of the tape where the gel was to be adhered. The glue was allowed to sit for 10 s to become slightly tacky and the strip of polyviologen-containing gel was carefully placed on top of the glue using forceps and positioned so that it was as straight as possible leaving 2 cm of tape exposed at the head and tail of the gel. Additional glue was then very quickly and carefully added to the outer edges of the gel to ensure that they were properly adhered. The adhesion of the gel to the tape was complete in approximately 1 min. Afterwards, the sides of the tape were cut to match the width of the hydrogel and the gel was then soaked in "photoredox" solution if the gel was to be activated photochemically, or in fresh DI water if the gel was to serve as a control experiment to monitor dehydration.

Figures 25A, 25B:
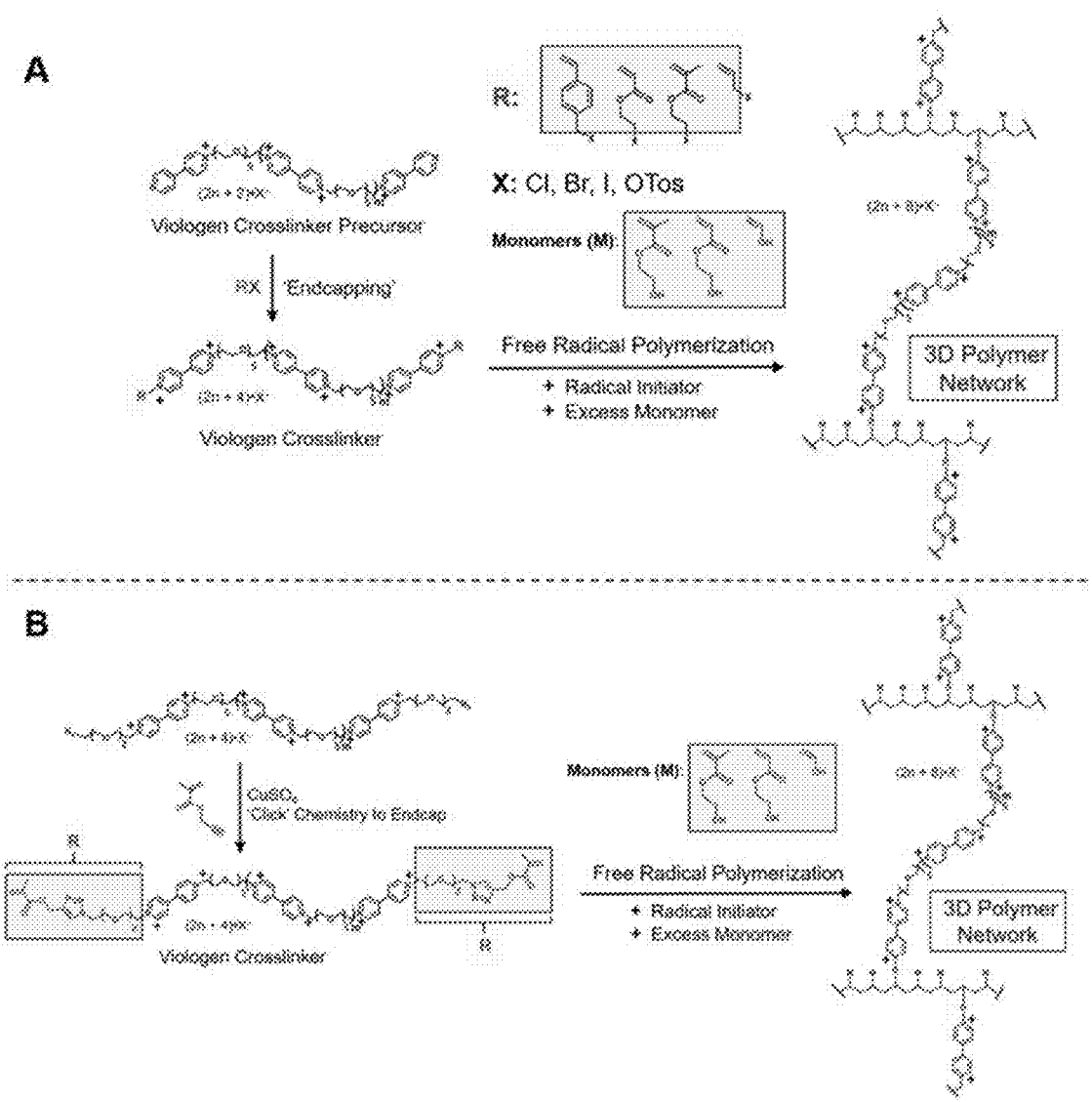
FIG. 25A-FIG. 25B is a series of schemes showing the functionalization of the pyridyl end groups of polyviologen-based crosslinker precursors either through nucleophilic substitution of leaving groups attached to acrylate or vinyl groups (A) or through copper-mediated 'click' chemistry of alkyne-functionalized acrylates (B). In each case, the synthesis of polystyrene- and polyacrylate-based polymers can be achieved through free radical polymerization in the presence of excess styrene or acrylate monomers.

Example 5: Alternative Synthetic Methodologies Towards Stronger and Tougher Polyviologen-Based Actuators Functionalization of the pyridyl end groups of polyviologen-based crosslinker precursors—either through nucleophilic substitution of leaving groups attached to acrylate or vinyl groups (see e.g., FIG. 25A) or through copper-mediated 'click' chemistry of alkyne-functionalized acrylates (see e.g., FIG. 25B)—can be readily achieved to convert polyviologens into difunctional cross-linkers. The resultant polyviologen cross-linkers are readily polymerized in the presence of a radical initiator and excess quantities of commercial acrylate- and vinyl-based monomers to generate a three-dimensional crosslinked polymer network, where the polymer chains in between each crosslinking junction are formed in situ and are crosslinked upon reaction with polyviologen crosslinker.

Example 6: Faster and Scaled Synthesis of Redox-Active Polyviologens

Figure 26:
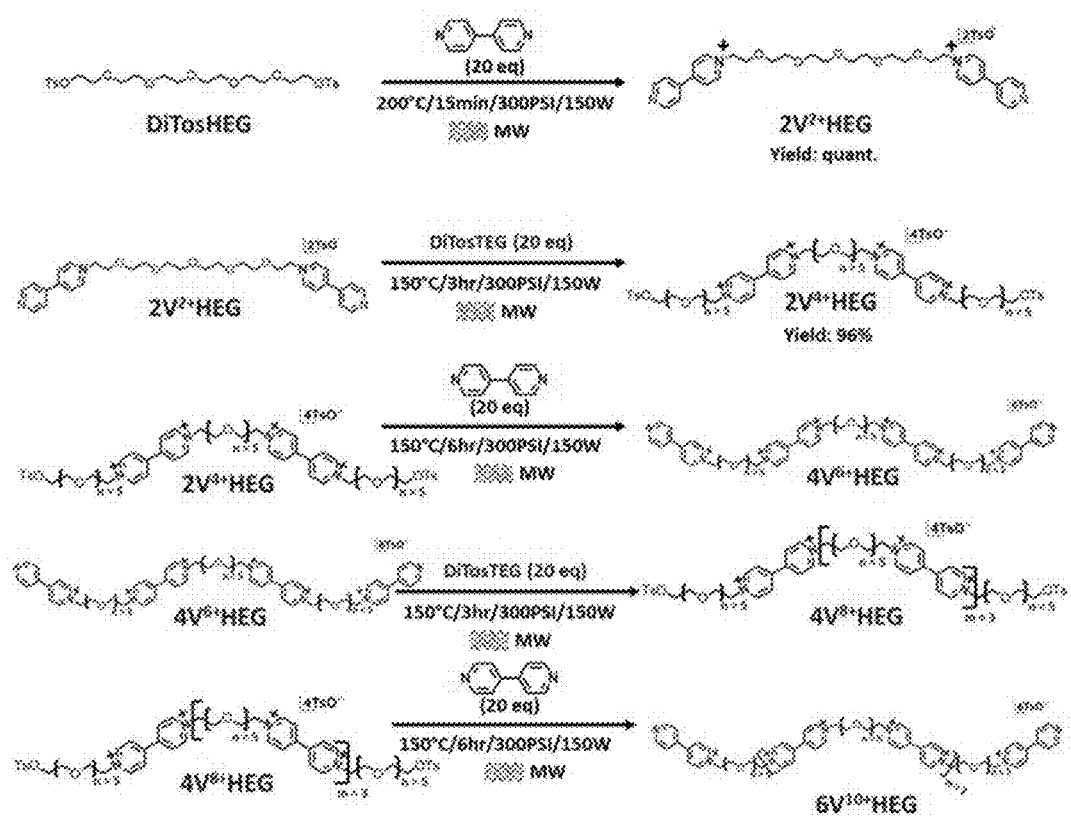
FIG. 26 is a series of schemes showing the faster and scaled synthesis of redox-active polyviologens using microwave irradiation to accelerate the process.

The synthesis reported in the above examples have been improved by implementing a microwave-assisted protocol that allows for the reported polyviologens to be prepared in a significantly reduced amount of time and on a larger scale (see e.g., FIG. 26). Specifically, the individual steps that previously required anywhere from 16-24 hours to go to completion can now be achieved on a timescale that ranges between 15 minutes for the first step, up to a maximum of 3-6 hours for the latter synthetic steps. This means that we can make a higher molecular weight polyviologen in about 4 days, compared to the 2 weeks previously required. Moreover, the 8V·16Tos and 10V·20Tos polyviologens are also synthesized on a gram-scale, whereas the previous method produced about 100 mg to about 200 mg of each. This improved synthetic rate and scale will allow for further implementation and investigation of functional materials and their properties.

What is claimed is:

1. A composition comprising:
   a photoredox-responsive material, a photocatalyst, and a cross-linking component;
   wherein,
   the photoredox-responsive material comprises a redox-active composition comprising a unimolecular, sequence-defined polyviologen;
   the redox-active composition is covalently linked to the cross-linking component; and
   the redox-active composition is covalently linked to the photocatalyst.

2. The composition of claim 1, further comprising a polymer.

3. The composition of claim 1, wherein the photoredox-responsive material comprises:
   a viologen oligomer or viologen polymer;
   a viologen oligomer or viologen polymer possessing n number of viologen subunits, wherein n=2, 3, 4, 5, 6, 7, 8, 9, 10, 11, 12, 13, 14, 15, 16, 17, 18, 19, or 20; or
   a reversibly reduced viologen ($V^{\cdot+}$), a neutral viologen ($V^0$), or an oxidized viologen ($V^{2+}$).

4. The composition of claim 1, wherein the photocatalyst is a visible-light absorbing catalyst.

5. The composition of claim 4, wherein the photocatalyst is selected from a ruthenium-based photocatalyst, ruthenium (II) trisbipyridine complex, or $Ru(bpy)_3Cl_2$.

6. The composition of claim 2, wherein the polymer comprises:
(i) a polyether, a polyurethane, a polyester, a polyamino acid, a polysaccharide, a bioerodible polymer, a vinyl polymer, a natural polymer, an acrylate, or copolymers or combinations thereof; or
(ii) a polyviologen, an acrylate, a vinyl, an alkyne-functionalized acrylate, a PEG, or a PAA, or copolymers or combination thereof.

7. The composition of claim 1, wherein the cross-linking component is selected from a multi-armed cross-linker.

8. The composition of claim 7, wherein the multi-armed cross-linker is selected from a $SiO_2$ nanoparticle (SNP), a viologen, or a tri- or tetra-alkyne cross-linker (TAXL).

9. The composition of claim 1, wherein the photocatalyst is covalently bound to the photoredox-responsive material as a functional group.

10. The composition of claim 1, wherein, upon exposure to light, the photoredox-responsive material comprises stacked polyviologen subunits and a contracted polymer network.

11. The composition of claim 1, wherein the photoredox-responsive material is an actuating photoredox-responsive material.

12. A method of producing a composition comprising a photoredox-responsive material, comprising
providing a redox-active composition comprising a unimolecular, sequence-defined viologen;
providing a photocatalyst;
providing a cross-linking component;
introducing the redox-active composition, the photocatalyst, and the cross-linking component; and
forming a solvated nanocomposite polymer network by cross-linking the redox-active composition, wherein the polymer network comprises a unimolecular, sequence-defined polyviologen.

13. The method of claim 12, wherein
the photoredox-responsive material comprises a viologen oligomer or a viologen polymer comprising n number of viologen subunits, wherein n=2, 3, 4, 5, 6, 7, 8, 9, 10, 11, 12, 13, 14, 15, 16, 17, 18, 19, or 20;
the composition is an actuating photoredox-responsive material;
the photocatalyst is incorporated into the photoredox-responsive material as a free photocatalyst or covalently bound to the photoredox-responsive material as a functional group;
the photoredox-responsive material comprises a polymer;
the viologen is, reversibly, a reduced viologen ($V^{•+}$), a neutral viologen ($V^0$), or an oxidized viologen ($V^{2+}$);
the photocatalyst is a visible-light absorbing catalyst; or
the cross-linking component is selected from a multi-armed cross-linker.

14. The method of claim 13, wherein the photocatalyst is selected from a ruthenium-based photocatalyst, a ruthenium (II) trisbipyridine complex, or $Ru(bpy)_3Cl_2$.

15. The method of claim 13, wherein the polymer comprises:
(i) a polyether, a polyurethane, a polyester, a polyamino acid, a polysaccharide, a bioerodible polymer, a vinyl polymer, a natural polymer, an acrylate, or copolymers or combinations thereof; or
(ii) a polyviologen, an acrylate, a vinyl, an alkyne-functionalized acrylate, a PEG, or a PAA, or copolymers or combination thereof.

16. The method of claim 13, wherein the multi-armed cross-linker is selected from a $SiO_2$ nanoparticle (SNP), a viologen, or a tri- or tetra-alkyne cross-linker (TAXL).

17. The method of claim 12, wherein
(i) upon exposure to light, the photoredox-responsive material comprises stacked viologen subunits and a contracted polymer network;
(ii) shining a light with a wavelength matching the wavelength of photocatalyst absorption on the photoredox-responsive material, results in a stacking of viologen subunits and a contraction of the polymer network by photo-induced electron transfer (PET) from the photocatalyst to the viologen subunits;
(iii) introduction of a sacrificial reductant results in a decrease in electrostatic repulsion, loss of corresponding counteranions, or an intramolecular folding of polyviologen chains; or
(iv) the photoredox-responsive material is in a contracted state when reduced and in an expanded state when oxidized.

18. The method of claim 17, wherein the photoredox-responsive material comprises:
the photocatalyst comprising $[Ru(bpy)_3]^{2+}$;
the sacrificial reductant comprising triethanolamine (TEOA);
about 80 mol % to about 100 mol % PEG;
about 0 mol % to about 20 mol % of the unimolecular, sequence-defined polyviologen; and
a cross-linker selected from viologen, tetra-alkyne, or SNP.

19. A method of using the composition of claim 1 in a soft robotic; in a drug delivery device; in a light-activated transdermal patch; for patterning a surface using light; in a shape changing material; in an electrochromic material; in a redox flow battery; in a self-healing material; in a mechanical actuator; in a sensor; or in an artificial muscle.

20. The composition of claim 1, wherein the composition is produced according to a method comprising:
providing a photoredox-responsive material;
providing a photocatalyst;
introducing the photoredox-responsive material and the photocatalyst; and
forming a solvated nanocomposite polymer network by cross-linking the photoredox-responsive material.

21. The composition of claim 1, wherein the
the photocatalyst comprises $[Ru(bpy)_3]^{2+}$;
the photoredox-responsive material comprises a sacrificial reductant comprises triethanolamine (TEOA);
the photoredox-responsive material comprises about 80 mol % to about 100 mol % PEG;
the photoredox-responsive material comprises about 0 mol % to about 20 mol % of the unimolecular, sequence-defined polyviologen; and
the cross-linking component is selected from viologen, tetra-alkyne, or SNP.

22. The composition of claim 1, wherein the composition is used in a soft robotic; in a drug delivery device; in a light-activated transdermal patch; for patterning of surfaces using light; in a shape changing material; in an electrochromic material; in a redox flow battery; in a self-healing material; in a mechanical actuator; in a sensor; or in an artificial muscle.

* * * * *